(12) United States Patent
McCauley et al.

(10) Patent No.: US 8,512,990 B2
(45) Date of Patent: Aug. 20, 2013

(54) CATALYTIC DOMAINS FROM LYSYL OXIDASE AND LOXL2

(75) Inventors: Scott McCauley, Brisbane, CA (US); Victoria Smith, Burlingame, CA (US)

(73) Assignee: Gilead Biologics, Inc., Foster City, CA (US)

( * ) Notice: Subject to any disclaimer, the term of this patent is extended or adjusted under 35 U.S.C. 154(b) by 313 days.

(21) Appl. No.: 12/860,625

(22) Filed: Aug. 20, 2010

(65) Prior Publication Data

US 2011/0076739 A1 Mar. 31, 2011

Related U.S. Application Data

(60) Provisional application No. 61/235,776, filed on Aug. 21, 2009.

(51) Int. Cl.
*C12N 9/02* (2006.01)
(52) U.S. Cl.
USPC .......................................................... 435/189
(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,485,088 A | 11/1984 | Chvapil |
| 4,545,382 A | 10/1985 | Higgins et al. |
| 4,637,403 A | 1/1987 | Barcia et al. |
| 4,666,828 A | 5/1987 | Gusella |
| 4,683,202 A | 7/1987 | Mullis |
| 4,731,374 A | 3/1988 | Griss et al. |
| 4,748,116 A | 5/1988 | Simonsson et al. |
| 4,801,531 A | 1/1989 | Frossard |
| 4,816,567 A | 3/1989 | Cabilly et al. |
| 4,843,086 A | 6/1989 | Griss et al. |
| 4,879,219 A | 11/1989 | Wands et al. |
| 4,886,812 A | 12/1989 | Griss et al. |
| 4,943,593 A | 7/1990 | Palfreyman et al. |
| 4,946,778 A | 8/1990 | Ladner et al. |
| 4,965,288 A | 10/1990 | Palfreyman et al. |
| 4,997,854 A | 3/1991 | Kagen et al. |
| 5,011,771 A | 4/1991 | Bellet et al. |
| 5,021,404 A | 6/1991 | Folkman et al. |
| 5,021,456 A | 6/1991 | Palfreyman et al. |
| 5,059,714 A | 10/1991 | Palfreyman et al. |
| 5,120,764 A | 6/1992 | McCarthy et al. |
| 5,182,297 A | 1/1993 | Palfreyman et al. |
| 5,192,659 A | 3/1993 | Simons |
| 5,252,608 A | 10/1993 | Palfreyman et al. |
| 5,262,035 A | 11/1993 | Gregg et al. |
| 5,272,057 A | 12/1993 | Smulson et al. |
| 5,281,521 A | 1/1994 | Trojanowski et al. |
| 5,545,806 A | 8/1996 | Lonberg et al. |
| 5,545,807 A | 8/1996 | Surani et al. |
| 5,625,126 A | 4/1997 | Lonberg et al. |
| 5,633,425 A | 5/1997 | Lonberg et al. |
| 5,641,484 A | 6/1997 | Hung et al. |
| 5,661,016 A | 8/1997 | Lonberg et al. |
| 5,721,138 A | 2/1998 | Lawn |
| 6,015,562 A | 1/2000 | Hinman et al. |
| 6,140,056 A | 10/2000 | Khodadoust |
| 6,225,118 B1 | 5/2001 | Grant et al. |
| 6,277,622 B1 | 8/2001 | Weiss |
| 6,300,092 B1 | 10/2001 | Khodadoust et al. |
| 6,303,318 B1 | 10/2001 | O'Brien |
| 6,316,416 B1 | 11/2001 | Patierno et al. |
| 6,326,174 B1 | 12/2001 | Joyce et al. |
| 6,391,602 B1 | 5/2002 | Khodadoust |
| 6,534,261 B1 | 3/2003 | Cox, III et al. |
| 6,808,707 B2 | 10/2004 | Ensley |
| 7,112,668 B2 | 9/2006 | Rastelli et al. |
| 7,208,300 B2 | 4/2007 | Evans et al. |
| 7,255,856 B2 | 8/2007 | Li et al. |
| 7,255,857 B2 | 8/2007 | Li et al. |
| 7,335,294 B2 | 2/2008 | Heller et al. |
| 7,348,170 B2 | 3/2008 | Yuuki et al. |
| 7,396,920 B2 | 7/2008 | Hemmings et al. |
| 7,445,920 B2 | 11/2008 | Evans et al. |
| 7,585,634 B2 | 9/2009 | Kim et al. |
| 8,163,494 B2 | 4/2012 | Neufeld et al. |
| 8,168,180 B2 | 5/2012 | Neufeld et al. |
| 2001/0005581 A1 | 6/2001 | Grant et al. |
| 2001/0012890 A1 | 8/2001 | Thompson |
| 2002/0072089 A1 | 6/2002 | Holtzman et al. |
| 2002/0123476 A1 | 9/2002 | Emanuele et al. |
| 2002/0128218 A1 | 9/2002 | Emanuele et al. |
| 2002/0151007 A1 | 10/2002 | Khodadoust et al. |
| 2002/0156263 A1 | 10/2002 | Chen |
| 2003/0008023 A1 | 1/2003 | Lu |
| 2003/0017068 A1 | 1/2003 | Larrain et al. |
| 2003/0092037 A1 | 5/2003 | Matsuzaki et al. |

(Continued)

FOREIGN PATENT DOCUMENTS

| | | |
|---|---|---|
| EP | 0186087 | 8/1989 |
| EP | 0375408 | 6/1990 |

(Continued)

OTHER PUBLICATIONS

Peroutka, et al. (2008) "Enhanced Protein Expression in Mammalian Cells Using Engineered SUMO Fusions: Secreted phospholipase A2" Protein Sci. 17(9):1586-1595.

(Continued)

*Primary Examiner* — Tekchand Saidha
*Assistant Examiner* — Younus Meah
(74) *Attorney, Agent, or Firm* — Morrison & Foerster LLP

(57) ABSTRACT

Disclosed herein are amino acid sequences, and encoding nucleotide sequences, of isolated catalytic domains of the LOX and LOXL2 proteins from human and mouse. Methods for the preparation and use of these isolated catalytic domains are also provided.

11 Claims, 7 Drawing Sheets

(56) References Cited

U.S. PATENT DOCUMENTS

| | | |
|---|---|---|
| 2003/0096980 A1 | 5/2003 | Froehler et al. |
| 2003/0099213 A1 | 5/2003 | Lee et al. |
| 2003/0114410 A1 | 6/2003 | Neufeld et al. |
| 2003/0129672 A1 | 7/2003 | Dyer et al. |
| 2003/0149997 A1 | 8/2003 | Hageman |
| 2003/0152926 A1 | 8/2003 | Murray et al. |
| 2003/0211076 A1 | 11/2003 | Li et al. |
| 2004/0009154 A1 | 1/2004 | Khan et al. |
| 2004/0029114 A1 | 2/2004 | Mack et al. |
| 2004/0156854 A1 | 8/2004 | Mulligan et al. |
| 2004/0171110 A1 | 9/2004 | Evans et al. |
| 2004/0176296 A1 | 9/2004 | Holtzman et al. |
| 2004/0197328 A1 | 10/2004 | Young et al. |
| 2004/0213756 A1 | 10/2004 | Michal et al. |
| 2004/0248871 A1 | 12/2004 | Farjanel et al. |
| 2004/0253220 A1 | 12/2004 | Perrier et al. |
| 2004/0253606 A1 | 12/2004 | Aziz et al. |
| 2004/0258676 A1 | 12/2004 | Perrier et al. |
| 2004/0265230 A1 | 12/2004 | Martinez et al. |
| 2005/0020521 A1 | 1/2005 | Rana et al. |
| 2005/0079538 A1 | 4/2005 | Griffin et al. |
| 2005/0119202 A1 | 6/2005 | Kreutzer et al. |
| 2005/0181375 A1 | 8/2005 | Aziz et al. |
| 2005/0259483 A1 | 11/2005 | Nakamura et al. |
| 2005/0260639 A1 | 11/2005 | Nakamura et al. |
| 2006/0019256 A1 | 1/2006 | Clarke et al. |
| 2006/0088532 A1 | 4/2006 | Alitalo et al. |
| 2006/0088882 A1 | 4/2006 | Jain et al. |
| 2006/0127402 A1 | 6/2006 | Neufeld et al. |
| 2006/0127902 A1 | 6/2006 | Madden et al. |
| 2006/0134172 A1 | 6/2006 | Shepard et al. |
| 2006/0134801 A1 | 6/2006 | Chada et al. |
| 2006/0216722 A1 | 9/2006 | Betholtz et al. |
| 2006/0223760 A1 | 10/2006 | Li et al. |
| 2007/0010469 A1 | 1/2007 | Chan et al. |
| 2007/0021365 A1 | 1/2007 | Erler et al. |
| 2007/0037203 A1 | 2/2007 | Kapeller-Libermann |
| 2007/0054278 A1 | 3/2007 | Cargill |
| 2007/0059745 A1 | 3/2007 | Sharp et al. |
| 2007/0154481 A1 | 7/2007 | Gelinas et al. |
| 2007/0184439 A1 | 8/2007 | Guilford et al. |
| 2007/0197424 A1 | 8/2007 | Friedman et al. |
| 2007/0225242 A1 | 9/2007 | Erler et al. |
| 2007/0231323 A1 | 10/2007 | Phillips |
| 2007/0243214 A1 | 10/2007 | Schiemann et al. |
| 2008/0031817 A1 | 2/2008 | Mazar et al. |
| 2008/0118928 A1 | 5/2008 | Hageman |
| 2008/0137893 A1 | 6/2008 | Ross et al. |
| 2008/0181896 A1 | 7/2008 | Khan et al. |
| 2008/0187523 A1 | 8/2008 | Zhang et al. |
| 2008/0220424 A1 | 9/2008 | Haber et al. |
| 2008/0248477 A1 | 10/2008 | Holtzman et al. |
| 2008/0261870 A1 | 10/2008 | Trackman et al. |
| 2008/0274453 A1 | 11/2008 | Hageman |
| 2008/0279857 A1 | 11/2008 | Skerry et al. |
| 2008/0286808 A1 | 11/2008 | Schellenberger et al. |
| 2008/0292547 A1 | 11/2008 | Tolleshaug et al. |
| 2008/0305965 A1 | 12/2008 | Moorhouse et al. |
| 2009/0022703 A1 | 1/2009 | Li et al. |
| 2009/0023149 A1 | 1/2009 | Knudsen et al. |
| 2009/0035348 A1 | 2/2009 | Zadini et al. |
| 2009/0053224 A1 | 2/2009 | Smith et al. |
| 2009/0104201 A1 | 4/2009 | Smith et al. |
| 2009/0142301 A1 | 6/2009 | Bevec et al. |
| 2009/0232773 A1 | 9/2009 | Kato et al. |
| 2009/0233270 A9 | 9/2009 | St. Croix et al. |
| 2009/0239947 A1 | 9/2009 | Dai et al. |
| 2009/0275633 A1 | 11/2009 | Esteller |
| 2010/0119515 A1 | 5/2010 | Neufeld et al. |
| 2010/0144603 A1 | 6/2010 | Watnick |
| 2010/0203062 A1 | 8/2010 | Stalmans et al. |
| 2010/0209415 A1 | 8/2010 | Smith et al. |
| 2010/0317721 A1 | 12/2010 | Neufeld |
| 2011/0044907 A1 | 2/2011 | Marshall et al. |
| 2011/0044981 A1 | 2/2011 | Spangler et al. |
| 2011/0076272 A1 | 3/2011 | Smith et al. |
| 2011/0076285 A1 | 3/2011 | Stalmans et al. |
| 2011/0200606 A1 | 8/2011 | McCauley et al. |
| 2011/0207144 A1 | 8/2011 | Marshall et al. |
| 2012/0087917 A1 | 4/2012 | Smith et al. |
| 2012/0165398 A1 | 6/2012 | Neufeld et al. |
| 2012/0202206 A1 | 8/2012 | Neufeld et al. |
| 2012/0309020 A1 | 12/2012 | Smith et al. |
| 2013/0017207 A1 | 1/2013 | Smith et al. |

FOREIGN PATENT DOCUMENTS

| | | |
|---|---|---|
| EP | 0 799 891 | 10/1997 |
| EP | 0960192 | 12/1999 |
| EP | 1149169 | 10/2001 |
| EP | 1 616 881 | 1/2006 |
| EP | 1 693 448 | 8/2006 |
| EP | 1690932 | 8/2006 |
| EP | 1715035 | 10/2006 |
| EP | 2078531 | 7/2009 |
| WO | WO 8912060 | 12/1989 |
| WO | WO-92/20702 | 11/1992 |
| WO | WO 9220702 | 11/1992 |
| WO | WO-96/00614 | 1/1996 |
| WO | WO 9600614 | 1/1996 |
| WO | WO 9640746 | 1/1996 |
| WO | WO-96/40746 | 12/1996 |
| WO | WO-97/00441 | 1/1997 |
| WO | WO 9700441 | 1/1997 |
| WO | WO-98/06830 | 2/1998 |
| WO | WO 9806830 | 2/1998 |
| WO | WO-99/65928 | 12/1999 |
| WO | WO 9965928 | 12/1999 |
| WO | WO-00/44910 | 3/2000 |
| WO | WO 0044910 | 8/2000 |
| WO | WO 0183702 | 11/2001 |
| WO | WO-01/92495 | 12/2001 |
| WO | WO 0192495 | 12/2001 |
| WO | WO-02/11667 | 2/2002 |
| WO | WO 0211667 | 2/2002 |
| WO | WO 0261092 | 2/2002 |
| WO | WO-02/061092 | 8/2002 |
| WO | WO 02079492 | 8/2002 |
| WO | WO-02/079492 | 10/2002 |
| WO | WO-02/086443 | 10/2002 |
| WO | WO 02086443 | 10/2002 |
| WO | WO-03/031939 | 4/2003 |
| WO | WO 03031939 | 4/2003 |
| WO | WO 03100016 | 4/2003 |
| WO | WO-03/100016 | 12/2003 |
| WO | WO-2004/023973 | 3/2004 |
| WO | WO 2004023973 | 3/2004 |
| WO | WO 2004047720 | 6/2004 |
| WO | WO-2004/061423 | 7/2004 |
| WO | WO 2004091655 | 10/2004 |
| WO | WO-2005/100604 | 10/2005 |
| WO | WO 2005100604 | 10/2005 |
| WO | WO-2006/128740 | 7/2006 |
| WO | WO 2006128740 | 12/2006 |
| WO | WO-2007/045927 | 4/2007 |
| WO | WO 2007045927 | 4/2007 |
| WO | WO 2007126457 | 11/2007 |
| WO | WO-2008/063479 | 5/2008 |
| WO | WO 2008063479 | 5/2008 |
| WO | WO 2008070616 | 5/2008 |
| WO | WO-2008/070616 | 6/2008 |
| WO | WO 2008132453 | 6/2008 |
| WO | WO-2008/132453 | 11/2008 |
| WO | WO-2008/138578 | 11/2008 |
| WO | WO 2008138578 | 11/2008 |
| WO | WO 2009010974 | 1/2009 |
| WO | WO 2009035791 | 1/2009 |
| WO | WO-2009/017833 | 2/2009 |
| WO | WO-2009/035791 | 3/2009 |
| WO | WO-2010/080769 | 7/2010 |
| WO | WO-2010/091279 | 8/2010 |
| WO | WO-2011/022667 | 2/2011 |
| WO | WO-2011/022670 | 2/2011 |
| WO | WO-2011/022706 | 2/2011 |
| WO | WO-2011/022709 | 2/2011 |

| WO | WO-2011/022710 | 2/2011 |
| WO | WO-2011/041309 | 4/2011 |
| WO | WO-2011/097513 | 8/2011 |
| WO | WO-2012/167181 | 12/2012 |

OTHER PUBLICATIONS

Vadasz, et al. (2005) "Abnormal Deposition of Collagen around Hepatocytes in Wilson's Disease Is Associated with Hepatocyte Specific Expression of Lysyl Oxidase and Lysyl Oxidase Like Protein-2" *J. Hepatol.* 43(3):499-507. Abstract Only.

Akiri et al. (2003) "Lysyl Oxidase-Related Protein-1 Promotes Tumor Fibrosis and Tumor Progression in Vivo" *Cancer Res.* 63(7):1657-1666.

Albini et al. (1987) "A Rapid In Vitro Assay for Quantitating the Invasive Potential of Tumor Cells" *Cancer Res.* 47(12):3239-3245.

Asuncion et al. (2001) "A Novel Human Lysyl Oxidase-Like Gene (LOXL4) on Chromosome 10q24 Has an Altered Scavenger Receptor Cysteine Rich Domain" *Matrix Biol.* 20(7):487-491.

Borel et al. (2001) "Lysyl Oxidase-Like Protein from Bovine Aorta. Isolation and Maturation to an Active Form by Bone Morphogenetic Protein-1"*J. Biol. Chem.*276(52):48944-48949.

Bronson et al. (2005) "LOXL Null Mice Demonstrate Selective Dentate Structural Changes but Maintain Dentate Granule Cell and CA1 Pyramidal Cell Potentiation in the Hippocampus" *Neurosci. Lett.* 390(2):118-122.

Csiszar (2001) "Lysyl Oxidases: a Novel Multifunctional Amine Oxidase Family" *Prog. Nucl. Acid Res.* 70:1-32.

GenBank Accession No. AAA59525.1 "Lysyl Oxidase [*Homo sapiens*]".

GenBank Accession No. AAA59541.1 "Lysyl Oxidase [*Homo sapiens*]".

GenBank Accession No. AAB21243.1 "Lysyl Oxidase [*Homo sapiens*]".

GenBank Accession No. AAB23549.1 "Lysyl Oxidase [*Homo sapiens*]".

GenBank Accession No. AAD02130.1 "Lysyl Oxidase [*Homo sapiens*]".

GenBank Accession No. AAH15090.1 "Lysyl Oxidase-Like 1 [*Homo sapiens*]".

GenBank Accession No. AAH74820.1 "Lysyl Oxidase [*Homo sapiens*]".

GenBank Accession No. AAH74872.1 "Lysyl Oxidase [*Homo sapiens*]".

GenBank Accession No. AAK51671.1 "Lysyl Oxidase-Like 3 Protein [*Homo sapiens*]".

GenBank Accession No. AAK71934.1 "Lysyl Oxidase-Related Protein C [*Homo sapiens*]".

GenBank Accession No. AF039291 "*Homo sapiens* Lysyl Oxidase mRNA, Complete cds".

GenBank Accession No. AF282619 "*Homo sapiens* Lysyl Oxidase-like 3 Protein mRNA, Complete cds".

GenBank Accession No. AF338441 "*Homo sapiens* Lysyl Oxidase-Related Protein C (LOXC) mRNA, Complete cds".

GenBank Accession No. BC015090 "*Homo sapiens* Lysyl Oxidase-Like 1, mRNA (cDNA Clone MGC:16541 Image:4040510), Complete cds".

GenBank Accession No. BC018439 "*Mus musculus* Lysyl Oxidase, mRNA (cDNA Clone MGC:11525 Image:2655752), Complete cds".

GenBank Accession No. BC074820 "*Homo sapiens* Lysyl Oxidase, mRNA (cDNA Clone MGC:104085 Image: 30915536), Complete cds".

GenBank Accession No. BC074872 "*Homo sapiens* Lysyl Oxidase, mRNA (cDNA Clone MGC:103851 Image:30915233), Complete cds".

GenBank Accession No. M84150 "Human Lysyl Oxidase Gene, Partial cds".

GenBank Accession No. M94054 "Human Lysyl Oxidase (LOX) mRNA, Complete cds".

GenBank Accession No. NM_002317 "*Homo sapiens* Lysyl Oxidase (LOX), Transcript Variant 1, mRNA".

GenBank Accession No. NM_033325 "*Mus musculus* Lysyl Oxidase-Like 2 (Lox12), mRNA".

GenBank Accession No. NP_002308 "Protein-Lysine 6-Oxidase Isoform 1 Preproprotein [*Homo sapiens*]".

GenBank Accession No. NP_002309 "Lysyl Oxidase Homolog 2 Precursor [*Homo sapiens*]".

GenBank Accession No. NP_005567 "Lysyl Oxidase Homolog 1 Preproprotein [*Homo sapiens*]".

GenBank Accession No. NP_034858 "Protein-Lysine 6-Oxidase Precursor [*Mus musculus*]".

GenBank Accession No. NP_034859 "Lysyl Oxidase Homolog 1 Precursor [*Mus musculus*]".

GenBank Accession No. NP_115587 "Lysyl Oxidase Homolog 4 Precursor [*Homo sapiens*]".

GenBank Accession No. NP_115882 "AP-1 Complex Subunit mu-1 Isoform 2 [*Homo sapiens*]".

GenBank Accession No. NP_201582 "Lysyl Oxidase homolog 2 Precursor [*Mus musculus*]".

GenBank Accession No. S45875 "Lysyl Oxidase [Human, Skin Fibroblasts, mRNA Partial, 1254 nt]".

GenBank Accession No. 578694 "Lysyl Oxidase [Human, mRNA, 1780 nt]".

GenBank Accession No. U89942 "Human Lysyl Oxidase-Related Protein (WS9-14) mRNA, Complete cds".

Giampuzzi et al. (2000) "Lysyl Oxidase Activates the Transcription Activity of Human Collagene III Promoter. Possible Involvement of Ku Antigen" *J. Biol. Chem.* 275(46):36341-36349.

Görögh et al. (2007) "Selective Upregulation and Amplification of the Lysyl Oxidase Like-4 (LOXL4) Gene in Head and Neck Squamous cell Carcinoma" *J. Pathol.* 212(1):74-82.

Harris et al. (1974) "Connective Tissue Amine Oxidase. II. Purification and Partial Characterization of Lysyl Oxidase from Chick Aorta" *Biochim. Biophys. Acta* 341(2):332-344.

Hohenester et al. (1999) "Crystal Structure of a Scavenger Receptor Cysteine-Rich Domain Sheds Light on an Ancient Superfamily" *Nat. Struct. Biol.* 6(3):228-232.

Hornstra et al. (2003) "Lysyl Oxidase is Required for Vascular and Diaphragmatic Development in Mice" *J. Biol. Chem.* 278(16):14387-14393.

Huang et al. (2001) "Cloning and Characterization of a Human Lysyl Oxidase-Like 3 Gene (hLOXL3)" *Matrix Biol.* 20(2):153-157.

Ito et al. (2001) "Molecular Cloning and Biological Activity of a Novel Lysyl Oxidase-Related Gene Expressed in Cartilage" *J. Biol. Chem.* 276(26):24023-24029.

Jourdan Le-Saux et al. (1994) "Lysyl Oxidase cDNA of Myofibroblast from Mouse Fibrotic Liver" *Biochem. Biophys. Res. Comm.* 199(2):587-592.

Jourdan Le-Saux et al. (1999) "The LOXL2 Gene Encodes a New Lysyl Oxidase-Like Protein and Is Expressed at High Levels in Reproductive Tissues" *J. Biol. Chem.* 274(18):12939-12944.

Jourdan Le-Saux et al. (2001) "Central Nervous System, Uterus, Heart, and Leukocyte Expression of the LOXL3 Gene, Encoding a Novel Lysyl Oxidase-Like Protein" *Genomics* 74(2):211-218.

Kagan et al. (1982) "Lysyl Oxidase: Preparation and Role in Elastin Biosynthesis" *Meth. Enzymol.* 82(A):637-649.

Kagan et al. (2003) "Lysyl Oxidase: Properties, Specificity, and Biological Roles Inside and Outside of the Cell" *J. Cell. Biochem* 88(4):660-672.

Kagan (1994) "Lysyl Oxidase: Mechanism, Regulation and Relationship to Liver Fibrosis" *Pathol. Res. Pract.* 190(9-10):910-919.

Kamath et al. (2001) "Signaling from Protease-Activated Receptor-1 Inhibits Migration and Invasion of Breast Cancer Cells" *Cancer Res.* 61(15):5933-5940.

Kim et al. (1995) "A New Gene with Sequence and Structural Similarity to the Gene Encoding Human Lysyl Oxidase" *J. Biol. Chem.* 270(13):7176-7182.

Kim et al. (1999) "Coexpression of the Lysyl Oxidase-Like Gene (LOXL) and the Gene Encoding Type III Procollagen in Induced Liver Fibrosis" *J. Cell Biochem.* 72(2):181-188.

Kim et al. (2003) "Expression and Purification of Enzymatically Active Forms of the Human Lysyl Oxidase-Like Protein 4" *J. Biol. Chem.* 278(52):52071-52074.

Kirschmann et al. (2002) "A Molecular Role for Lysyl Oxidase in Breast Cancer Invasion Cancer Res." *Cancer Res.* 62(15):4478-4483.

Lazarus et al. (1995) "Induction of Human Monocyte Motility by Lysyl Oxidase" *Matrix Biol.* 14(9):727-731.

Li et al. (1997) "Localization and Activity of Lysyl Oxidase within Nuclei of Fibrogenic Cells" *Proc. Natl. Acad. Sci. USA* 94(24):12817-12822.

Maki & Kivirikko (2001) "Cloning and Characterization of a Fourth Human Lysyl Oxidase Isoenzyme" *Biochem. J.* 355(Pt 2):381-387.

Molnar et al. (2003) "Structural and functional diversity of lysyl oxidase and the LOX-like proteins" *Biochim Biophys Acta.* 1647(1-2):220-224.

Murawaki et al. (1991) "Serum Lysyl Oxidase Activity in Chronic Liver Disease in Comparison with Serum Levels of Prolyl Hydroxylase and Laminin" *Hepatology* 14(6):1167-1173.

Nelson et al. (1988) "Effect of beta-Aminopropionitrile and Ascorbate on Fibroblast Migration" *Proc. Soc. Exp. Biol. Med.* 188(3):346-352.

Palamakumbura et al. (2002) "A Fluorometric Assay for Detection of Lysyl Oxidase Enzyme Activity in Biological Samples" *Anal. Biochem.* 300(2):245-251.

Rayton et al. (1979) "Induction of Lysyl Oxidase with Copper. Properties of an In Vitro System" *J. Biol. Chem.* 254(3):621-626.

Rucker et al. (1998) "Copper, Lysyl Oxidase, and Extracellular Matrix Protein Cross-Linking" *Am. J. Clin. Nutr.* 67(5 Suppl):996S-1002S.

Sasaki et al. (1998) "Mac-2 Binding Protein is a Cell-Adhesive Protein of the Extracellular Matrix Which Self-Assembles into Ring-Like Structures and Binds β1 Integrins, Collagens and Fibronectin" *EMBO J.* 17(6):1606-1613.

Siegel et al. (1978) "Biochemical and Immunochemical Study of Lysyl Oxidase in Experimental Hepatic Fibrosis in the Rat" *Proc. Natl. Acad. Sci. USA* 75(6):2945-2949.

Stassen (1976) "Properties of Highly Purified Lysyl Oxidase from Embryonic Chick Cartilage" *Biophys. Acta* 438(1):49-60.

Trackman et al. (1981) "Development of a Peroxidase-Coupled Fluorometric Assay for Lysyl Oxidase" *Anal. Biochem.* 113(2):336-342.

Wu et al. (2007) "LOXL1 and LOXL4 are Epigenetically Silenced and Can Inhibit Ras/Extracellular Signal-Regulated Kinase Signaling Pathway in Human Bladder Cancer" *Cancer Res.* 67(9):4123-4129.

U.S. Appl. No. 12/860,632, filed Aug. 20, 2010, Marshall, et al.

U.S. Appl. No. 13/021,555, filed Feb. 4, 2011, McCauley, et al.

"The role of The Extracellular Matrix in Cancer" Mar. 2001, U.S. Department of Energy: http:www.science.doe.gov/Accomplishments_Awards/Decades_Discovery/85.html.

Adamson, et al. (1974) "The Pathogenesis of Bleomycin-Induced Pulmonary Fibrosis in Mice" Am. J. Pathol. 77(2):185-189.

Akagawa, et al. (2007). "Systematic screening of lysyl oxidase-like (LOXL) family genes demonstrates that LOXL2 is a susceptibility gene to intracranial aneurysms." Hum Genet 121(3-4): 377-87.

Arguello et al. (1992) "Incidence and Distribution of Experimental Metastases in Mutant Mice with Defective Organ Microenvironments (Genotypes S1/S1d and W/Wv)" *Cancer Research* 52(8):2304-2309.

Atabani, et al. (1997) "Identification of an Immunodominant Neutralizing and Protective Epitope from Measles Virus Fusion Protein by Using Human Sera from Acute Infection" J. Virology 71(10):7240-7245.

Atsawasuwan, et al. (2005). "Expression of lysyl oxidase isoforms in MC3T3-E1 osteoblastic cells." Biochem Biophys Res Commun 327(4): 1042-6.

Atsawasuwan, et al. (2008). "Lysyl oxidase binds transforming growth factor-β and regulates its signaling via amine oxidase activity." J Biol Chem 283(49): 34229-40.

Auerbach et al. (2003) "Angiogenesis Assays: A Critical Overview" *Clinical Chemistry* 49(1):32-40.

Barker, et al. (2011) "LOXL2-mediated matrix remodeling in metastasis and mammary gland involution" Cancer Res., 71(5):1561-1572.

Barry-Hamilton, et al. (2010) "Allosteric inhibition of lysyl oxidase-like-2 impedes the development of a pathologic microenvironment" Nat.Med., 19(9):1009-1017.

Barzu, et al. "Characterization of B-Cell Epitopes on IpaB, an Invasion-Associated Antigen of *Shigella flexneri*: Identification of an Immunodominant Domain Recognized during Natural Infection" Infection and Immunity, Sep. 1993, vol. 61, No. 9, pp. 3825-3831.

Bendig (1995) "Humanization of Rodent Monoclonal Antibodies by CDR Grafting" Methods: Companion to Methods in Enzymology 8:83-93.

Berithaupt, et al. (2008) "Demyelinating Myelin Oligodendrocyte Glycoprotein-Specific Autoantibody Response Is Focused on one Dominant Conformational Epitope Region in Rodents" J. Immunology 181(2):1255-1263.

Betakova, et al. (1998) "Monoclonal Anti-Idiotypic Antibodies Mimicking the Immunodominant Epitope of Influenza Virus Haemagglutinin Elicit Biologically Significant Immune Responses" J. Gen. Virology 79(Pt.3):461-470.

Bhowmick, et al. (2004). "Stromal fibroblasts in cancer initiation and progression." Nature 432(7015): 332-7.

Boneberg, et. al. (2009) "Angiogenesis and lymphangiogenesis are downregulated in primary breast cancer" Br. J. Cancer, 101(4):605-614.

Bouez, et al. (2006) "The Lysyl Oxidase LOX is Absent in Basal and Squamous Cell Carcinomas and its Knockdown Induces an Invading Phenotype in a Skin Equivalent Model" Clinical Cancer Res. 12(5) 1463-1469.

Brody, et al. (1976) "Lung lysyl oxidase and elastin synthesis during compensatory lung growth" *Chest* 69(2 Suppl):271-272.

Brown, et al. (2004) "Exploiting Tumour Hypoxia in Cancer Treatment" Nature Reviews 4:437-447.

Brukamp, et al. (2007) "Hypoxia and Podocyte-Specific Vhlh Deletion Confer Risk of Glomerular Disease" Am. J. Physiol. Renal. Physiol. 293(4):F1397-F1407.

Bruns, et al. "Vascular Endothelial Growth Factor Is an In Vivo Survival Factor for Tumor Endothelium in a Murine Model of Colorectal Carcinoma Liver Metastases" *Cancer*, 2000 vol. 89, No. 3, pp. 488-499.

Burbelo, et al. (1986) "Monoclonal Antibodies to Human Lysyl Oxidase" Coll. Relat. Res. 6(2):153-62.

Butcher, et al. (2009) "A Tense Situation: Forcing Tumour Progression" Nat. Rev. Cancer 9(2):108-122.

Cairns, et al. (2004) "Acute Hypoxia Enhances Spontaneous Lymph Node Metastasis in an Orthotopic Murine Model of Human cervical Carcinoma" Cancer Res. 64:2054-2061.

Cancer Reference Information; Detailed guide: Breast cancer, how is breast cancer diagnosed? www.cancer.org/docroot/CRI_2_4_3X_How_is_breast_cancer_diagnosed, Nov. 16, 2009.

Cardone, et al. (1997). "Prognostic value of desmoplastic reaction and lymphocytic infiltration in the management of breast cancer." Panminerva Med 39(3): 174-7.

Chan, et al. (2007) "Hypoxia, Gene Expression, and Metastasis" Cancer Metastasis Rev. 26(2):333-339.

Chang & Werb (2001) "The Many Faces of Metalloproteases: Cell Growth, Invasion, Angiogenesis and Metastasis" Trends Cell. Biol. 11(11):537-43.

Chang, et al. (2004) "Gene expression signature of fibroblast serum response predicts human cancer progression: similarities between tumors and wounds" PLoS Biol. 2(2):206-213.

Chanoki, et al. (1995) "Increased Expression of Lysyl Oxidase in Skin with Scleroderma" Br. J. Dermatol. 133(5):710-5.

Chichester, et al. (1981). "Lung lysyl oxidase and prolyl hydroxylase: increases induced by cadmium chloride inhalation and the effect of β-aminopropionitrile in rats." Am Rev Respir Dis 124(6): 709-13.

Chioza, et al. (2001). "Mutations in the lysyl oxidase gene are not associated with amyotrophic lateral sclerosis." Amyotroph Lateral Scler Other Motor Neuron Disord 2(2): 93-7.

Chow, et al. "Identification and Expression of an Allergen Asp f 13 from *Aspergillus fumigatus* and Epitope Mapping Using Human IgE Antibodies and Rabbit Polyclonal Antibodies," Biochem. J, 2000, vol. 346, pp. 423-431.

Christiansen & Rajasekaran (2006) "Reassessing Epithelial to Mesenchymal Transition as a Prerequisite for Carcinoma Invasion and Metastasis" Cancer Res., 66(17):8319-26.

Christiansen, et al. (2004) "Biological Impediments to Monoclonal Antibody-Based Cancer Immunotherapy" Mol. Cancer Ther. 3(11):1493-1501.
Chu & Peters (2008). "Serial analysis of the vascular endothelial transcriptome under static and shear stress conditions." Physiol Genomics 34(2): 185-92.
Chu, et al. (2008). "Glycogen synthase kinase-3β regulates DeltaNp63 gene transcription through the β-catenin signaling pathway." J Cell Biochem 105(2): 447-53.
Colman (1994) "Effects of Amino Acid Sequence Changes on Antibody-Antigen Interactions" Res. Immunol. 145(1):33-36.
Conti, et al. (2008). "The desmoplastic reaction surrounding hepatic colorectal adenocarcinoma metastases aids tumor growth and survival via alphav integrin ligation." Clin Cancer Res 14(20): 6405-13.
Csiszar, et al. (1996). "Functional analysis of the promoter and first intron of the human lysyl oxidase gene." Mol Biol Rep 23(2): 97-108.
Csiszar, et al. (2002) "Somatic Mutation of the Lysyl Oxidase Gene on Chromosome 5q23.1 in Colorectal Tumors" Int. J. Cancer 97(5):636-642.
Database GENESEQ (Derwent, London, UK), Accession No. A 13B07649, Feb. 14, 2002, 99.9% identical to SEQ ID No. 2.
Database Issued Patents (United States Patent & Trademark Office, Alexandria, VA) US Patent No. 6,300,092. Oct. 9, 2001 99.9% identical to SEQ ID No. 2.
Decitre, et al. (1998) "Lysyl oxidase-like protein localizes to sites of de novo fibrinogenesis in fibrosis and in the early stromal reaction of ductal breast carcinomas" Lab. Invest. 78(2):143-151.
Denko, et al. (2003) "Investigating Hypoxic Tumor Physiology through Gene Expression Patterns" Oncogene 22:5907-5914.
Dermer (1994) "Another Anniversary for the War on Cancer" Biotechnology 12:320.
Dillman, (1989) "Monoclonal antibodies for treating cancer" Ann. Intern. Med. 111(7):592-603.
Entrez Gene data base searching result in National Library of Medicine. 2010.
Erler & Giaccia (2006). "Lysyl oxidase mediates hypoxic control of metastasis." Cancer Res 66(21): 10238-41.
Erler, et al. (2004) "627 The role of Hypoxia-Induced Lysyl Oxidase in Cancer Progression, Tumor Response to Therapy and Patient Prognosis" Eur. J. Cancer Suppl. 2(8):190.
Erler, et al. (2004) "Lysyl Oxidase is Essential for Hypoxia-Induced Metastasis" Pro. Amer. Assoc. Cancer Res. 47:570.
Erler, et al. (2005) "Hypoxia promotes invasion and metastasis of breast cancer cells by increasing lysyl oxidase expression" Breast Cancer Res. 7 (Suppl 2):P5.05.
Erler, et al. (2006) "12 LOX is Essential for Hypoxia-Induced Metastasis" Radiother. Oncol. 78:S5.
Erler, et al. (2006) "Lysyl Oxidase is Essential for Hypoxia-Induced Metastasis" Nature 440(7088):1222-1226.
Erler, et al. (2009). "Hypoxia-induced lysyl oxidase is a Critical mediator of bone marrow cell recruitment to form the premetastatic niche." Cancer Cell 15(1): 35-44.
Evans et al. (1999) "Vaccine Therapy for Cancer—Fact or Fiction?" QJM. 92(6):299-307.
Example from Wikipedia, the free encyclopedia, "Monoclonal Antibody Therapy," (http://en.wikipedia.org/wiki/Antibody_therapy), accessed on Oct. 4, 2010.
Example of the USPTO's Written Description Training Materials, Revision 1, Mar. 25, 2008, 84 pages in length.
Ferrari, et al. (1991) "Identification of Immunodominant T Cell Epitopes of the Hepatitis B Virus Nucleocapsid Antigen" J. Clin. Invest. 88(1):214-222.
Fidler, et al. (1994) "The implications of angiogenesis for the biology and therapy of cancer metastasis" Cell 79(2):185-188.
Fodstad, et al. (1988) "A New Experimental Metastasis Model in Athymic Nude Mice, the Human Malignant Melanoma Lox" Intl. J. Cancer 41:442-449.A216.
Fogelgren, et al. (2005) "Cellular fibronectin binds to lysyl oxidase with high affinity and is critical for its proteolytic activation" J Biol. Chem. 280(26):24690-24697.
Fong, et al. (2007) "Lysyl oxidase-like 2 expression is increased in colon and esophageal tumors and associated with less differentiated colon tumors" Genes, Chromosomes and Cancer vol. 46(7):644-655.

Freshney (1983) Culture of Animal Cells: A Manual of Basic Technique, Alan R. Liss Inc.: NY:4.
Gacheru, et al. (1997). "Transcriptional and post-transcriptional control of lysyl oxidase expression in vascular smooth muscle cells: effects of TGF-β1 and serum deprivation." J Cell Biochem 65(3): 395-407.
Giampuzzi, et al. (2001) "Down-Regulation Oflysyloxidase-Induced Tumorigenic Transformation in NRK-49F Cells Characterized by Constitutive Activation of Ras Proto-Oncogene" J Biol. Chem. 276(31):29226-29232.
Görögh, et al. (2008). "Functional analysis of the 5' flanking domain of the LOXL4 gene in head and neck squamous cell carcinoma cells." Int J Oncol 33(5): 1091-8.
Grant & Dent (2001) "Overview: Rational Integration of Agents Directed at Novel Therapeutic Targets into Combination Chemotherapeutic Regimens" Curr. Opin. Investig Drugs 2(11):1600-1605.
Gross, et al. (2001)"Idiopathic Pulmonary Fibrosis" N. Engl. J. Med. 345(7):517-525.
Gura (1997) "Systems for Identifying New Drugs Are Often Faulty" Science 278(5347):1041-1042.
Ham, et al. (2008) "144. Inhibition of an Extracellular Matrix Protein Increases Survival in Orthotopic Nude Mouse Models" J. Surg. Res. 144(2):239-240.
Harrison & Lazo (1987) "High Dose Continuous Infusion of Bleomycin in Mice: A New Model for Drug-Induced Pulmonary Fibrosis" J. Pharmacol. Exp. Ther. 243(3):1185-1194.
Hayashi, et al. (2004). "Comparative immunocytochemical localization of lysyl oxidase (LOX) and the lysyl oxidase-like (LOXL) proteins: changes in the expression of LOXL during development and growth of mouse tissues." J Mol Histol 35(8-9): 845-55.
Hein, et al. (2001). "Lysyl oxidases: expression in the fetal membranes and placenta." Placenta 22(1): 49-57.
Herrington et al., Principles and basic methodology of DNA/RNA detection by in situ hybridization. Chapter 4, pp. 69-102, Diagnostic Molecular Pathology vol. 1, Phenotyping and genotyping of intact cells, IRL Press, Oxford University Press, 1992.
Higgins, et al. (2007) "Hypoxia promotes a fibrogenesis in vivo via HIF-1 stimulation of epithelial-to-mesenchymal transition" Journal Clinical Investigation 117(12):3810-20.
Hockel, et al. (2001) "Tumor Hypoxia: Definitions and Current Clinical, Biologic and Molecular Aspects" Journal of the National Cancer Institute. 93(4):266-276.
Hollosi, et al. (2009). "Lysyl oxidase-like 2 promotes migration in noninvasive breast cancer cells but not in normal breast epithelial cells." Int J Cancer 125(2):318-327.
Jain (1994) "Barriers to Drug Delivery in Solid Tumors" Scientific American 271(1):58-65.
Jansen & Csiszar (2007). "Intracellular localization of the matrix enzyme lysyl oxidase in polarized epithelial cells." Matrix Biol 26(2): 136-9.
Jansen, et al. (2006) "Lysyl oxidase regulates kidney epithelial cell phenotype" ASMB Meeting Abstrat/Matrix Biology 25:S92.
Jourdan-Le Saux, et al. (1998). "The human lysyl oxidase-related gene (LOXL2) maps between markers D8S280 and D8S278 on chromosome 8p21.2-p21.3." Genomics 51(2): 305-7.
Jourdan-Le Saux, et al. (2000). "The mouse lysyl oxidase-like 2 gene (mLOXL2) maps to chromosome 14 and is highly expressed in skin, lung and thymus." Matrix Biol 19(2): 179-83.
Jung, et al. (2003). "Purification of enzymatically active human lysyl oxidase and lysyl oxidase-like protein from Escherichia coli inclusion bodies." Protein Expr Purif 31(2): 240-6.
Kagan, et al. (1995) "Expression of Lysyl Oxidase from cDNA Constructs in Mammalian Cells: The Propeptide Region Is Not Essential to the Folding and Secretion of the Functional Enzyme" J. Cell Biochem. 59(3):329-38.
Kagan, et al. (1995). "Catalytic properties and structural components of lysyl oxidase." Novartis Foundation Symp. 192: 100-15; discussion 115-21.
Kagan, H.M. (2000) "Intra-and Extracellular Enzymes of Collagen Biosynthesis as Biological and Chemical Targets in the Control of Fibrosis" Acta Tropica 77(1):147-152.

Kaku, et al. (2007). "Post-translational modifications of collagen upon BMP-induced osteoblast differentiation." Biochem Biophys Res Commun 359(3): 463-8.

Kaneda et al. (2004) "Lysyl Oxidase is a Tumor Suppressor Gene Inactivated by Methylation and Loss of Heterozygosity in Human Gastric Cancers" Cancer Res. 64(18):6410-6415.

Kang, et al. "Prosaposin Inhibits Tumor Metastasis Via Paracrine and Endocrine Stimulation of Stromal p53 and Tsp-1" Proc. Natl. Acad. Sci. U.S.A. 106(29):12115-12120. (2009).

Kenyon, et al. (1991) "Lysyl Oxidase and rrg Messenger RNA" Science 253:802.

Kenyon, et al. (2003) "TGF-[beta]1 Causes Airway Fibrosis and Increased Collagen I and III mRNA in Mice" Thorax 58(9):772-777.

Khakoo, et al. (1997) "Congenital Cutis Laxa and Lysyl Oxidase Deficiency" Clin. Genet. 51(2):109-14.

Kim, et al. (1997). "A highly polymorphic (CA) repeat sequence in the human lysyl oxidase-like gene." Clin Genet 51(2): 131-2.

Kirschmann, et al. (1999) "Differentially expressed genes associated with the metastatic phenotype in breast cancer" Breast Cancer Res Treat. 55(2):127-136.

Klutke, et al. (2008). "Decreased endopelvic fascia elastin content in uterine prolapse." Acta Obstet Gynecol Scand 87(1): 111-5.

Krebs & Krawetz (1993) "Lysyl Oxidase Copper-Talon Complex: A Model" Biochim. Biophys. Acta 1202(1):7-12.

Kresse, et al. (2008). "DNA copy number changes in high-grade malignant peripheral nerve sheath tumors by array CGH." Mol Cancer 7: 48.

Laczko, et al. (2007). "Active lysyl oxidase (LOX) correlates with focal adhesion kinase (FAK)/paxillin activation and migration in invasive astrocytes." Neuropathol Appl Neurobiol 33(6): 631-43.

Le et al. (2007) "Expression and Prognostic Significance of a Panel of Tissue Hypoxia Markers in Head-and-Neck Squamous Cell Carcinoma," Int. J. Radiation Oncology Biol. Phys. 69(1):157-175.

Lelievre, et al. (2008). "VE-statin/egfl7 regulates vascular elastogenesis by interacting with lysyl oxidases." EMBO J 27(12): 1658-70.

Levene et al. (1985) "Possibilities for the Therapeutic Control of Fibrosis," Br. J. Dermatol. 112(3):363-371.

Li, et al. (2007). "Tumor microenvironment: the role of the tumor stroma in cancer." J Cell Biochem 101(4): 805-15.

Lucero & Kagan (2006). "Lysyl oxidase: an oxidative enzyme and effector of cell function." Cell Mol Life Sci 63(19-20): 2304-16.

Luo, et al. (1998) "Differential Inhibition of Fluid Accumulation and Tumor Growth in Two Mouse Ascites Tumors by an Antivascular Endothelial Growth Factor/Permeability Factor Neutralizing Antibody" Cancer Res. 58(12):2594-2600.

Luo, et al. "Significant expression of vascular endothelial growth factor/vascular permeability factor in mouse ascites tumors" Cancer Res., 1998, vol. 58, No. 12, pp. 2652-2660.

Macartney-Coxson, et al. (2008). "Metastatic susceptibility locus, an 8p hot-spot for tumour progression disrupted in colorectal liver metastases: 13 candidate genes examined at the DNA, mRNA and protein level." BMC Cancer 8: 187.

Madakamutil, et al. "Immunodominance in the TCR Repertoire of α TCR Peptide-Specific CD4+ Treg Population that Controls Experimental Autoimmune Encephalomyelitis" J. Immunology 2008, vol. 180, pp. 4577-4585.

Mäki, et al. (2001). "Cloning and characterization of a fifth human lysyl oxidase isoenzyme: the third member of the lysyl oxidase-related subfamily with four scavenger receptor cysteine-rich domains." Matrix Biol 20(7): 493-6.

Mattioli, et al. "Mimicry of the Immunodominant Conformation-Dependent Antigenic Site of Hepatitis A Virus by Motifs Selected from Synthetic Peptide Libraries" Journal of Virology, Sep. 1995, vol. 69, No. 9, pp. 5294-5299.

Mbeunkui, et al. (2007) "Identification of differentially secreted biomarkers using LC-MS/MS in isogenic cell lines representing a progression of breast cancer" Journal Proteome Res. 6:2993-3002.

Molnar, et al. (2005). "*Drosophila* lysyl oxidases Dmloxl-1 and Dmloxl-2 are differentially expressed and the active DmLOXL-1 influences gene expression and development." J Biol Chem 280(24): 22977-85.

Monticone, et al. (2004). "Gene expression profile of human bone marrow stromal cells determined by restriction fragment differential display analysis." J Cell Biochem 92(4): 733-44.

Müller, et al. (2006). "Lung fibroblasts from patients with emphysema show markers of senescence in vitro." Respir Res 7: 32.

Nagaoka, et al. (2008). "1,25(OH)2D3 regulates collagen quality in an osteoblastic cell culture system." Biochem Biophys Res Commun 377(2): 674-8.

Nakken, et al. (2007). "Multiple inflammatory-, tissue remodelling- and fibrosis genes are differentially transcribed in the livers of Abcb4 (–/–) mice harbouring chronic cholangitis." Scand J Gastroenterol 42(10): 1245-55.

National Cancer Institute; Staging: Questions and answers, www.cancer.gov/cancertopics/factsheet/detection/staging, Nov. 6, 2009.

Noblesse, et al. (2004) "Lsyl oxidase-like and lysysl oxidase are present in the dermis and epidermis of a skin equivalent and in himan skin and are associate to elastic fibers" J. Investig. Dermatol., 122:621-630.

Norrby (2006) "In vivo models of angiogenesis" *J. Cell. Mol. Med.* 10(3):588-612.

Ooshima & Midorikawa (1977) "Increased lysyl Oxidase Activity in Blood Vessels of Hypertensive Rats and Effect of beta-Aminopropionitrile on Arteriosclerosis" Jpn. Circ. J. 41(12):1337-40.

Orimo & Weinberg (2006). "Stromal fibroblasts in cancer: a novel tumor-promoting cell type." Cell Cycle 5(15): 1597-601.

Orimo, et al. (2001). "Cancer-associated myofibroblasts possess various factors to promote endometrial tumor progression." Clin Cancer Res 7(10): 3097-105.

Palamakumbura, et al. (2004) "The Propeptide Domain of Lysyl Oxidase Induces Phenotypic Reversion of Ras-Transformed cells" J. Biol. Chem. 279(39):40593-40600.

Panchenko, et al. (1996) "Metalloproteinase activity secreted by fibrogenic cells in the processing of prolysyl oxidase Potential Role of Procollagen C-Proteinase" J Biol Chem. 271(12):7113-7119.

Pascal, et al. (2005). "Comparison of replicative senescence and stress-induced premature senescence combining differential display and low-density DNA arrays." FEBS Lett 579(17): 3651-9.

Paul (1993) Fundamental Immunology, 3rd Ed., Raven Press: NY:292-295.

Payne, et al. (2005) "Lysyl oxidase regulates breast cancer cell migration and adhesion through a hydrogen peroxide-mediated mechanism" Cancer Res. 65(24):11429-11436.

Payne, et al. (2007). "Paradoxical roles for lysyl oxidases in cancer—a prospect." J Cell Biochem 101(6): 1338-54.

Peinado, et al. (2005) "A Molecular Role for Lysyl Oxidase-Like 2 Enzyme in Snail Regulation and Tumor Progression" EMBO J. 24(19):3446-3458.

Peinado, et al. (2005). "Switching on-off Snail: LOXL2 versus GSK3β." Cell Cycle 4(12): 1749-52.

Peinado, et al. (2008) "Lysyl Oxidase-like 2 as a New Poor Prognosis Marker of Squamous Cell Carcinomas" Cancer Research 68(12):4541-4550.

Peyrol, et al. (1997) "Lysyl oxidase gene expression in the stromal reaction to in situ and invasive ductal breast carcinoma" Am J. Pathol. 150(2):497-507.

Pinnell (1982) "Molecular Defects in the Ehlers-Danlos Syndrome" J. Invest. Dermatol. 79(Supp 1):90S-92S.

Pires Martins, et al. (2001). "Whole-body gene expression by data mining." Genomics 72(1): 34-42.

Polgar, et al. (2007). "Lysyl oxidase interacts with hormone placental lactogen and synergistically promotes breast epithelial cell proliferation and migration." J Biol Chem 282(5): 3262-72.

Postlethwaite, et al. (1987) "Stimulation of the chemotactic migration of human fibroblasts by transforming growth factor β" J. Exp. Med. 165(1):251-256.

Postovit, et al. (2008). "Hypoxia/reoxygenation: a dynamic regulator of lysyl oxidase-facilitated breast cancer migration." J Cell Biochem 103(5): 1369-78.

Pouysségur, et al. (2006) "Hypoxia Signalling in Cancer and Approaches to Enforce Tumour Regression" Nature 441(7092):437-443.

R&D Systems. Ordering Information: Catalog No. MAB2639. Anti-human lysyl oxidase homolog 2 monoclonal antibody. Apr. 18, 2005.

Radisky, et al. (2001) "Tumors Are Unique Organs Defined by Abnormal Signaling and Context" Semin. Cancer Bio. 11(2):87-95.

Rakic et al. (2003) "Placental Growth Factor, a Member of the VEGF Family, Contributes to the Development of Choroidal Neovascularization" Invest. Ophthalmol. Vis. Sci. 44(7):3186-3193.

Ren, et al. (1998) "Reduced lysyl oxidase messenger RNA levels in experimental and human prostate cancer" Cancer Res. 58:1285-1290.

Resnick, et al. (1994) "The SRCR Superfamily: A Family Reminiscent of the Ig Superfamily" Trends Biochem. Sci. 19(1):5-8.

Riechmann, et al. (1988) "Reshaping Human Antibodies for Therapy" Nature 332(6162):323-327.

Rodriguez et al. (2010) "Modulation of lysyl oxidase-like 2 enzymatic activity by an allosteric antibody inhibitor" J. Biol. Chem. 285:20964-20974.

Rodriguez, et al. (2008) Regulation of lysyl oxidase in vascular cells: lysyl oxidase as a new player in cardiovascular diseases. Cardiovasc Res. 79(1):7-13.

Rost, et al. (2003) "Reduction of LOX- and LOXL2-mRNA expression in head and neck squamous cell carcinomas" Anticancer Res. 23(2B):1565-1573.

Royce, et al. (1980) "Reduced Lysyl Oxidase Activity in Skin Fibroblasts from Patients with Menkes' Syndrome" Biochem. J. 192(2):579-86.

Rozalski, et al. "Epitope Specificities of Murine Monoclonal and Rabbit Polyclonal Antibodies against Enterobacterial Lipopolysaccharides of the Re Chemotype" Infection and Immunity, Sep. 1989, vol. 57, No. 9, pp. 2645-2652.

Rudikoff, et al. (1982) "Single Amino Acid Substitution Altering Antigen-Binding Specificity" PNAS USA 79(6):1979-1983.

Saito, et al. (1997) "Regulation of a novel gene encoding a lysyl o5cidase-related protein in cellular adhesion and senescence" J. Biol Chem. 272(13):8157-8160.

Salnikow, et al. (2008). "Regulation of hypoxia-inducible genes by ETS1 transcription factor." Carcinogenesis 29(8): 1493-9.

Sappino, et al. (1988) "Smooth-Muscle Differentiation in Stromal Cells of Malignant and Non-Malignant Breast Tissues" Int. J. Cancer 41(5):707-712. Abstract Only.

Satoh, et al. (2003) "Inhibition of local adhesion kinase by antisense oligonucleotides enhances the sensitivity of breast cancer cells to camptothecins" Biocell 27(1):47-55.

Schlotzer-Schrehardt, et al. (2008). "Genotype-correlated expression of lysyl oxidase-like 1 in ocular tissues of patients with pseudoexfoliation syndrome/glaucoma and normal patients." Am J Pathol 173(6): 1724-35.

Schmidt, et al. (2007). "[Mapping of a deletion interval on 8p21-22 in prostate cancer by gene dosage PCR]." Verh Dtsch Ges Pathol 91: 302-7.

Sebban, et al. (2009). "Lysyl oxidase-like 4 is alternatively spliced in an anatomic site-specific manner in tumors involving the serosal cavities." Virchows Arch 454(1): 71-9.

Selman, et al. (2006) "Gene Expression Profiles Distinguish Idiopathic Pulmonary Fibrosis from Hypersensitivity Pneumonitis" Am. J. Respir. Crit.Care Med. 173(2):188-198.

Sevil, et al. (1996) "Pharmacokinetic Analysis of Beta-Aminopropionitrile in Rabbits" Vet Res. 27(2):117-123 (Abstract only).

Sheppard (2006) "Transforming Growth Factor β: A Central Modulator of Pulmonary and Airway Inflammation and Fibrosis" Proc. Am. Thorac. Soc. 3(5):413-417.

Sheridan, et al. (1979) "Increased Lysyl Oxidase Activity in Aortas of Hypertensive Rats and Effect of Beta-Aminopropionitrile" Exp Mol Pathol. 30(2):315-324.

Shieh, et al. (2007) "Association of expression aberrances and genetic polymorphisms of lysyl oxidase with areca-associated oral tumorigenesis" Clinical Cancer Res. 13(15):4378-4385.

Siegers, et al. (1986) "Hepatoprotection by Malotilate against Carbon Tetrachloride-Alcohol Induced Liver Fibrosis" Inflammation Res. 18(5-6):600-603. Abstract Only.

Sion, et al. (2006) "Lysyl oxidase (lox) and hypoxia-induced metastases" Cancer Biology & Therapy, 5(8):909-911.

Sivakumar, et al. (2008) "Upregulation of Lysyl Oxidase and MMPs During Cardiac Remodeling in Human Dilated Cardiomyopathy" Mol Cell Biochem 307(1-2):159-167.

Smith-Mungo & Kagan (1998) "Lysyl Oxidase: Properties, Regulation and Multiple Functions in Biology" Matrix Biol. 16: 387-98.

Sommer, et al. (1993) "Transient expression of lysyl oxidase by liver myofibroblasts in murine schistosomiasis" Laboratory Investigation 69(4):460-470.

Sørensen, et al. (2007) "Hypoxia-induced Expression of Endogenous Markers in Vitro is Highly Influenced by pH" Radiotherapy and Oncology 83:362-366.

Stapleton, et al. "Neutralization Escape Mutants Define a Dominant Immunogenic Neutralization Site on Hepatitis A Virus" Journal of Virology, Feb. 1987, vol. 61, No. 2, pp. 491-498.

Stassar, et al. (2001) "Identification of Human renal cell carcinoma associated genes by suppression subtractive hybridization" Br. J. Cancer 85(9):1372-1382.

Szabo, et al. (1997). "The human lysyl oxidase-like gene maps between STS markers D15S215 and GHLC.GCT7C09 on chromosome 15." Hum Genet 101(2): 198-200.

Szauter, et al. (2005). "Lysyl oxidase in development, aging and pathologies of the skin." Pathol Biol (Paris) 53(7): 448-56.

Tamura, et al. (1998) "Inhibition of Cell Migration, Spreading, and Focal Adhesions by Tumor Suppressor PTEN" Science 280:1614-1618.

Tang, et al. (1983). "Reaction of aortic lysyl oxidase with β-aminopropionitrile." J Biol Chem 258(7): 4331-8.

Tang, et al. (1984). "β-substituted ethylamine derivatives as suicide inhibitors of lysyl oxidase." J Biol Chem 259(2): 975-9.

Tarp, et al. "Identification of a Novel Cancer-Specific Immunodominant Glycopeptide Epitope in the MUC1 Tandem Repeat" Glycobiology, 2007, vol. 17, No. 2, pp. 197-209.

Thiery, et al. (2003) "Epithelial-Mesenchymal Transitions in Development and Pathologies" Curr. Opin. Cell. Biol. 15(6):740-6.

Thomassin, et al. (2005) "The Pro-Regions of Lysyl Oxidase and Lysyl Oxidase-Like 1 Are Required for Deposition onto Elastic Fibers" J Biol. Chem. Dec. 30, 2005; 280(52):42848-55.

Tockman et al. (1992) "Consideration in Bringing a Cancer Biomarker to Clinical Application" Cancer Res. 52:2711s-2718s.

Topp, et al. (1998) "Antibody Transport in Cultured Tumor Cell Layers" J. Control. Release 53(1-3):15-23.

Trackman & Kagan (1979). "Nonpeptidyl amine inhibitors are substrates of lysyl oxidase." J Biol Chem 254(16): 7831-6.

Trackman, et al. (1991) "Cloning of rat aorta lysyl oxidase cDNA: Complete codons and predicted amino acid sequence" Biochem. 29(20)4863-4870 (1990 and Corrected Page: Biochem. 30(33):8282.

Trentham, et al. (1977) "Autoimmunity to Type II Collagen: An Experimental Model of Arthritis" J. Experimental Medicine 146:857-868.

Trivedy, et al. (1999) "The Upregulation of Lysyl Oxidase in Oral Submucous Fibrosis and Squamous Cell Carcinoma" J. Oral Pathol. Med. 28(6):246-251.

Understanding Cancer Series: Cancer Slide 8: Invasion and Metastasis, www.cancer.gov/cancertopics/understandingcancer/cancer/slide8.

Van Lancker, et al. (1995) "Patterns of axillary lymph node metastasis in breast cancer" Am. J. Clin. Oncol. 18(3):267-272.

Van Roy, et al. (1986) "Invasiveness and Metastatic Capability of Rat Fibroblast-like Cells before and after Transfection with Immortalizing and Transforming Genes" Cancer Res. 46:4787-4795.

Vautherot, et al. "Bovine Coronavirus Spike Glycoprotein: Localization of an Immunodominant Region at the Amino-Terminal End of S2" Journal of General Virology, 1992, vol. 73, pp. 3289-3294.

Waldmann (2003) "Immunotherapy: Past, Present and Future" Nat. Med. 9(3):269-277.

Walling, et al. (2004) "Agiessive basal cell carcinoma: Presentation, pathogenesis, and management" Cancer and Metastasis Reviews 23:389-402.

Walters & Kleeberger (2008) "Mouse Models of Bleomycin-Induced Pulmonary Fibrosis" Current Protocols Pharmacol. 40:5.46.1-5.46.17.

Wang, et al. (2007) "Lysyl Oxidase Inhibition Reduces Rat Liver Fibrosis after Bile Duct Ligation" Gastroenterology & Digestive Disease Week Meeting—108th Annual Meeting of the American-Gastroenterological-Association. Washington, DC. May 19-24, 2007; 132(4):A827.
Watters, et al. (1987) "Idiopathic Pulmonary Fibrosis. Pretreatment Bronchoalveolar Lavage Cellular Constituents and Their Relationships with Lung Histopathology and Clinical Response to Therapy" Am. Rev. Respir. Dis. 135(3):696-704. Abstract Only.
Weiner, (1999) "An Overview of Monoclonal Antibody Therapy of Cancer" Seminars Oncology 26(4):41-50.
Weise, et al. (2008). "LOXL4 is a selectively expressed candidate diagnostic antigen in head and neck cancer." Eur J Cancer 44(9): 1323-31.
Zhang, et al. (2007) "Hypoxia Enhances Metastatic Efficiency in HT-1060 Fibrosarcoma Cells by Increasing Cell Survival in Lungs Not Cell Adhesion and Invasion" Cancer Res. 67(18):7789-7797.
International Preliminary Report on Patentability for PCT/US2010/046192, mailed Feb. 21, 2012, 7 pages.
Aplin, et al. (1998) "Signal Transduction and Signal Modulation by Cell Adhesion Receptors: The Role of Integrins, Cadherins, Immunoglobulin-Cell Adhesion Molecules and Selectins" *Pharmacol. Rev.* 50(2):197-263.
GenBank Accession No. AAA59525.1 "Lysyl Oxidase [*Homo sapiens*]" dated Jan. 7, 1995.
GenBank Accession No. AAA59541.1 "Lysyl Oxidase [*Homo sapiens*]" dated Jan. 7, 1995.
GenBank Accession No. AAB21243.1 "Lysyl Oxidase [*Homo sapiens*]" dated May 7, 1993.
GenBank Accession No. AAB23549.1 "Lysyl Oxidase [*Homo sapiens*]" dated May 8, 1993.
GenBank Accession No. AAD02130.1 "Lysyl Oxidase [*Homo sapiens*]" dated May 6, 1999.
GenBank Accession No. AAH15090.1 "Lysyl Oxidase-Like 1 [*Homo sapiens*]" dated Oct. 4, 2001.
GenBank Accession No. AAH74820.1 "Lysyl Oxidase [*Homo sapiens*]" dated Jul. 7, 2004.
GenBank Accession No. AAH74872.1 "Lysyl Oxidase [*Homo sapiens*]" dated Aug. 4, 2004.
GenBank Accession No. AAK51671.1 "Lysyl Oxidase-Like 3 Protein [*Homo sapiens*]" dated May 9, 2001.
GenBank Accession No. AAK71934.1 "Lysyl Oxidase-Related Protein C [*Homo sapiens*]" dated Jul. 11, 2001.
GenBank Accession No. AF039291 "*Homo sapiens* Lysyl Oxidase mRNA, Complete cds" May 6, 1999.
GenBank Accession No. AF282619 "*Homo sapiens* Lysyl Oxidase-like 3 Protein mRNA, Complete cds" dated May 9, 2001.
GenBank Accession No. AF338441 "*Homo sapiens* Lysyl Oxidase-Related Protein C (LOXC) mRNA, Complete cds" dated Jul. 11, 2001.
GenBank Accession No. BC015090 "*Homo sapiens* Lysyl Oxidase-Like 1, mRNA (cDNA Clone MGC:16541 Image:4040510), Complete cds" dated Oct. 4, 2001.
GenBank Accession No. BC018439 "Mus Musculus Lysyl Oxidase, mRNA (cDNA Clone MGC:11525 Image:2655752), Complete cds" dated Dec. 6, 2001.
GenBank Accession No. BC074820 "*Homo sapiens* Lysyl Oxidase, mRNA (cDNA Clone MGC:104085 Image:30915536), Complete cds" dated Jul. 7, 2004.
GenBank Accession No. BC074872 "*Homo sapiens* Lysyl Oxidase, mRNA (cDNA Clone MGC:103851 Image:30915233), Complete cds" dated Jul. 7, 2004.
GenBank Accession No. M84150 "Human Lysyl Oxidase Gene, Partial cds" dated Jan. 7, 1995.
GenBank Accession No. M94054 "Human Lysyl Oxidase (LOX) mRNA, Complete cds" dated Jan. 7, 1995.
GenBank Accession No. NM_002317 "*Homo sapiens* Lysyl Oxidase (LOX), Transcript Variant 1, mRNA" dated Apr. 15, 2002.
GenBank Accession No. NM_033325 "Mus Musculus Lysyl Oxidase-Like 2 (Lox12), mRNA" dated Aug. 12, 2003.
GenBank Accession No. NP_002308 "Protein-Lysine 6-Oxidase Isoform 1 Preproprotein [*Homo sapiens*]" dated Apr. 15, 2002.
GenBank Accession No. NP_002309 "Lysyl Oxidase Homolog 2 Precursor [*Homo sapiens*]" dated Feb. 1, 2002.
GenBank Accession No. NP_005567 "Lysyl Oxidase Homolog 1 Preproprotein [*Homo sapiens*]" dated Nov. 5, 2002.
GenBank Accession No. NP_034858 "Protein-Lysine 6-Oxidase Precursor [Mus Musculus]" dated Jan. 7, 2002.
GenBank Accession No. NP_034859 "Lysyl Oxidase Homolog 1 Precursor [Mus Musculus]" dated Mar. 17, 2004.
GenBank Accession No. NP_115587 "Lysyl Oxidase Homolog 4 Precursor [*Homo sapiens*]" dated May 19, 2001.
GenBank Accession No. NP_115882 "AP-1 Complex Subunit mu-1 Isoform 2 [*Homo sapiens*]" dated May 27, 2001.
GenBank Accession No. NP_201582 "Lysyl Oxidase homolog 2 Precursor [Mus Musculus]" dated Aug. 12, 2003.
GenBank Accession No. 545875 "Lysyl Oxidase [Human, Skin Fibroblasts, mRNA Partial, 1254 nt]" May 8, 1993.
GenBank Accession No. 578694 "Lysyl Oxidase [Human, mRNA, 1780 nt]" dated May 7, 1993.
GenBank Accession No. U89942 "Human Lysyl Oxidase-Related Protein (WS9-14) mRNA, Complete cds" dated Aug. 18, 2003.
Kaiser, et al. "First Pass at Cancer Genome Reveals Complex Landscape" (2006) Science 313(5792):1370.
Office Action mailed Sep. 23, 2010 in U.S. Appl. No. 12/185,054 (A6-US1).
Office Action mailed Feb. 15, 2011 in U.S. Appl. No. 12/185,054 (A6-US1).
International Preliminary Report on Patentability Chapter I issued Feb. 2, 2010, in PCT/US2008/009354 (A6-WO).
Written Opinion of the ISA mailed Apr. 29, 2009, in PCT/US2008/009354.
International Search Report mailed Apr. 29, 2009, in PCT/US2008/009354.
Invitation to Pay Additional Fees mailed Jan. 14, 2009 (including Annex "Communication Relating to the Results of Partial International Search"), in PCT/US2008/009354.
Communication pursuant to Article 94(3) EPC dated Jun. 8, 2010, in EP 08795003.6-1222.
Communication pursuant to Article 94(3) EPC dated Jul. 19, 2011, in EP 08795003.6-1222.
Communication under Rule 71(3) EPC dated Jul. 23, 2012, in EP 08795003.6-1222.
Office Action mailed Jun. 29, 2007, in U.S. Appl. No. 10/536,440.
Office Action mailed Mar. 28, 2008, in U.S. Appl. No. 10/536,440.
Office Action mailed Nov. 14, 2008, in U.S. Appl. No. 10/536,440.
Office Action mailed Jun. 26, 2009, in U.S. Appl. No. 10/536,440.
Office Action mailed Dec. 30, 2009, in U.S. Appl. No. 10/536,440.
Office Action mailed Jun. 28, 2010, in U.S. Appl. No. 10/536,440.
Office Action mailed Jul. 5, 2011, in U.S. Appl. No. 10/536,440.
Office Action mailed May 14, 2010, in U.S. Appl. No. 12/571,167.
Office Action mailed Nov. 5, 2010, in U.S. Appl. No. 12/571,167.
Office Action mailed Mar. 24, 2011, in U.S. Appl. No. 12/571,167.
Office Action mailed Jul. 28, 2011, in U.S. Appl. No. 12/571,167.
International Preliminary Examination Report mailed Dec. 8, 2003, in PCT/IL01/00728.
Written Opinion mailed Jun. 6, 2003, in PCT/IL01/00728.
International Search Report mailed Dec. 17, 2002, in PCT/IL01/00728.
Invitation to Pay Additional Fees mailed May 23, 2002, in PCT/IL01/00728.
International Search Report mailed Jan. 5, 2006, in PCT/IL03/01008.
Invitation to Pay Additional Fees mailed Jun. 13, 2005, in PCT/IL03/01008.
European Search Report mailed Jul. 29, 2005, in EP 01958338.4-2406.
Communication pursuant to Article 96(2) EPC mailed Nov. 14, 2005, in EP 01958338.4-2406.
Communication pursuant to Article 96(2) EPC mailed Jun. 25, 2007, in EP 01958338.4-2406.
Communication pursuant to Article 94(3) EPC mailed Feb. 10, 2009, in EP 01958338.4-2406.
European Search Report mailed Feb. 29, 2008, in EP 03777136.7-1222.
Communication pursuant to Article 94(3) EPC mailed May 29, 2008, in EP 03777136.7-1222.

European Search Report mailed Dec. 21, 2009, in EP 08020754.1-2402.
European Search Opinion mailed Dec. 21, 2009, in EP 08020754.1-2402.
Communication pursuant to Article 94(3) EPC mailed Oct. 22, 2010, in EP 08020754.1-2402.
Communication pursuant to Article 94(3) EPC mailed Mar. 15, 2011, in EP 08020754.1-2402.
European Search Report mailed Jun. 3, 2009, in EP 08020752.5-1222.
European Search Opinion mailed Jun. 3, 2009, in EP 08020752.5-1222.
Communication pursuant to Article 94(3) EPC mailed Feb. 8, 2010, in EP 08020752.5-1222.
Communication pursuant to Article 94(3) EPC mailed Dec. 27, 2011, in EP 08020752.5-1222.
European Search Report mailed Jun. 3, 2009, in EP 08020753.3-1222.
European Search Opinion mailed Jun. 3, 2009, in EP 08020753.3-1222.
Communication pursuant to Article 94(3) EPC mailed Dec. 27, 2011, in EP 08020753.3-1222.
European Search Report mailed Jul. 13, 2011, in EP 10012458.5-2406.
European Search Opinion mailed Jul. 13, 2011, in EP 10012458.5-2406.
European Search Report mailed Jun. 27, 2011, in EP 10012457.7-2406.
European Search Opinion mailed Jun. 27, 2011, in EP 10012457.7-2406.
Office Action mailed Sep. 23, 2010, in U.S. Appl. No. 12/185,050.
Office Action mailed Feb. 15, 2011, in U.S. Appl. No. 12/185,050.
International Preliminary Report on Patentability Chapter I issued May 11, 2010, in PCT/US2008/072039.
Written Opinion of the ISA mailed Jan. 13, 2009, in PCT/US2008/072039.
International Search Report mailed Jan. 13, 2009, in PCT/US2008/072039.
Communication pursuant to Article 94(3) EPC mailed Jun. 8, 2010, in EP 08830207.0-1222.
Communication pursuant to Article 94(3) EPC mailed Jul. 20, 2011, in EP 08830207.0-1222.
Communication pursuant to Article 94(3) EPC mailed Jul. 4, 2012, in EP 08830207.0-1222.
Office Action mailed Jun. 14, 2011, in U.S. Appl. No. 12/652,687.
Office Action mailed Dec. 13, 2011, in U.S. Appl. No. 12/652,687.
Office Action mailed Mar. 30, 2012, in U.S. Appl. No. 12/652,687.
Advisory Action mailed Feb. 23, 2012, in U.S. Appl. No. 12/652,687.
Notice of Allowance mailed Sep. 18, 2012, in U.S. Appl. No. 12/652,687.
International Preliminary Report on Patentability Chapter I issued Jul. 12, 2011, in PCT/US2010/020159.
Written Opinion of the ISA mailed Sep. 9, 2010, in PCT/US2010/020159.
International Search Report mailed Sep. 9, 2010, in PCT/US2010/020159.
Office Action mailed Jan. 17, 2012, in U.S. Appl. No. 12/701,289.
Office Action mailed Jun. 15, 2012, in U.S. Appl. No. 12/701,289.
Office Action mailed Sep. 24, 2012, in U.S. Appl. No. 12/701,289.
Advisory Action mailed Aug. 30, 2012, in U.S. Appl. No. 12/701,289.
International Preliminary Report on Patentability Chapter I issued Aug. 9, 2011, in PCT/US2010/023359.
Written Opinion of the ISA mailed Apr. 15, 2010, in PCT/US2010/023359.
International Search Report mailed Apr. 15, 2010, in PCT/US2010/023359.
Written Opinion of the ISA mailed Feb. 17, 2011, in PCT/US2010/046192.
International Search Report mailed Feb. 17, 2011, in PCT/US2010/046192.
Invitation to Pay Additional Fees mailed Nov. 18, 2010, in PCT/US2010/046192.
Office Action mailed Jul. 13, 2012, in U.S. Appl. No. 12/860,838.
International Preliminary Report on Patentability Chapter I issued Feb. 21, 2012, in PCT/US2010/046248.
Written Opinion of the ISA mailed Jan. 7, 2011, in PCT/US2010/046248.
International Search Report mailed Jan. 7, 2011, in PCT/US2010/046248.
Office Action mailed Jul. 12, 2012, in U.S. Appl. No. 12/860,693.
International Preliminary Report on Patentability Chapter I issued Feb. 21, 2012, in PCT/US2010/046196.
Written Opinion of the ISA mailed Oct. 1, 2010, in PCT/US2010/046196.
International Search Report mailed Oct. 1, 2010, in PCT/US2010/046196.
Office Action mailed May 29, 2012, in U.S. Appl. No. 12/860,632.
Office Action mailed Sep. 11, 2012, in U.S. Appl. No. 12/860,632.
International Preliminary Report on Patentability Chapter I issued Feb. 21, 2012, in PCT/US2010/046247.
Written Opinion of the ISA mailed Sep. 24, 2010, in PCT/US2010/046247.
International Search Report mailed Sep. 24, 2010, in PCT/US2010/046247.
Office Action mailed Dec. 22, 2011, in U.S. Appl. No. 12/892,574.
Office Action mailed Jun. 18, 2012, in U.S. Appl. No. 12/892,574.
Office Action mailed Aug. 31, 2012, in U.S. Appl. No. 12/892,574.
International Preliminary Report on Patentability Chapter I issued Apr. 3, 2012, in PCT/US2010/050542.
Written Opinion of the ISA mailed Nov. 29, 2010, in PCT/US2010/050542.
International Search Report mailed Nov. 29, 2010, in PCT/US2010/050542.
International Preliminary Report on Patentability Chapter I issued Aug. 7, 2012, in PCT/US2011/023791.
Written Opinion of the ISA mailed May 17, 2011, in PCT/US2011/023791.
International Search Report mailed May 17, 2011, in PCT/US2011/023791.
International Preliminary Report on Patentability Chapter I issued Feb. 21, 2012, in PCT/US2010/046244.
Written Opinion of the ISA mailed Feb. 8, 2011, in PCT/US2010/046244.
International Search Report mailed Feb. 8, 2011, in PCT/US2010/046244.
Invitation to Pay Additional Fees mailed Dec. 3, 2010, in PCT/US2010/046244.
Written Opinion of the ISA mailed Jun. 14, 2012, in PCT/US2012/032600.
International Search Report mailed Jun. 14, 2012, in PCT/US2012/032600.
Written Opinion of the ISA mailed Aug. 10, 2012, in PCT/US2012/037580.
International Search Report mailed Aug. 10, 2012, in PCT/US2012/037580.
Written Opinion of the ISA mailed Sep. 10, 2012, in PCT/US2012/040585.
International Search Report mailed Sep. 10, 2012, in PCT/US2012/040585.
Akhtar et al. (2002) "The sponge/Matrigel angiogenesis assay" Angiogenesis 5(1-2):75-80.
Albini et al. (2004) "The chemoinvasion assay: a tool to study tumor and endothelial cell invasion of basement membranes," Int. J. Dev. Biol. 48:563-571.
Armstrong et al. (1999) "Changes in Collagen Turnover in Early Acute Respiratory Distress Syndrome," Am. J. Respir. Crit. Care Med. 160:1910-1915.
Bedogni et al. (2004) "Topical treatment with inhibitors of the phosphatidylinositol 3'-kinase/Akt and Raf/mitogen-activated protein kinase kinase/extracellular signal-regulated kinase pathways reduces melanoma development in severe combined immunodeficient mice" Cancer Res. 64(7):2552-2560.
Beilmann et al. (2004) "Human primary co-culture angiogenesis assay reveals additive stimulation and different angiogenic properties of VEGF and HGF" Cytokine 26(4):178-185.

Berger et al. (2004) "A murine model of ex vivo angiogenesis using aortic disks grown in fibrin clot" Microvascular Res. 68(3):179-187.
Blacher et al. (2001) "Improved quantification of angiogenesis in the rat aortic ring assay" Angiogenesis 4(2):133-142.
BLAST 2 Sequences (LOR-1 and LOR-2) results version BLASTP 2.2.14, Apr. 9, 2006.
Brown et al. (1996) "A novel in vitro assay for human angiogenesis" Laboratory Investigation 75(4):539-555.
Castera (2011) "Invasive and Non-Invasive Methods for the Assessment of Fibrosis and Disease Progression in Chronic Liver Disease," Best Pract. Res. Clin. Gastroent. 25:291-303.
Chen (2005) "Boyden chamber assay" Methods Mol. Biol. 294:15-22.
Chua et al. (2005) "Pulmonary Fibrosis Searching for Model Answers," Am J. Respir. Cell. Mol. Biol. 33:9-13.
Database EMBL [Online] Oct. 28, 2008, "Sequence 15133 from Patent WO2004061423", retrieved from EBI accession No. EMBL:FB530075, Database accession No. FB530075.
De Eguileor et al. (2004) "Hirudo medicinalis: avascular tissues for clear-cut angiogenesis studies?" Current Pharmaceutical Design 10(16)1 979-1998.
Gelatt (1977) "Animal models for glaucoma" Invest. Ophthalmol. Visual Sci. 16(7):592-596.
Grigorescu (2006) "Noninvasive Biochemical Markers of Liver Fibrosis," J. Gastrointestin. Liver Dis. 15(2):149-159.
Go et al. (2003) "The rat aortic ring assay for in vitro study of angiogenesis" Methods Mol. Med. 85:59-64.
González-Iriate et al. (2003) "A modified chorioallantoic membrane assay allows for specific detection of endothelial apoptosis induced by antiangiogenic substances" Angiogenesis 6(3):251-254.
Greenbaum et al. (2003) "Comparing protein abundance and mRNA expression levels on a genomic scale", Genome Biology 40 (9):117.01-117.08.
Guedez et al. (2003) "Quantitative assessment of angiogenic responses by the directed in vivo angiogenesis assay" Am. J. Pathol. 162(5):1431-1439.
Gulec et al. (2004) "A new in vitro assay for human tumor angiogenesis: three-dimensional human tumor angiogenesis assay" Ann. Surgical Oncology 11(1):99-104.
Hartwell (1998) "Angiogenesis in P- and E-selectin-deficient mice" Microcirculation 5(2-3):173-178.
Ishak et al. (1995) "Histological Grading and Staging of Chronic Hepatitis," J. Hepatol. 22:696-699.
Jakobsson et al. (1994) "A Morphometric Method to Evaluate Angiogenesis Kinetics in the Rat Mesentry" Intl. J. Exp. Pathol. 75(3):214-219.
Julien et al. (2008) "A reproducible and quantifiable model of choroidal neovascularization induced by VEGF A after subretinal adenoviral gene transfer in the rabbit" Molecular Vision 14: 1358-1372.
Knodell et al. (1981) "Formulation and Application of a Numerical Scoring System for Assessing Histological Activity in Asymptomatic Chronic Active Hepatitis," Hepatol. 1(5):431-435.
Kragh et al. (2003) "In vivo chamber angiogenesis assay: an optimized Matrigel plug assay for fast assessment of anti-angiogenic activity" Intl. J. Oncology 22(2):305-311.
Kragh et al. (2004) "A versatile in vivo chamber angiogenesis assay for measuring antiangiogenic activity in mice" Oncology Reports 11(2):303-307.
Li et al. (1999) "Liver Fibrogenesis and the Role of Hepatic Stellate Cells: New Insights and Prospects for Therapy," J. of Gastroentero. and Hepatol. 14:618-633.
Lichtenberg et al. (1999) "The rat Subcutaneous Air Sac model: a quantitative assay of antiangiogenesis in induced vessels" Am. J. Pharmacol. Toxicology 84(1):34-40.
Lugassy, et al. (2012) "The Enzymatic Activity of Lysyl Oxidase-like-2 (LOXL2) is Not Required for LOXL2-induced Inhibition of Keratinocyte Differentiation", Journal of Biological Chemistry 287(5):3541-3549.
Maier et al. (2009) "Correlation of mRNA and protein in complex biological samples", FEBS Letters 583 (24):3966-3973.
Manns et al. (2011) "A Phase-2B Trial to Evaluate the Safety, Tolerability and Efficacy of a Caspase Inhibitor, GS-9450, in Adults Failing PEG/RBV Therapy for Chronic HCV Infection," J Hepatology. (2011) 54 Supplement 1: S55-S56.
Masson et al. (2002) "Mouse Aortic Ring Assay: A New Approach of the Molecular Genetics of Angiogenesis" Biol. Proc. Online 4:24-31.
McKechnie et al. (2003) "Hr44 Secreted wtih exosomes: Loss from Ciliary epithelium in response to inflammation" IOVS 44(6): 2650-2656.
Mehal et al. (2011) "Expressway to the Core of Fibrosis," Nat. Med. 17(5):552-553.
Miller et al. (2004) "A novel technique for quantifying changes in vascular density, endothelial cell proliferation and protein expression in response to modulators of angiogenesis using the chick chorioallantoic membrane (CAM) assay" J. Translational Med. 2(1):4.
Morbidelli et al. (2004) "The rabbit corneal pocket assay for the study of angiogenesis" Cancer Treatment Res. 117:147-151.
NCBI dbSNP record for LOXL2, available at http://www.ncbi.nlm.nih.gov/projects/SNP/snp_ref.cqi?locusId=4017, retrived Apr. 19, 2012.
Nehls et al. (1995) "A novel, microcarrier-based in vitro assay for rapid and reliable quantification of three-dimensional cell migration and angiogenesis" Microvascular Res. 50(3):311-322.
Nguyen et al. (1994) "Quantitation of angiogenesis and antiangiogenesis in the chick embryo chorioallantoic membrane" Microvascular Res. 47(1):31-40.
Nicosia et al. (1990) "Growth of microvessels in serum-free matrix culture of rat aorta. A quantitative assay of angiogenesis in vitro" Laboratory Investig. 63(1):115-122.
Nissanov et al. (1995) "Automatic vessel segmentation and quantification of the rat aortic ring assay of angiogenesis" Laboratory Investig. 73(5):734-739.
Norrby (1992) "On the quantitative rat mesenteric-window angiogenesis assay" EXS 61:282-286.
Okada et al. (1995) "A quantative in vivo method of analyzing human tumor-induced angiogenesis in mice using agarose microencapsulation and hemoglobin enzyme-linked immunosorbent assay" Japan. J. Cancer Res. 86(12):1182-1188.
Ogata et al. (1996) "Changes in alveolar capilary formation in growing rat lung by repeated injections of a lathyrogen" Growth, Development and Aging 60:153-160.
Parsons-Wingerter et al. (2000) "Fibroblast growth factor-2 selectively stimulates angiogenesis of small vessels in arterial tree" Arteriosclerosis Thrombosis Vasc. Biol. 20(5):1250-1256.
Presta et al. (1999) "Purine analogue 6-methylmercaptopurine riboside inhibits early and late phases of the angiogenesis process" Cancer Res. 59(10):2417-2424.
Reed et al. (2007) "Culture of murine aortic explants in 3-dimensional extracellular matrix: a novel, miniaturized assay of angiogenesis in vitro" Microvascular Res. 73(3):248-252.
Ribatti (2004) "The first evidence of the tumor-induced angiogenesis in vivo by using the chorioallantoic membrane assay dated 1913" Leukemia 18(8):1350-1351.
Ribatti et al. (1996) "The chick embryo chorioallantoic membrane as a model for in vivo research on angiogenesis" Intl. J. Devel. Biol. 40(6):1189-1197.
Ribatti et al. (1997) "New model for the study of angiogenesis and antiangiogenesis in the chick embryo chorioallantoic membrane: the gelatin sponge/chorioallantoic membrane assay" J. Vascular Res. 34(6):455-463.
Ribatti et al. (2000) "The Chick Embryo Chorioallantoic Membrane as a Model for In Vivo Research on Anti-Angiogenesis" Curr. Pharmacol. Biotechnol. 1(1):73-82.
Richardson et al. (2003) "Observations on the use of the avian chorioallantoic membrane (CAM) model in investigations into angiogenesis" Curr. Drug Targets Cardiovasc. Hematol. Disorders 3(2):155-185.
Roskoski (2007) "Vascular endothelial growth factor (VEGF) signaling in tumor progression" Critical Reviews in Oncology/Hematology 62: 179-213.
Ruckert et al. (2009) "Functional analysis of LOXL2 in pancreatic carcinoma" International Journal of Colorectal Disease ; Clinical and Molecular Gastroenterology and Surgery, Springer, Berlin, DE, 25(3):303-311.

Schena et al. (2005) "Pathogenic Mechanisms of Diabetic Nephropathy," J. Am. Soc. Nephrol. 16:S30-S33.

Scheuer (1991) "Classification of Chronic Viral Hepatitis: A Need for Reassessment," J. Hepatol. 13:372-374.

Sequence search result (Neufeld) 2010.

Siemann et al. "Tumor Vasculature: a Target for Anticancer Therapies" in: "Vascular-Targeted Therapies in Oncology", Mar. 10, 2006, John Wiley & Sons. Ltd. Chichester, UK.

Stiffey-Wilusz et al. (2001) "An ex vivo angiogenesis assay utilizing commercial porcine carotid artery: modification of the rat aortic ring assay" Angiogenesis 4(1):3-9.

Tzortzaki et al. (2006) "Active Remodeling in Idiopathic Interstitial Pneumonias: Evaluation of Collagen Types XII and XIV," J. Histochem. & Cytochem. 54(6):693-700.

Van Bergen et al. "The role of LOXa nd LOXL2 in wound healing after glaucoma filtration surgery", European association for vision and eye research, Oct. 8, 2010, Retrieved from the Internet: URL:http://www.ever.be/view_abstract.php?abs_id=5411.

Watanabe et al. (2010) "Nucleolin as cell surface receptor for tumor necrosis factor-alpha inducing protein: a carcinogenic factor of *Helicobacter pylori*", Journal of Cancer Research and Clinical Oncology 136(6):911-921.

Whaley-Connell et al. (2006) "Chronic Kidney Disease and the Cardiometabolic Syndrome," J. Clin. Hypert. 8(8):546-548.

Zhu et al. (2002) "The thin prep rat aortic ring assay: a modified method for the characterization of angiogenesis in whole mounts" Angiogenesis 5(1-2):81-86.

Portolano, et al. (1993). "Lack of Promiscuity in Autoantigen-Specific H and L Chain Combinations as Revealed by Human H and L Chain 'Roulette". J Immunol 150(3):880-887.

Final Office Action for U.S. Appl. No. 12/860,693, mailed Nov. 15, 2012.

Patent Examination Report No. 1 for AU 2008282739, issued Nov. 19, 2012.

Communication pursuant to Article 94(3) EPC for EP 08 830 207.0, mailed Nov. 22, 2012.

Notice on the Second Office Action (translation) for CN 200880101321.3, mailed Nov. 23, 2012.

Office Action for U.S. Appl. No. 13/204,336, mailed Nov. 26, 2012.

Partial European Search Report for EP 12172214.4, mailed Nov. 28, 2012, 10 pages.

European Search Report for EP 12172222.7, mailed Nov. 28, 2012, 15 pages.

Supplementary European Search Report for EP 10810675.8, mailed Dec. 4, 2012.

Patent Examination Report No. 1 for AU 2008299784, mailed Dec. 12, 2012.

Office Action for U.S. Appl. No. 13/204,336, mailed Jan. 7, 2013.

Non-Final Office Action for U.S. Appl. No. 12/860,834, mailed Jan. 10, 2013.

Office Action for U.S. Appl. No. 12/185,054, mailed Jan. 28, 2013.

Notice of the Second Office Action for CN 200880110519.8, mailed Dec. 31, 2012.

Supplementary European Search Report for EP 10810673.3, mailed Nov. 26, 2012.

```
hLOX     GLPDLVADPYYIQASTYVQKMSMYNLRCAAEENCLASTAYRADVRDYDHRVLLRFPQRVK 60
hLOXL1   GLPDLVPDPNYVQASTYVQRAHLYSLRCAAEEKCLASTAYAPEATDYDVRVLLRFPQRVK 60
mLOX     GLPDLVPDPYYIQASTYVQKMSMYNLRCAAEENCLASSAYRADVRDYDHRVLLRFPQRVK 60
hLOXL2   TAPDLVLNAEMVQQTTYLEDRPMFMLQCAMEENCLSASAAQTDPT-TGYRRLLRFSSQIH 59
mLOXL2   TAPDLVLNAEIVQQTAYLEDRPMSLLQCAMEENCLSASAVHTDPT-RGHRRLLRFSSQIH 59
hLOXL3   TASDLLLHSALVQETAYIEDRPLHMLYCAAEENCLASSARSANWP-YGHRRLLRFSSQIH 59
hLOXL4   SAPDLVMNAQLVQETAYLEDRPLSQLYCAHEENCLSKSADHMDWP-YGYRRLLRFSTQIY 59
          .**:  ..   :*  ::*::        :   *  **  **:**  :*     :       .  *  ****.  ::

hLOX     NQGTSDFLPSRPRYSWEWHSCHQHYHSMDEFSHYDLLDANTQRRVAEGHKASFCLEDTSC 120
hLOXL1   NQGTADFLPNRPRHTWEWHSCHQHYHSMDEFSHYDLLDAATGKKVAEGHKASFCLEDSTC 120
mLOX     NQGTSDFLPSRPRYSWEWHSCHQHYHSMDEFSHYDLLDANTQRRVAEGHKASFCLEDTSC 120
hLOXL2   NNGQSDFRPKNGRHAWIWHDCHRHYHSMEVFTHYDLLNLN-GTKVAEGHKASFCLEDTEC 118
mLOXL2   NNGQSDFRPKNGRHAWIWHDCHRHYHSMEVFTYYDLLSLN-GTKVAEGHKASFCLEDTEC 118
hLOXL3   NLGRADFRPKAGRHSWVVHECHGHYHSMDIFTHYDILTPN-GTKVAEGHKASFCLEDTEC 118
hLOXL4   NLGRTDFRPKTGRDSWVVHQCHRHYHSIEVFTHYDLLTLN-GSKVAEGHKASFCLEDTNC 118
          * *  :**  *.   *   :*  .  ****::  *::**:*           :**************: * hLOX     DYGYHRRFACTAH-TQGLSPGCYDTYGADIDCQWIDITDVKPGNYILKVSVNPSYLVPES 179
hLOXL1   DFGNLKRYACTSH-TQGLSPGCYDTYNADIDCQWIDITDVQPGNYILKVHVNPKYIVLES 179
mLOX     DYGYHRRFACTAH-TQGLSPGCYDTYAADIDCQWIDITDVQPGNYILKVSVNPSYLVPES 179
hLOXL2   EGDIQKNYECANFGDQGITMGCWDMYRHDIDCQWVDITDVPPGDYLFQVVINPNFEVAES 178
mLOXL2   EGDIQKSYECANFGEQGITMGCWDMYRHDIDCQWIDITDVPPGDYLFQVVINPNYEVPES 178
hLOXL3   QEDVSKRYECANFGEQGITVGCWDLYRHDIDCQWIDITDVKPGNYILQVVINPNFEVAES 178
hLOXL4   PTGLQRRYACANFGEQGVTVGCWDTYRHDIDCQWVDITDVGPGNYIFQVIVNPHYEVAES 178
           .    : :  *:  .    ::  :*  *   ****:*  :*:::*  :**   :  *  ** hLOX     DYTNNVVRCDIRYTGHHAYASGCTISPY---------------------- 207
hLOXL1   DFTNNVVRCNIHYTGRYVSATNCKIVQS---------------------- 207
mLOX     DYTNNVVRCDIRYTGHHAYASGCTISPY---------------------- 207
hLOXL2   DYSNNIMKCRSRYDGHRIWMYNCHIGGSFSEETEKKFEHFSGLLNNQLSPQ 229
mLOXL2   DFSNNIMKCRSRYDGYRIWMYNCHVGGAFSEETEQKFEHFSGLLNNQLSVQ 229
hLOXL3   DFTNNAMKCNCKYDGHRIWVHNCHIGDAFSEEANRRFERYPGQTSNQII-- 227
hLOXL4   DFSNNMLQCRCKYDGHRVWLHNCHTGNSYPANAELSLEQEQRLRNNLI--- 226
          *::**  ::*     :*  *       .* hLOX     (SEQ ID NO:1)
hLOXL1   (SEQ ID NO:17)
mLOX     (SEQ ID NO:5)
hLOXL2   (SEQ ID NO:3)
mLOXL2   (SEQ ID NO:7)
hLOXL3   (SEQ ID NO:18)
hLOXL4   (SEQ ID NO:19)
```

FIGURE 6

```
hLOX    GLPDLVADPYYIQASTYVQKMSMYNLRCAAEENCLASTAYRADVRDYDHRVLLRFPQRVK 60
hLOXL1  GLPDLVPDPNYVQASTYVQRAHLYSLRCAAEEKCLASTAYAPEATDYDVRVLLRFPQRVK 60
hLOXL2  TAPDLVLNAEMVQQTTYLEDRPMFMLQCAMEENCLSASAAQTDPT-TGYRRLLRFSSQIH 59
hLOXL3  TASDLLLHSALVQETAYIEDRPLHMLYCAAEENCLASSARSANWP-YGHRRLLRFSSQIH 59
hLOXL4  SAPDLVMNAQLVQETAYLEDRPLSQLYCAHEENCLSKSADHMDWP-YGYRRLLRFSTQIY 59
         .**:  .. :*  ::*::     : * ** **:**: :*    :   . * ****. ::

hLOX    NQGTSDFLPSRPRYSWEWHSCHQHYHSMDEFSHYDLLDANTQRRVAEGHKASFCLEDTSC 120
hLOXL1  NQGTADFLPNRPRHTWEWHSCHQHYHSMDEFSHYDLLDAATGKKVAEGHKASFCLEDSTC 120
hLOXL2  NNGQSDFRPKNGRHAWIWHDCHRHYHSMEVFTHYDLLNLN-GTKVAEGHKASFCLEDTEC 118
hLOXL3  NLGRADFRPKAGRHSWVWHECHGHYHSMDIFTHYDILTPN-GTKVAEGHKASFCLEDTEC 118
hLOXL4  NLGRTDFRPKTGRDSWVWHQCRHYHSIEVFTHYDLLTLN-GSKVAEGHKASFCLEDTNC 118
        * * :** *.   * :* . ****:: *:***:*        :*************: * hLOX    DYGYHRRFACTAH-TQGLSPGCYDTYGADIDCQWIDITDVKPGNYILKVSVNPSYLVPES 179
hLOXL1  DFGNLKRYACTSH-TQGLSPGCYDTYNADIDCQWIDITDVQPGNYILKVHVNPKYIVLES 179
hLOXL2  EGDIQKNYECANFGDQGITMGCWDMYRHDIDCQWVDITDVPPGDYLFQVVINPNFEVAES 178
hLOXL3  QEDVSKRYECANFGEQGITVGCWDLYRHDIDCQWIDITDVKPGNYILQVVINPNFEVAES 178
hLOXL4  PTGLQRRYACANFGEQGVTVGCWDTYRHDIDCQWVDITDVGPGNYIFQVIVNPHYEVAES 178
             . ::: *: .   :: :* *   ****:* :*:::* :** : * ** hLOX    DYTNNVVRCDIRYTGHHAYASGCTISPY--------------------- 207
hLOXL1  DFTNNVVRCNIHYTGRYVSATNCKIVQS--------------------- 207
hLOXL2  DYSNNIMKCRSRYDGHRIWMYNCHIGGSFSEETEKKFEHFSGLLNNQLSPQ 229
hLOXL3  DFTNNAMKCNCKYDGHRIWVHNCHIGDAFSEEANRRFERYPGQTSNQII-- 227
hLOXL4  DFSNNMLQCRCKYDGHRVWLHNCHTGNSYPANAELSLEQEQRLRNNLI--- 226
        *::** ::*   :* *:         .* hLOX    (SEQ ID NO:1)
hLOXL1  (SEQ ID NO:17)
hLOXL2  (SEQ ID NO:3)
hLOXL3  (SEQ ID NO:18)
hLOXL4  (SEQ ID NO:19)
```

FIGURE 7

CATALYTIC DOMAINS FROM LYSYL OXIDASE AND LOXL2

CROSS REFERENCE TO RELATED APPLICATIONS

This application claims benefit of U.S. provisional application No. 61/235,776 filed on Aug. 21, 2009, the disclosure of which is hereby incorporated by reference in its entirety for all purposes.

STATEMENT REGARDING FEDERAL SUPPORT

Not applicable.

FIELD

The present application is in the fields of enzymology and molecular biology.

BACKGROUND

Connective tissue provides a framework in which the cells and organs of the body reside. A primary component of connective tissue in vertebrates is the extracellular matrix. The two main structural constituents of the extracellular matrix are polysaccharides, which form a gel-like ground substance, and fibrous proteins embedded in the ground substance. Two of the most common of these fibrous proteins are collagen and elastin. Collagen fibers are formed by self-association of collagen fibrils, which are themselves assembled by the cross-linking of triple-helical collagen molecules. This cross-linking is catalyzed by lysyl oxidase (LOX) and related enzymes ("lysyl oxidase-like" or "LOXL"), all of which contain a catalytic domain capable of deaminating the ε-amino groups of lysine and hydroxylysine residues, resulting in conversion of peptidyl lysine to peptidyl-α-aminoadipic-δ-semialdehyde (allysine). Allysine residues are able to condense spontaneously with each other, resulting in crosslinking of collagen molecules.

The involvement of the extracellular matrix in various pathologies (including, for example, fibrosis and metastasis) has become increasingly apparent. See, for example, WO 01/83702 (Nov. 8, 2001); WO 2004/047720 (Jun. 10, 2004); WO 2007/126457 (Aug. 11, 2007); US 2006/0127402 (Jun. 15, 2006); US2007/0225242 (Sep. 27, 2007); US 2009/0053224 (Feb. 26, 2009); US 2009/0104201 (Apr. 23, 2009); Csiszar (2001) *Prog. Nucleic Acid Res. and Molec. Biol.* 70:1-32; Kirschmann et al. (2002) *Cancer Research* 62:4478-4483. Since lysyl oxidase and lysyl oxidase-like enzymes play a key role in the formation of the extracellular matrix, by crosslinking collagen, they represent important therapeutic targets. Hence, methods to screen for inhibitors of these collagen-crosslinking enzymes, methods for identifying molecules that bind to these enzymes, and sources of collagen-crosslinking activity for various therapeutic uses (e.g., wound healing) would all be desirable.

SUMMARY

The present disclosure provides isolated catalytic domains of the lysyl oxidase (LOX) and lysyl oxidase-like-2 (LOXL2) enzymes from humans and mice; along with nucleic acids encoding these catalytic domains. Thus, the following peptides, and nucleic acids encoding these peptides, are provided: human LOX catalytic domain, human LOXL2 catalytic domain, murine LOX catalytic domain and murine LOXL2 catalytic domain. Accordingly, the present disclosure provides:

1. A polypeptide comprising the amino acid sequence of the catalytic domain of human lysyl oxidase (LOX). (SEQ ID NO:1)
2. A polynucleotide comprising a nucleotide sequence encoding the catalytic domain of human lysyl oxidase (LOX). (SEQ ID NO:2)
3. A polypeptide comprising the amino acid sequence of the catalytic domain of human lysyl oxidase-like 2 (LOXL2). (SEQ ID NO:3)
4. A polynucleotide comprising a nucleotide sequence encoding the catalytic domain of human lysyl oxidase-like 2 (LOXL2). (SEQ ID NO:4)
5. A polypeptide comprising the amino acid sequence of the catalytic domain of murine lysyl oxidase (LOX). (SEQ ID NO:5)
6. A polynucleotide comprising a nucleotide sequence encoding the catalytic domain of murine lysyl oxidase (LOX). (SEQ ID NO:6)
7. A polypeptide comprising the amino acid sequence of the catalytic domain of murine lysyl oxidase-like 2 (LOXL2). (SEQ ID NO:7)
8. A polynucleotide comprising a nucleotide sequence encoding the catalytic domain of murine lysyl oxidase-like 2 (LOXL2). (SEQ ID NO:8)

Also provided are:

1a. A polypeptide comprising the amino acid sequence of all or part of the catalytic domain of human lysyl oxidase (LOX) as set forth herein (SEQ ID NO:1), that does not contain sequences of human LOX outside of its catalytic domain.

2a. A polynucleotide comprising a nucleotide sequence encoding all or part of the catalytic domain of human lysyl oxidase (LOX) as set forth herein (SEQ ID NO:2), that does not encode sequences of human LOX outside of its catalytic domain.

3a. A polypeptide comprising the amino acid sequence of all or part of the catalytic domain of human lysyl oxidase-like 2 (LOXL2) as set forth herein (SEQ ID NO:3), that does not contain sequences of human LOXL2 outside of its catalytic domain.

4a. A polynucleotide comprising a nucleotide sequence encoding all or part of the catalytic domain of human lysyl oxidase-like 2 (LOXL2) as set forth herein (SEQ ID NO:4), that does not encode sequences of human LOXL2 outside of its catalytic domain.

5a. A polypeptide comprising the amino acid sequence of all or part of the catalytic domain of murine lysyl oxidase (LOX) as set forth herein (SEQ ID NO:5), that does not contain sequences of murine LOX outside of its catalytic domain.

6a. A polynucleotide comprising a nucleotide sequence encoding all or part of the catalytic domain of murine lysyl oxidase (LOX) as set forth herein (SEQ ID NO:6), that does not encode sequences of murine LOX outside of its catalytic domain.

7a. A polypeptide comprising the amino acid sequence of all or part of the catalytic domain of murine lysyl oxidase-like 2 (LOXL2) as set forth herein (SEQ ID NO:7), that does not contain sequences of murine LOXL2 outside of its catalytic domain.

8a. A polynucleotide comprising a nucleotide sequence encoding all or part of the catalytic domain of murine lysyl oxidase-like 2 (LOXL2) as set forth herein (SEQ ID NO:8), that does not encode sequences of murine LOXL2 outside of its catalytic domain.

Also provided are expression vectors comprising the aforementioned nucleic acids and/or polynucleotides. Such expression vectors optionally contain promoters (e.g., T7 promoter, T3 promoter, SP6 promoter, E. coli RNA polymerase promoter, CMV promoter, SV40 promoter, PGK promoter, EF-1alpha promoter), transcription termination signals (e.g., SV40 termination signal), splice sites (e.g., SV40 splice sites, beta-globin splice site), ribosome binding sites, signal sequences (e.g., immunoglobulin kappa signal sequence), epitopes tags (e.g., myc), purification tags (e.g., $His_6$), replication origins and drug selection markers. Linker sequences, encoding linker amino acids and/or comprising restriction enzyme recognition sites, or any other type of linker sequence, can also be present in the expression vectors disclosed herein.

Accordingly, the present disclosure also provides:

9. A polypeptide comprising the amino acid sequence of all or part of the catalytic domain of human LOX that does not contain human LOX amino acid sequences outside of its catalytic domain, further comprising one or more of a signal sequence, an epitope tag and a $His_6$ purification tag; for example, a polypeptide comprising a signal sequence, the catalytic domain of human LOX, a myc epitope tag and a $His_6$ purification tag (e.g., SEQ ID NO:9).

10. A polynucleotide encoding a polypeptide according to embodiment 9; for example, a polynucleotide comprising sequences encoding a signal sequence, the catalytic domain of human LOX, a myc epitope tag and a $His_6$ purification tag (e.g., SEQ ID NO:10).

11. An expression vector comprising the polynucleotide of embodiment 10.

12. The expression vector of embodiment 11, further comprising any one of, any combination of, or all of a promoter, a drug selection marker and an origin of replication.

13. A polypeptide comprising the amino acid sequence of all or part of the catalytic domain of human LOXL2 that does not contain human LOXL2 amino acid sequences outside of its catalytic domain, further comprising one or more of a signal sequence, an epitope tag and a $His_6$ purification tag; for example, a polypeptide comprising a signal sequence, the catalytic domain of human LOXL2, a myc epitope tag and a $His_6$ purification tag (e.g., SEQ ID NO:11).

14. A polynucleotide encoding a polypeptide according to embodiment 13; for example, a polynucleotide comprising sequences encoding a signal sequence, the catalytic domain of human LOXL2, a myc epitope tag and a $His_6$ purification tag (e.g., SEQ ID NO:12).

15. An expression vector comprising the polynucleotide of embodiment 14.

16. The expression vector of embodiment 15, further comprising any one of, any combination of, or all of a promoter, a drug selection marker and an origin of replication.

17. A polypeptide comprising the amino acid sequence of all or part of the catalytic domain of murine LOX that does not contain murine LOX amino acid sequences outside of its catalytic domain, further comprising one or more of a signal sequence, an epitope tag and a $His_6$ purification tag; for example, a polypeptide comprising a signal sequence, the catalytic domain of murine LOX, a myc epitope tag and a $His_6$ purification tag (e.g., SEQ ID NO:13).

18. A polynucleotide encoding a polypeptide according to embodiment 17; for example, a polynucleotide comprising sequences encoding a signal sequence, the catalytic domain of murine LOX, a myc epitope tag and a $His_6$ purification tag (e.g., SEQ ID NO:14).

19. An expression vector comprising the polynucleotide of embodiment 18.

20. The expression vector of embodiment 19, further comprising any one of, any combination of, or all of a promoter, a drug selection marker and an origin of replication.

21. A polypeptide comprising the amino acid sequence of all or part of the catalytic domain of murine LOXL2 that does not contain murine LOXL2 amino acid sequences outside of its catalytic domain, further comprising one or more of a signal sequence, an epitope tag and a $His_6$ purification tag; for example, a polypeptide comprising a signal sequence, the catalytic domain of murine LOXL2, a myc epitope tag and a $His_6$ purification tag (e.g., SEQ ID NO:15).

22. A polynucleotide encoding a polypeptide according to embodiment 21; for example, a polynucleotide comprising sequences encoding a signal sequence, the catalytic domain of murine LOXL2, a myc epitope tag and a $His_6$ purification tag (e.g., SEQ ID NO:16).

23. An expression vector comprising the polynucleotide of embodiment 22.

24. The expression vector of embodiment 23, further comprising any one of, any combination of, or all of a promoter, a drug selection marker and an origin of replication.

The lane labeled "+" in each panel contained a protein containing a $His_6$ sequence, to serve as a positive control for the anti-$His_5$ antibody.

Figure 2:
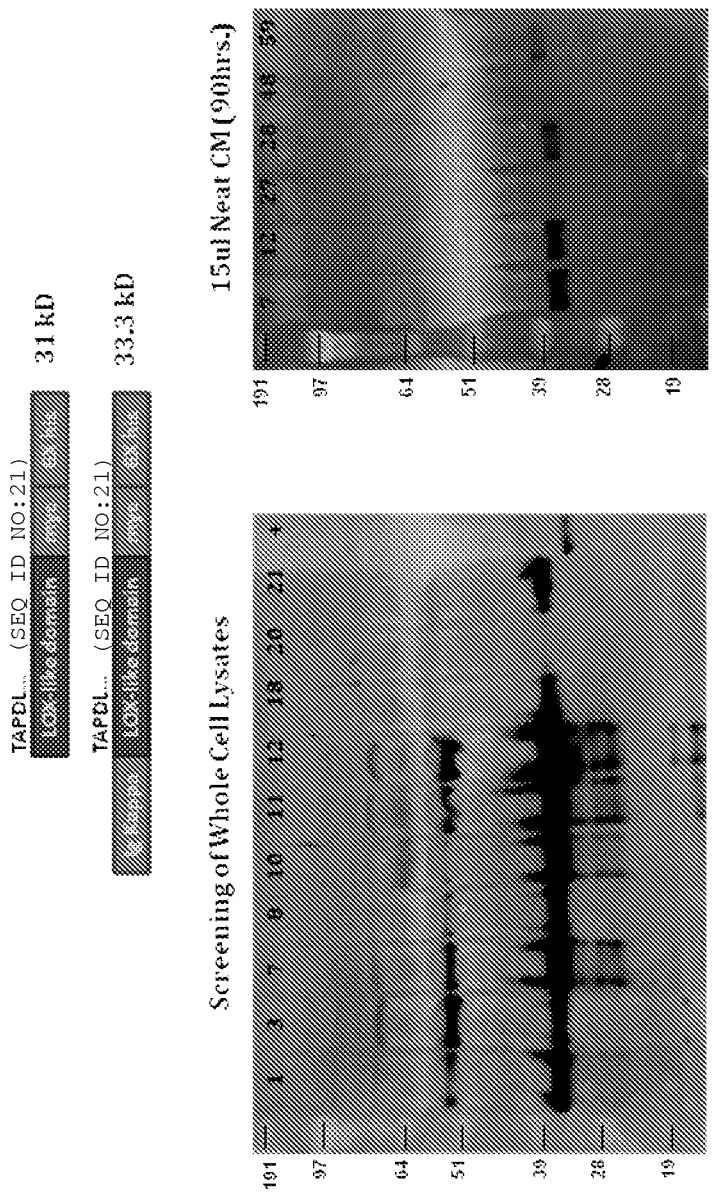

FIG. 2 shows expression of the catalytic domain of the human lysyl oxidase-like 2 (hLOXL2) protein by HEK293 cells transfected with the phLOXL2MCD expression vector. The left panel shows an immunoblot of whole cell lysates from a number of stably transfected cell lines (indicated by a number at the top of each lane), with each lane containing material from approximately $1 \times 10^5$ cells. The right panel shows an immunoblot of a polyacrylamide gel containing samples of undiluted growth medium (15 µl Neat CM) from each of six cell lines (indicated by numbers). All blots were probed with a primary mouse anti-$His_5$ antibody, then reacted with a secondary HRP conjugated donkey-anti-mouse antibody. HRP activity was revealed using the Chemi-Glow® reagent (Alpha Innotech, San Leandro, Calif.). The processed catalytic domain has a predicted molecular weight of 31 kD.

The lane labeled "+" in the left panel contained a protein containing a $His_6$ sequence, to serve as a positive control for the anti-$His_5$ antibody.

Figure 3:
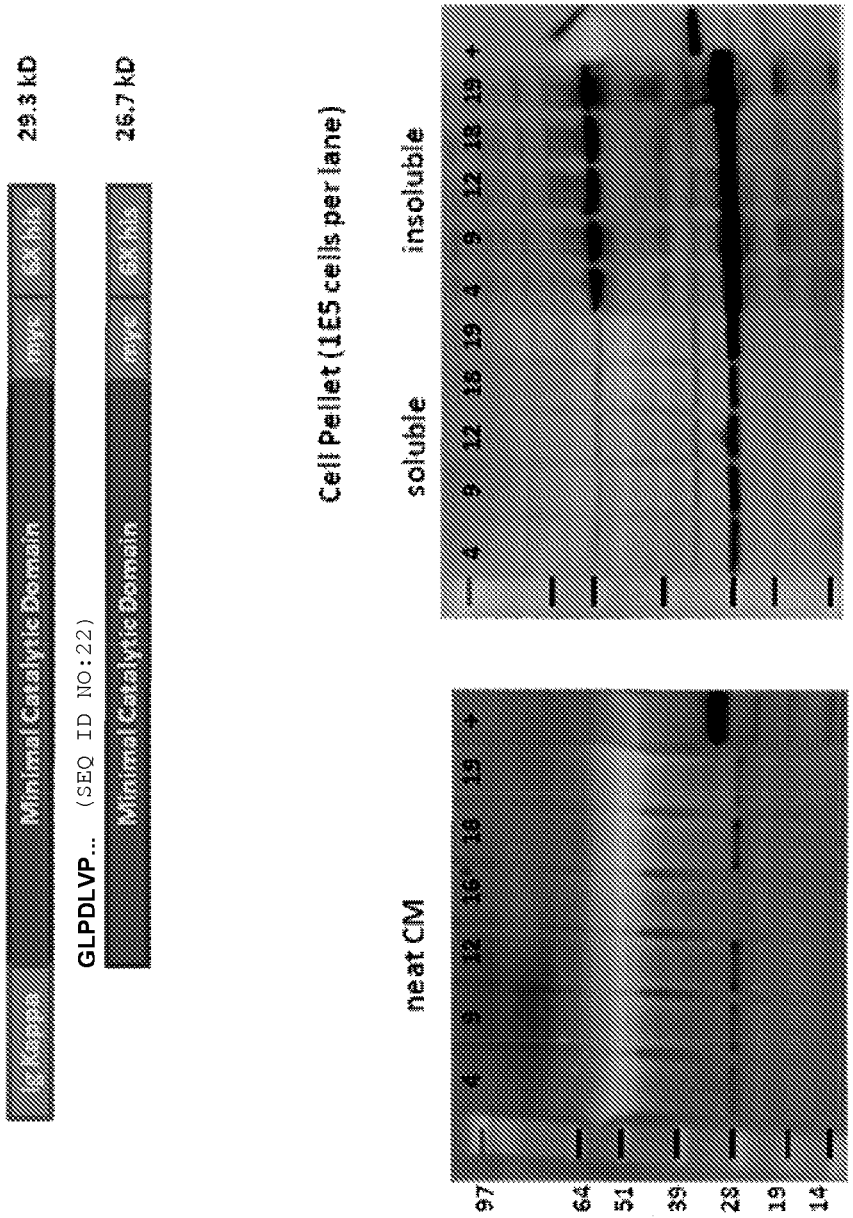

FIG. 3 shows expression of the catalytic domain of the murine lysyl oxidase (mLOX) protein by HEK293 cells transfected with the pmLOXMCD expression vector. Analysis of five stably transfected cell lines (numbered 4, 9, 12, 18 and 19) by immunoblotting is shown. The left panel shows an immunoblot of a polyacrylamide gel containing samples (15 ul) of undiluted growth medium (neat CM) from each of six cell lines. The right panel shows analysis of soluble and insoluble intracellular fractions from five of those six lines, with each lane containing material from approximately $10^5$ cells. All blots were probed with a primary mouse anti-$His_5$ antibody, then reacted with a secondary HRP conjugated donkey-anti-mouse antibody. HRP activity was revealed using the Chemi-Glow® reagent (Alpha Innotech, San Leandro, Calif.). The processed catalytic domain has a predicted molecular weight of 27 kD.

Figure 4:
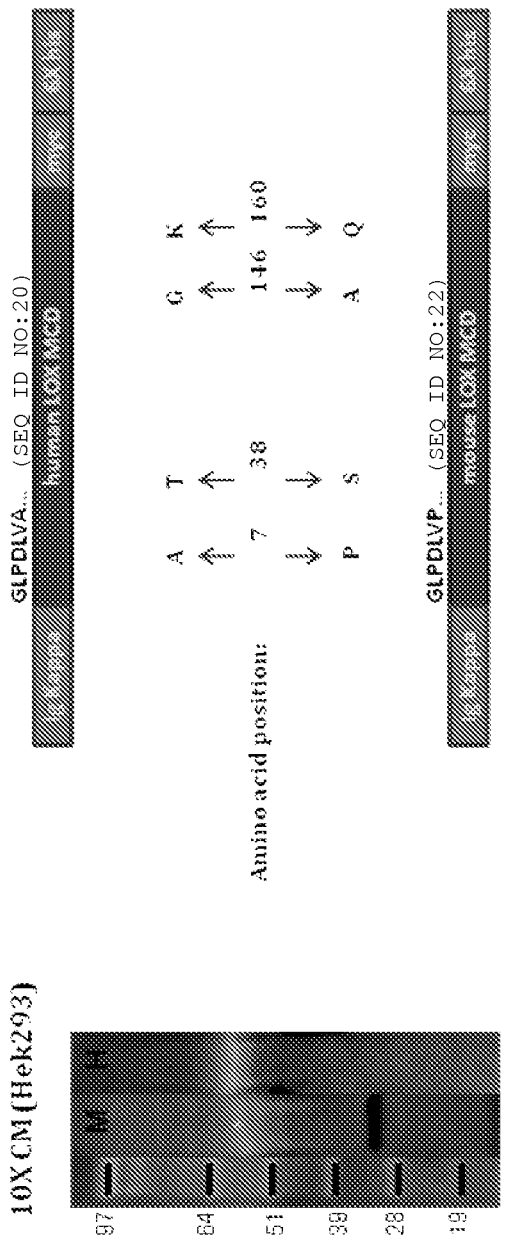

FIG. 4 shows differences in secretion and amino acid sequence between the human and murine LOX catalytic domains. See Example 10 for details.

Figure 5:
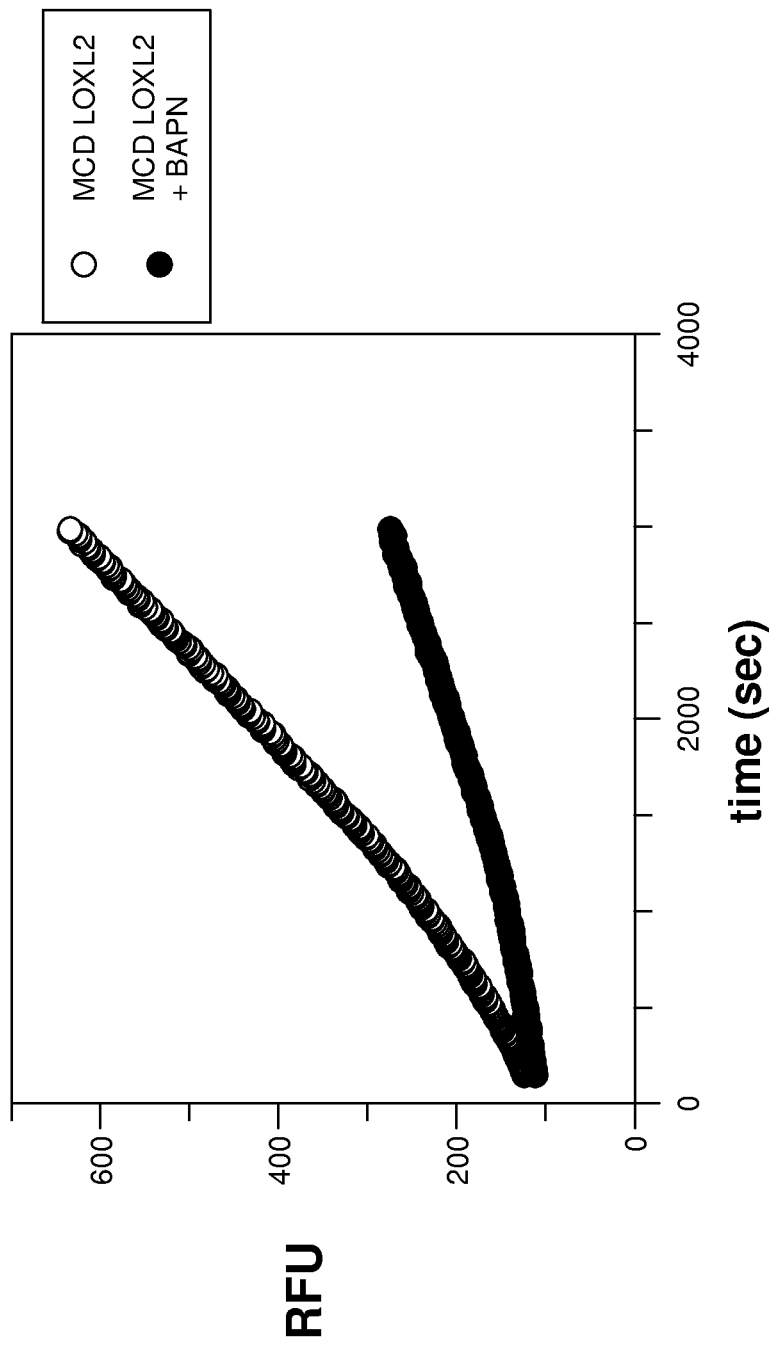

FIG. 5 shows a time-course of resorufin production (measured by absorbance at 590 nm) in an Amplex® Red assay of an isolated human LOXL2 catalytic domain. See example 12 for details.

FIG. 6 shows an alignment of amino acid sequences of various polypeptides in the present disclosure, including those that derive from human (hLOX, hLOXL1, hLOXL2, etc.) and mouse (mLOX and mLOXL2). The numbering of the amino acid residues starts with "one" at the most N-terminal residue shown and is not necessarily in accordance with convention in the art. Asterisks indicate amino acid identity at the position among all the polypeptides shown, while colons indicate conservative amino acid substitutions and single dots indicate semi-conservative amino acid substitutions, in accordance with the ClustalW2 program provided by the European Bioinformatics Institute (EMBL-EBI).

FIG. 7 shows an alignment of the amino acid sequences of various polypeptides in the present disclosure, including only those that derive from human. Numbering and legends are the same as those used in FIG. 6.

DETAILED DESCRIPTION

Practice of the present disclosure employs, unless otherwise indicated, standard methods and conventional techniques in the fields of cell biology, toxicology, molecular biology, biochemistry, cell culture, immunology, oncology, recombinant DNA and related fields as are within the skill of the art. Such techniques are described in the literature and thereby available to those of skill in the art. See, for example, Alberts, B. et al., "Molecular Biology of the Cell," $5^{th}$ edition, Garland Science, New York, N.Y., 2008; Voet, D. et al. "Fundamentals of Biochemistry: Life at the Molecular Level," $3^{rd}$ edition, John Wiley & Sons, Hoboken, N.J., 2008; Sambrook, J. et al., "Molecular Cloning: A Laboratory Manual," $3^{rd}$ edition, Cold Spring Harbor Laboratory Press, 2001; Ausubel, F. et al., "Current Protocols in Molecular Biology," John Wiley & Sons, New York, 1987 and periodic updates; Freshney, R. I., "Culture of Animal Cells: A Manual of Basic Technique," $4^{th}$ edition, John Wiley & Sons, Somerset, N.J., 2000; and the series "Methods in Enzymology," Academic Press, San Diego, Calif.

Lysyl Oxidase-Type Enzymes

As used herein, the terms "lysyl oxidase-type enzyme" or "lysyl oxidase enzyme" refer to a member of a family of proteins containing a catalytic domain that catalyzes oxidative deamination of ε-amino groups of lysine and hydroxylysine residues, resulting in conversion of peptidyl lysine to peptidyl-α-aminoadipic-δ-semialdehyde (allysine) and the release of stoichiometric quantities of ammonia and hydrogen peroxide:

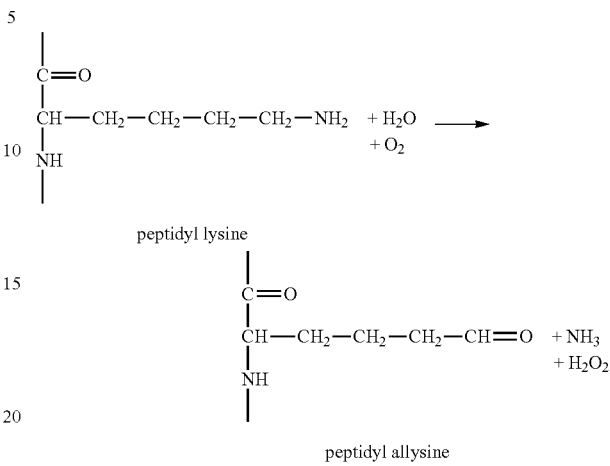

This reaction most often occurs extracellularly, on lysine residues in collagen and elastin. The aldehyde residues of allysine are reactive and can spontaneously condense with other allysine and lysine residues, resulting in crosslinking of collagen molecules to form collagen fibrils.

Lysyl oxidase enzymes have been purified from chicken, rat, mouse, bovines and humans. All lysyl oxidase enzymes contain a common catalytic domain, approximately 205 amino acids in length, located in the carboxy-terminal portion of the protein and containing the active site of the enzyme. The active site contains a copper-binding site which includes a conserved amino acid sequence containing four histidine residues which coordinate a Cu(II) atom. The active site also contains a lysyltyrosyl quinone (LTQ) cofactor, formed by intramolecular covalent linkage between a lysine and a tyrosine residue (corresponding to lys314 and tyr349 in rat lysyl oxidase, and to lys320 and tyr355 in human lysyl oxidase). The sequence surrounding the tyrosine residue that forms the LTQ cofactor is also conserved among lysyl oxidase enzymes. The catalytic domain also contains ten conserved cysteine residues, which participate in the formation of five disulfide bonds. The catalytic domain also includes a fibronectin binding domain. Finally, an amino acid sequence similar to a growth factor and cytokine receptor domain, containing four cysteine residues, is present in the catalytic domain.

Despite the presence of these conserved regions, the different lysyl oxidase-type enzymes can be distinguished from one another, both within and outside their catalytic domains, by virtue of regions of divergent nucleotide and amino acid sequence.

The first member of this family of enzymes to be isolated and characterized was lysyl oxidase (EC 1.4.3.13); also known as protein-lysine 6-oxidase, protein-L-lysine:oxygen 6-oxidoreductase (deaminating), or LOX. See, e.g., Harris et al., *Biochim. Biophys. Acta* (1974) 341:332-344; Rayton et al. (1979) *J. Biol. Chem.* 254:621-626; Stassen (1976) *Biophys. Acta* 438:49-60.

Additional lysyl oxidase-type enzymes were subsequently discovered. These proteins have been dubbed "LOX-like," or "LOXL." They all contain the common catalytic domain described above and have similar enzymatic activity. Currently, five different lysyl oxidase enzymes are known to exist in both humans and mice: LOX and the four LOX related, or LOX-like proteins LOXL1 (also denoted "lysyl oxidase-like," "LOXL" or "LOL"), LOXL2 (also denoted "LOR-1"), LOXL3, and LOXL4. Each of the genes encoding the five different lysyl oxidase-type enzymes resides on a different chromosome. See, for example, Molnar et al. (2003) *Biochim Biophys Acta.* 1647:220-24; Csiszar (2001) *Prog. Nucl. Acid Res.* 70:1-32; WO 01/83702 published on Nov. 8, 2001, and U.S. Pat. No. 6,300,092, all of which are incorporated by reference herein. A LOX-like protein termed LOXC, with some similarity to LOXL4 but with a different expression pattern, has been isolated from a murine EC cell line. Ito et al. (2001) *J. Biol. Chem.* 276:24023-24029. Two lysyl oxidase enzymes, DmLOXL-1 and DmLOXL-2, have been isolated from *Drosophila*.

Although all lysyl oxidase-type enzymes share a common catalytic domain, they also differ from one another, particularly within their amino-terminal regions. The four LOXL proteins have amino-terminal extensions, compared to LOX. Thus, while human preproLOX (e.g., the primary translation product prior to signal sequence cleavage, see below) contains 417 amino acid residues; LOXL1 contains 574, LOXL2 contains 638, LOXL3 contains 753 and LOXL4 contains 756. The convention of numbering full length lysyl oxidase-type enzymes in the art starts from "one" at the most N-terminal amino acid residue which begins with the signal sequence.

Within their amino-terminal regions, LOXL2, LOXL3 and LOXL4 contain four repeats of the scavenger receptor cysteine-rich (SRCR) domain. These domains are not present in LOX or LOXL1. SRCR domains are found in secreted, transmembrane, or extracellular matrix proteins, and are known to mediate ligand binding in a number of secreted and receptor proteins. Hoheneste et al. (1999) *Nat. Struct. Biol.* 6:228-232; Sasaki et al. (1998) *EMBO J.* 17:1606-1613. In addition to its SRCR domains, LOXL3 contains a nuclear localization signal in its amino-terminal region. A proline-rich domain appears to be unique to LOXL1. Molnar et al. (2003) *Biochim. Biophys. Acta* 1647:220-224. The various lysyl oxidase-type enzymes also differ in their glycosylation patterns.

Tissue distribution also differs among the lysyl oxidase-type enzymes. Human LOX mRNA is highly expressed in the heart, placenta, testis, lung, kidney and uterus, but marginally in the brain and liver. mRNA for human LOXL1 is expressed in the placenta, kidney, muscle, heart, lung, and pancreas and, similar to LOX, is expressed at much lower levels in the brain and liver. Kim et al. (1995) *J. Biol. Chem.* 270:7176-7182. High levels of LOXL2 mRNA are expressed in the uterus, placenta, and other organs, but as with LOX and LOXL, low levels are expressed in the brain and liver. Jourdan Le-Saux et al. (1999) *J. Biol. Chem.* 274:12939:12944. LOXL3 mRNA is highly expressed in the testis, spleen, and prostate, moderately expressed in placenta, and not expressed in the liver, whereas high levels of LOXL4 mRNA are observed in the liver. Huang et al. (2001) *Matrix Biol.* 20:153-157; Maki and Kivirikko (2001) *Biochem. J.* 355:381-387; Jourdan Le-Saux et al. (2001) *Genomics* 74:211-218; and Asuncion et al. (2001) *Matrix Biol.* 20:487-491.

The expression and/or involvement of the different lysyl oxidase enzymes in diseases may also vary. See, for example, Kagan (1994) *Pathol. Res. Pract.* 190:910-919; Murawaki et al. (1991) *Hepatology* 14:1167-1173; Siegel et al. (1978) *Proc. Natl. Acad. Sci. USA* 75:2945-2949; Jourdan Le-Saux et al. (1994) *Biochem. Biophys. Res. Comm.* 199:587-592; and Kim et al. (1999) *J. Cell Biochem.* 72:181-188. Lysyl oxidase-type enzymes have also been implicated in a number of cancers, including head and neck cancer, bladder cancer, colon cancer, esophageal cancer and breast cancer. See, for example, Wu et al. (2007) *Cancer Res.* 67:4123-4129; Gorough et al. (2007) *J. Pathol.* 212:74-82; Csiszar (2001) *Prog. Nucl. Acid Res.* 70:1-32 and Kirschmann et al. (2002) *Cancer Res.* 62:4478-4483.

Thus, although the lysyl oxidase-type enzymes exhibit some overlap in structure and function, each appears to have distinct functions as well. With respect to structure, for example, certain antibodies raised against the catalytic domain of the human LOX protein do not bind to human LOXL2. With respect to function, it has been reported that targeted deletion of LOX appears to be lethal at parturition in mice, whereas LOXL1 deficiency causes no severe developmental phenotype. Hornstra et al. (2003) *J. Biol. Chem.* 278: 14387-14393; Bronson et al. (2005) *Neurosci. Lett.* 390:118-122.

Although the most widely documented activity of lysyl oxidase-type enzymes is the oxidation of specific lysine residues in collagen and elastin outside of the cell, there is evidence that lysyl oxidase-type enzymes also participate in a number of intracellular processes. For example, there are reports that some lysyl oxidase-type enzymes regulate gene expression. Li et al. (1997) *Proc. Natl. Acad. Sci. USA* 94:12817-12822; Giampuzzi et al. (2000) *J. Biol. Chem.* 275: 36341-36349. In addition, LOX has been reported to oxidize lysine residues in histone H1. Additional extracellular activities of LOX include the induction of chemotaxis of monocytes, fibroblasts and smooth muscle cells. Lazarus et al. (1995) *Matrix Biol.* 14:727-731; Nelson et al. (1988) *Proc. Soc. Exp. Biol. Med.* 188:346-352. Expression of LOX itself is induced by a number of growth factors and steroids such as TGF-β, TNF-α and interferon. Csiszar (2001) *Prog. Nucl. Acid Res.* 70:1-32. Recent studies have attributed other roles to LOX in diverse biological functions such as developmental regulation, tumor suppression, cell motility, and cellular senescence.

Examples of lysyl oxidase (LOX) proteins from various sources include enzymes having an amino acid sequence substantially identical to a polypeptide expressed or translated from one of the following sequences: EMBL/GenBank accessions: M94054; AAA59525.1—mRNA; S45875; AAB23549.1—mRNA; S78694; AAB21243.1—mRNA; AF039291; AAD02130.1—mRNA; BC074820; AAH74820.1—mRNA; BC074872; AAH74872.1—mRNA; M84150; AAA59541.1—Genomic DNA. One embodiment of LOX is human lysyl oxidase (hLOX) preproprotein.

Exemplary disclosures of sequences encoding lysyl oxidase-like enzymes are as follows: LOXL1 is encoded by mRNA deposited at GenBank/EMBL BC015090; AAH15090.1; LOXL2 is encoded by mRNA deposited at GenBank/EMBL U89942; LOXL3 is encoded by mRNA deposited at GenBank/EMBL AF282619; AAK51671.1; and LOXL4 is encoded by mRNA deposited at GenBank/EMBL AF338441; AAK71934.1.

The primary translation product of the LOX protein, known as the prepropeptide, contains a signal sequence extending from amino acids 1-21. This signal sequence is released intracellularly by cleavage between Cys21 and Ala22, in both mouse and human LOX, to generate a 46-48 kDa propeptide form of LOX, also referred to herein as the full-length form. The propeptide is N-glycosylated during passage through the Golgi apparatus to yield a 50 kDa protein, then secreted into the extracellular environment. At this stage, the protein is catalytically inactive. A further cleavage, between Gly168 and Asp169 in mouse LOX, and between Gly174 and Asp175 in human LOX, generates the mature, catalytically active, 30-32 kDA enzyme, releasing a 18 kDa propeptide. This final cleavage event is catalyzed by the metalloendoprotease procollagen C-proteinase, also known as bone morphogenetic protein-1 (BMP-1). Interestingly, this enzyme also functions in the processing of LOX's substrate, collagen. The N-glycosyl units are subsequently removed.

Potential signal peptide cleavage sites have been predicted at the amino termini of LOXL1, LOXL2, LOXL3, and LOXL4. The predicted signal cleavage sites are between Gly25 and Gln26 for LOXL1, between Ala25 and Gln26, for LOXL2, between Gly25 and Ser26 for LOXL3 and between Arg23 and Pro24 for LOXL4.

A BMP-1 cleavage site in the LOXL1 protein has been identified between Ser354 and Asp355. Borel et al. (2001) *J. Biol. Chem.* 276:48944-48949. Potential BMP-1 cleavage sites in other lysyl oxidase-type enzymes have been predicted, based on the consensus sequence for BMP-1 cleavage in procollagens and pro-LOX being at an Ala/Gly-Asp sequence, often followed by an acidic or charged residue. A predicted BMP-1 cleavage site in LOXL3 is located between Gly447 and Asp448; processing at this site may yield a mature peptide of similar size to mature LOX. A potential cleavage site for BMP-1 was also identified within LOXL4, between residues Ala569 and Asp570. Kim et al. (2003) *J. Biol. Chem.* 278:52071-52074. LOXL2 may also be proteolytically cleaved analogously to the other members of the LOXL family and secreted. Akiri et al. (2003) *Cancer Res.* 63:1657-1666.

Based on the presence of a common catalytic domain in the lysyl oxidase-type enzymes, certain amino acid residues of the C-terminal 30 kDa region of the proenzyme in which the active site is located are highly conserved. A more moderate degree of conservation (approximately 60-70%) is observed in the propeptide domain.

For the purposes of the present disclosure, the term "lysyl oxidase-type enzyme" encompasses all five of the lysine oxidizing enzymes discussed above, i.e., LOX, LOXL1 (also identified as LOXL), LOXL2, LOXL3 and LOXL4; and also encompasses functional fragments and/or derivatives of LOX, LOXL1, LOXL2, LOXL3 and LOXL4 that substantially retain enzymatic activity; e.g., the ability to catalyze deamination of lysyl residues. A "fragment and/or derivative" in the context of an amino acid sequence or polynucleotide sequence (e.g., an amino acid sequence "derived from" LOXL2) is meant to indicate that the polypeptide or nucleic acid contains a contiguous sequence of all or a portion of a naturally-occurring lysyl oxidase-type enzymes protein or its encoding nucleic acid, and is not meant to be limiting as to the source or method in which the protein or nucleic acid is made.

Typically, a functional fragment or derivative retains at least 50% of its lysine oxidation activity. In some embodiments, a functional fragment or derivative retains at least 60%, at least 70%, at least 80%, at least 90%, at least 95%, at least 99% or 100% of its lysine oxidation activity.

It is also intended that a functional fragment of a lysyl oxidase-type enzyme can include conservative amino acid substitutions (with respect to the native polypeptide sequence) that do not substantially alter catalytic activity. The term "conservative amino acid substitution" refers to grouping of amino acids on the basis of certain common structures and/or properties. With respect to common structures, amino acids can be grouped into those with non-polar side chains (glycine, alanine, valine, leucine, isoleucine, methionine, proline, phenylalanine and tryptophan), those with uncharged polar side chains (serine, threonine, asparagine, glutamine, tyrosine and cysteine) and those with charged polar side chains (lysine, arginine, aspartic acid, glutamic acid and histidine). A group of amino acids containing aromatic side chains includes phenylalanine, tryptophan and tyrosine. Heterocyclic side chains are present in proline, tryptophan and histidine. Within the group of amino acids containing non-polar side chains, those with short hydrocarbon side chains (glycine, alanine, valine. leucine, isoleucine) can be distinguished from those with longer, non-hydrocarbon side chains (methionine, proline, phenylalanine, tryptophan). Within the group of amino acids with charged polar side chains, the acidic amino acids (aspartic acid, glutamic acid) can be distinguished from those with basic side chains (lysine, arginine and histidine).

A functional method for defining common properties of individual amino acids is to analyze the normalized frequencies of amino acid changes between corresponding proteins of homologous organisms (Schulz, G. E. and R. H. Schirmer, Principles of Protein Structure, Springer-Verlag, 1979). According to such analyses, groups of amino acids can be defined in which amino acids within a group are preferentially substituted for one another in homologous proteins, and therefore have similar impact on overall protein structure (Schulz, G. E. and R. H. Schirmer, Principles of Protein Structure, Springer-Verlag, 1979). According to this type of analysis, conservative amino acid substitution" refers to a substitution of one amino acid residue for another sharing chemical and physical properties of the amino acid side chain (e.g., charge, size, hydrophobicity/hydrophilicity). Following are examples of amino acid residues sharing certain chemical and/or physical properties:

(i) amino acids containing a charged group, consisting of Glu, Asp, Lys, Arg and His, (ii) amino acids containing a positively-charged group, consisting of Lys, Arg and His, (iii) amino acids containing a negatively-charged group, consisting of Glu and Asp, (iv) amino acids containing an aromatic group, consisting of Phe, Tyr and Trp, (v) amino acids containing a nitrogen ring group, consisting of His and Trp, (vi) amino acids containing a large aliphatic non-polar group, consisting of Val, Leu and Ile, (vii) amino acids containing a slightly-polar group, consisting of Met and Cys, (viii) amino acids containing a small-residue group, consisting of Ser, Thr, Asp, Asn, Gly, Ala, Glu, Gln and Pro, (ix) amino acids containing an aliphatic group consisting of Val, Leu, Ile, Met and Cys, and (x) amino acids containing a hydroxyl group consisting of Ser and Thr.

Certain "conservative substitutions" may include substitution within the following groups of amino acid residues: gly, ala; val, ile, leu; asp, glu; asn, gln; ser, thr; lys, arg; and phe, tyr.

Thus, as exemplified above, conservative substitutions of amino acids are known to those of skill in this art and can be made generally without altering the biological activity of the resulting molecule. Those of skill in this art also recognize that, in general, single amino acid substitutions in non-essential regions of a polypeptide do not substantially alter biological activity. See, e.g., Watson, et al., "Molecular Biology of the Gene," 4th Edition, 1987, The Benjamin/Cummings Pub. Co., Menlo Park, Calif., p. 224.

For additional information regarding lysyl oxidase enzymes, see, e.g., Rucker et al. (1998) *Am. J. Clin. Nutr.* 67:996S-1002S and Kagan et al. (2003) *J. Cell. Biochem* 88:660-672. See also co-owned United States patent applications US 2009/0053224 (Feb. 26, 2009) and US 2009/0104201 (Apr. 23, 2009); the disclosures of which are incorporated by reference herein for the purposes of describing lysyl oxidase and lysyl oxidase-like enzymes, modulators of these enzymes, and methods for identifying modulators of these enzymes. See also WO 2004/47720 (Jun. 10, 2004); WO 2007/126457 (Aug. 11, 2007); WO 2009/010974 (Jan. 22, 2009); US 2006/0127402 (Jun. 15, 2006); US 2007/0021365 (Jan. 25, 2007) and US 2007/0225242 (Sep. 27, 2007); all of which are incorporated by reference herein for the purposes of describing lysyl oxidase and lysyl oxidase-like enzymes, modulators of these enzymes, and methods for identifying modulators of these enzymes.

Polypeptides Having a Catalytic Domain of a Lysyl Oxidase or Lysyl Oxidase-Type Enzyme The present disclosure provides polypeptides having activity of a lysyl oxidase-type enzyme, such as those belonging to EC 1.4.3.13 in accordance with the nomenclature of International Union of Biochemistry and Molecular Biology, as described above. A full-length protein contains a signal sequence and/or propeptide, both of which may be cleaved before the protein attains full catalytic activity in vivo. The full-length lysyl oxidase or lysyl oxidase-like enzyme may be of a length of more than 100, 200, 300, 400, 500, 700, up to 754 or more amino acid residues. The mature full-length protein without the signal sequence and/or propeptide may be of a length of more than 100, 200, 240, 480, 720, 730, up to 740 or more amino acid residues.

The polypeptides of the present disclosure can be derived from the mature full-length LOX or LOXL proteins (e.g. without the signal peptide and/or propeptide). Exemplary polypeptides can have any of the amino acid sequences as set forth in FIGS. 6 and 7.

FIG. 6 shows an alignment of amino acid sequences of polypeptides that are derived from human LOX, human LOXL1, human LOXL2, human LOXL3, human LOXL4, murine LOX, and murine LOXL2. FIG. 7 shows an alignment of the sequences of polypeptides that are derived from only human LOX/LOXL proteins. For convenience, the numbering of the amino acid residues starts with "one" at the most N-terminal residue shown in FIGS. 6 and 7. Polypeptides of the present disclosure thus can be described with reference to the numbering system used for sequences set forth in FIGS. 6 and 7 or the numbering system used in the art as described previously. Alternatively, the polypeptides may be described with reference to the sequence identifier numbers assigned herein. Asterisks in FIGS. 6 and 7 indicate an identical amino acid at the position among all the polypeptides shown, while colons indicate conservative amino acid substitutions and single dots indicate semi-conservative amino acid substitutions, in accordance with the legends used by the ClustalW2 program provided by the European Bioinformatics Institute (EMBL-EBI).

The polypeptides of the present disclosure may encompass a polypeptide having at least about 50, at least about 75, at least about 100, at least about 120, at least about 140, at least about 150, at least about 170, at least about 180, at least about 200, at least about 220, up to at least about 240 or more amino acids of the C-terminal portion of a lysyl oxidase-type enzyme. For example, a polypeptide of the present disclosure may contain the C-terminal 207 amino acid residues as shown by SEQ ID NO: 1, SEQ ID NO: 5, or SEQ ID NO: 17 in FIG. 6. Polypeptides of the present disclosure also encompass those having an amino acid sequence that is less than that of a naturally-occurring full-length lysyl oxidase-type enzyme. Polypeptides can contain up to about 25, up to about 50, up to about 75, up to about 100, up to about 120, up to about 140, up to about 160, up to about 180, up to about 200, up to about 220, up to about 230 or more amino acid residues in a C-terminal portion of a LOX or LOXL-protein, e.g. as exemplified by sequences set forth in FIGS. 6 and 7. The polypeptides may exclude the signal sequence, the propeptide, and/or any of the portions of the LOX or LOXL-protein that are N-terminal to the sequences shown in FIGS. 6 and 7.

The polypeptides of the present disclosure may also be described with reference to the numbering system used in the art as described above, in which amino acid number "one" denotes the most N-terminal amino acid residue for the full-length LOX or full-length LOXL-proteins containing the signal sequence. According to such numbering, the polypeptides can be described as those encompassing an amino acid sequence starting at residue number between about 190 and 240, about 200 and 230 or between about 210 and 220 in LOX (e.g. SEQ ID NO: 1 or SEQ ID NO:5). The polypeptide may encompass an amino acid sequence starting at residue number between about 350 and 360, between about 340 and 370, or between about 330 and 380 in LOXL1. Alternatively, the polypeptide may encompass an amino acid sequence starting at residue number between about 540 and 550, between about 530 and 560, or between about 520 and 570 in LOXL2 (e.g. SEQ ID NO: 3 or SEQ ID NO:7). The polypeptide may also encompass an amino acid sequence starting at residue number between about 520 and 530, between about 510 and 540, or between about 500 and 550 in LOXL3. The polypeptide may also encompass an amino acid sequence starting at residue number between about 530 and 540, between about 540 and 550, or between about 530 and 560 in LOXL4.

Polypeptides of the present disclosure encompass those having 1, 2, 3, 4, 5, 6, 7, 8, 9 or 10 or more amino acid substitutions, e.g., conservative amino acid substitutions as compared to an amino acid sequence set forth in FIGS. 6 and 7. Guidance for amino acid substitutions can be obtained from the alignments provided in FIGS. 6 and 7. Amino acid residues that may be substituted may be located at residue positions that are not highly conserved, such as those not marked by an asterisk, colons, or dots. The ordinarily skilled artisan will appreciate that based on the alignments shown, amino acid residues at certain residue positions may tolerate substitutions, deletions, and/or insertions without changing the physical and chemical property of the overall polypeptide as compared to other residue positions.

Polypeptides of the present disclosure encompass those having an amino acid sequence that is at least 80%, at least 90%, at least 95%, at least 99% or 100% identical to any of the polypeptides shown in FIG. 6. For example, the amino acid sequence of the murine LOX catalytic domain polypeptide shown in FIG. 6 shares 98% amino acid sequence identity with the amino acid sequence of the human LOX catalytic domain polypeptide.

A protein from which a polypeptide of the present disclosure can be derived in accordance with the description above includes LOX (GenBank Accession No. NP_002308), LOXL1 (NP_005567), LOXL2 (NP_002309), LOXL3 (NP_115882), and LOXL4 (NP_115587), in which the aforementioned GenBank Accession numbers denote human sequences. In addition to those found in humans, these LOX or LOXL proteins cam also include those found in mouse or other mammals. For example, a LOX, LOXL1, or LOXL2 protein can be murine in origin (GenBank accession numbers NP_034858, NP_034859, NP_201582, respectively).

The subject polypeptides can include amino acid sequences derived from a lysyl oxidase-type enzyme (e.g., LOX or LOXL2) further comprising heterologous amino acid sequences, e.g., LOX or LOXL2 sequences linked to a polypeptide that is not part of a LOX or LOXL2 protein. Such polypeptides can be fusion proteins, such as a fusion protein containing epitope tags, purification tags, and/or detectable labels. A fusion protein can optionally include a linker sequence between the heterologous sequences and the amino acid sequence derived from the lysyl oxidase-type enzyme. Methods for producing a fusion protein of interest when provided a nucleic acid sequence are well-known in the art. Other heterologous elements and exemplary fusion proteins are described in more detail below.

Exemplary polypeptides containing heterologous elements may include myc and/or $His_6$ tags and may optionally include flanking linker sequences, such as those set forth in SEQ ID NO:9, SEQ ID NO:11, SEQ ID NO:13, or SEQ ID NO:15.

Polypeptides of the present disclosure further encompass those that are joined to a reporter polypeptide, e.g., a fluorescent protein, and/or conjugated to a molecule. The molecule conjugated to the polypeptide may be a carrier molecule or an immunogen known to elicit an immune response when present in an animal (e.g., an adjuvant). Other conjugates may include those that facilitate delivery and/or increase the half-life of the subject polypeptide.

The polypeptide of the present disclosure may also contain one or more poly(ethylene glycol) (PEG) moieties. Such polypeptides are referred to as "PEGylated polypeptides." Methods and reagents suitable for PEGylation of polypeptides are well known in the art. In general, PEG suitable for conjugation to a polypeptide is generally soluble in water at room temperature, and has the general formula $R(O-CH_2-CH_2)_nO-R$, where R is hydrogen or a protective group such as an alkyl or an alkanol group, and where n is an integer from 1 to 1000. Where R is a protective group, it generally contains from 1 to 8 carbon atoms.

The PEG may have at least one hydroxyl group modified to generate a functional group that is reactive with an amino group (e.g., an epsilon amino group of a lysine residue or a free amino group at the N-terminus of a polypeptide) or a carboxyl group in the polypeptide.

Additional derivatives of PEG comprises a terminal thiocarboxylic acid group, —COSH, which selectively reacts with amino groups to generate amide derivatives. In other embodiments, the PEG comprises a reactive ester such as an N-hydroxy succinimidate at the end of the PEG chain. Such an N-hydroxysuccinimidate-containing PEG molecule reacts with select amino groups at particular pH conditions such as a neutral pH of around 6.5-7.5.

The PEG can be conjugated directly to an amino acid residue of the polypeptide, or through a linker. In some embodiments, a linker is added to the polypeptide, forming a linker-modified polypeptide. Such linkers provide various functionalities, e.g., reactive groups such as sulfhydryl, amino, or carboxyl groups to couple a PEG reagent to the linker-modified polypeptide.

The PEG that is conjugated to the polypeptide may be linear or branched. Branched PEG derivatives include, but are not limited to, those described in U.S. Pat. No. 5,643,575, "star-PEGs," and multi-armed PEGs such as those described in Shearwater Polymers, Inc. catalog "Polyethylene Glycol Derivatives 1997-1998." Star PEGs are described in the art, e.g., in U.S. Pat. No. 6,046,305.

Polynucleotides Encoding Polypeptides Having a Catalytic Domain of a Lysyl Oxidase-Type Enzyme The present disclosure contemplates a polynucleotide comprising a nucleic acid sequence encoding a polypeptide described previously that has an activity of a lysyl oxidase-type enzyme. The nucleic acid contemplated herein has a nucleotide sequence that is at least 70% identical to (e.g., at least 85%, at least 90%, at least 95%, at least 98%, at least 99% or 100%) to a contiguous sequence of a nucleic acid that encodes any of the polypeptides described above. The percentage identity is based on the shorter of the sequences compared. Well known programs such as BLASTN (2.0.8) (Altschul et al. (1997) Nucl. Acids. Res. 25:3389-3402) using default parameters and no filter can be employed to make a sequence comparison. Nucleic acid sequence identity (e.g. between two different polynucleotides encoding identical amino acid sequences) can be lower than the percent of amino acid sequence identity due to degeneracy of the genetic code.

Examples of nucleic acid sequences in a polynucleotide encoding a polypeptide of the present disclosure include SEQ ID NO:2 (human LOX-derived), SEQ ID NO:4 (human LOX2-derived), SEQ ID NO:6 (murine LOX-derived), and SEQ ID NO:8 (murine LOX2-derived). These nucleic acid sequences can also be provided in an expression vector.

Expression vectors provided herein contain the aforementioned nucleic acids and/or polynucleotides. Such expression vectors can contain promoters (e.g., T7 promoter, T3 promoter, SP6 promoter, E. coli RNA polymerase promoter, CMV promoter, SV40 promoter, PGK promoter, EF-1alpha promoter), transcription termination signals (e.g., SV40 termination signal), splice sites (e.g., SV40 splice sites, beta-globin splice site), ribosome binding sites, signal sequences (e.g., immunoglobulin kappa signal sequence), epitopes tags (e.g., myc, FLAG), purification tags (e.g., $His_6$), replication origins and drug selection markers. Linker sequences, encoding linker amino acids and/or comprising restriction enzyme recognition sites, or any other type of linker sequence, can also be operably linked to the nucleic acid encoding the subject polypeptide present in the vectors disclosed herein. Further details of vectors and uses thereof are described below.

Methods of Making Polypeptides of the Present Disclosure

Polypeptides of the present disclosure can be produced by any suitable method, including recombinant and non-recombinant methods (e.g., chemical synthesis). The subject polypeptide can be prepared by solid-phase synthesis methods well-known in the art, (e.g., Fmoc- or t-Boc chemistry), such as those described by Merrifield (1963) J. Am. Chem. Soc. 85:2149 and Methods in Molecular Biology, Vol 35: Peptide Synthesis Protocols.

Where the polypeptide is produced using recombinant techniques, the methods can involve any suitable construct and any suitable host cell, which can be a prokaryotic or eukaryotic cell (e.g. a bacterial host cell, a yeast host cell, or a cultured mammalian host cell). Methods for introducing genetic material into host cells include, for example, transformation, electroporation, lipofection, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., plasmid) or can be genomically integrated.

Suitable vectors for transferring a polypeptide-encoding nucleic acid can vary in composition. Integrative vectors can be conditionally replicative or suicide plasmids, bacteriophages, and the like. The constructs can include various elements, including for example, promoters, selectable genetic markers (e.g., genes conferring resistance to antibiotics (for instance neomycin, G418, methotrexate, ampicillin kanamycin, erythromycin, chloramphenicol, or gentamycin)), origins of replication (to promote replication in a host cell, e.g., a bacterial host cell), and the like. The choice of vector will depend upon a variety of factors such as the type of cell in which propagation is desired and the purpose of propagation. Certain vectors are useful for amplifying and making large amounts of the desired DNA sequence. Other vectors are suitable for expression of protein in cells in culture. Still other vectors are suitable for transfer and expression in cells in a whole animal. The choice of appropriate vector is well within the skill of the art. Many such vectors are available commercially.

The vector used can be an expression vector based on episomal plasmids containing selectable drug resistance markers and elements that provide for autonomous replication in different host cells. Vectors are amply described in numerous publications well known to those in the art, including, e.g., Short Protocols in Molecular Biology, (1999) F. Ausubel, et al., eds., Wiley & Sons. Vectors may provide for expression of the nucleic acids encoding the subject polypeptide, may provide for propagating the subject nucleic acids, or both.

Constructs can be prepared by, for example, inserting a polynucleotide of interest into a construct backbone, typically by means of DNA ligase attachment to a cleaved restriction enzyme site in the vector. Alternatively, the desired nucleotide sequence can be inserted by homologous recombination or site-specific recombination, or by one or more amplification methods (e.g., PCR). Typically homologous recombination is accomplished by attaching regions of homology to the vector on the flanks of the desired nucleotide sequence, while site-specific recombination can be accomplished through use of sequences that facilitate site-specific recombination (e.g., cre-lox, att sites, etc.). Nucleic acid containing such sequences can be added by, for example, ligation of oligonucleotides, or by polymerase chain reaction using primers comprising both the region of homology and a portion of the desired nucleotide sequence.

For expression of the polypeptide of interest, an expression cassette can be employed. Thus, the present disclosure provides a recombinant expression vector comprising a subject nucleic acid. The expression vector can provide transcriptional and translational regulatory sequences, and can also provide for inducible or constitutive expression, wherein the coding region is operably placed under the transcriptional control of a transcriptional initiation region (e.g., a promoter or enhancer), and transcriptional and translational termination regions. These control regions may be native to a lysyl oxidase-type enzyme from which the subject polypeptide is derived, or may be derived from exogenous sources. As such, control regions from exogenous sources can be considered heterologous elements that are operably linked to the nucleic acid encoding the subject polypeptide. In general, the transcriptional and translational regulatory sequences can include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7, and the like).

Expression vectors generally have convenient restriction sites located near the promoter sequence to provide for the insertion of nucleic acid sequences encoding proteins of interest. A selectable marker operative in the expression host can be present to facilitate selection of cells containing the vector. In addition, the expression construct can include additional elements. For example, the expression vector can have one or two replication systems, thus allowing it to be maintained, for example, in mammalian or insect cells for expression and in a prokaryotic host for cloning and amplification. In addition, the expression construct can contain a selectable marker gene to allow the selection of transformed host cells. Selection genes are well known in the art and will vary with the host cell used.

It should be noted that the polypeptides of the present disclosure can also contain additional elements, such as a detectable label, e.g., a radioactive label, a fluorescent label, a biotin label, an immunologically detectable label (e.g., a hemagglutinin (HA) tag, a poly-Histidine tag) and the like. Additional elements can be provided (e.g., in the form of fusion polypeptides) to facilitate expression (e.g. N-terminal methionine and/or a heterologous signal sequence to facilitate expression in host cells), and/or isolation (e.g., biotin tag, immunologically detectable tag) of the polypeptides of the disclosure through various methods. The polypeptides can also optionally be immobilized on a support through covalent or non-covalent attachment. Exemplary nucleic acids encoding the subject polypeptide can contain SEQ ID NO:10, SEQ ID NO:12, SEQ ID NO:14 or SEQ ID NO:16. The nucleic acid can encode a polypeptide derived from a human or murine lysyl oxidase-type enzyme that has a myc tag, a $His_6$ tag, and/or linker sequences.

Isolation and purification of the subject polypeptides can be accomplished according to methods known in the art. The term "isolated" is intended to mean that a compound (e.g. polypeptide or polynucleotide) is separated from all or some of the components that accompany it in nature. "Isolated" also refers to the state of a compound separated from all or some of the components that accompany it during manufacture (e.g., chemical synthesis, recombinant expression, culture medium, and the like).

For example, a polypeptide according to the present disclosure can be isolated from a lysate of cells that have been genetically modified to express the subject polypeptide, from the supernatant of cell culture medium, or from a synthetic reaction mixture. Isolation can additionally be achieved by immunoaffinity purification, which generally involves contacting a sample with an antibody (optionally immobilized) against an epitope of the polypeptide (e.g., a heterologous epitope fused to an amino acid sequence derived from a lysyl oxidase-type enzyme), washing to remove non-specifically bound material, and eluting specifically bound polypeptide. Isolated polypeptide can be further purified by dialysis and other methods normally employed in protein purification, e.g. metal chelate chromatography, ion-exchange, and size exclusion.

The present disclosure further contemplates recombinant host cells containing an exogenous polynucleotide encoding one or more of the polypeptides of the present disclosure.

Screening Methods

The polypeptides of the present disclosure, having lysyl oxidase catalytic activity, are useful in methods to screen for modulators of the activity of a lysyl oxidase-type enzyme. Expressing an adequate amount of a subject polypeptide as described previously can be used to provide substrate for the screening assays described below.

Modulators of the activity of a lysyl oxidase-type enzyme (and candidate compounds to be tested for modulatory activity) can comprise macromolecules such as, for example proteins (e.g., antibodies, transcription factors) and nucleic acids (e.g., triplex-forming oligonucleotides, antisense oligonucleotides, ribozymes, siRNA, shRNA), and small organic molecules, such as are obtained by synthetic organic methods and/or combinatorial chemistry.

Modulators of the activity of lysyl oxidase-type enzymes include both activators (agonists) and inhibitors (antagonists), and can be selected by using a variety of screening assays. In one embodiment, modulators can be identified by determining if a test compound binds to a catalytic domain polypeptide as disclosed herein; wherein, if binding has occurred, the compound is a candidate modulator. Optionally, additional tests can be carried out on such a candidate modulator. Alternatively, a candidate compound can be contacted with a polypeptide as disclosed herein, and a biological activity of the polypeptide is assayed; a compound that alters the biological activity of the polypeptide is a modulator of a lysyl oxidase-type enzyme. Generally, a compound that reduces a biological activity of the polypeptide is an inhibitor of the enzyme.

Other methods of identifying modulators of the activity of lysyl oxidase-type enzymes include incubating a candidate compound in a cell culture in which the cells are expressing one or more of the polypeptides of the disclosure, and assaying one or more biological activities or characteristics of the cells. Compounds that alter the biological activity or characteristic of the cells in the culture are potential modulators of the activity of a lysyl oxidase-type enzyme. Biological activities that can be assayed include, for example, lysine oxidation, peroxide production, ammonia production, levels of lysyl oxidase-type enzyme, levels of mRNA encoding a lysyl oxidase-type enzyme, levels of a polypeptide of the disclosure, levels of mRNA encoding a polypeptide of the disclosure and/or one or more functions specific to a lysyl oxidase-type enzyme.

In additional embodiments of the aforementioned assay, in the absence of contact with the candidate compound, the one or more biological activities or cell characteristics are correlated with levels or activity of one or more lysyl oxidase-type enzymes. For example, the biological activity can be a cellular function such as migration, chemotaxis, epithelial-to-mesenchymal transition (EMT), or mesenchymal-to-epithelial transition (MET), and the change is detected by comparison with one or more control or reference sample(s).

Controls can also be used. As an example, negative control samples can include a culture with decreased levels of a polypeptide of the disclosure (or a culture which does not express a polypeptide of the disclosure), to which a candidate compound is added; or a culture with the same amount of a polypeptide of the disclosure as the test culture, but without addition of candidate compound. A control can include the addition of a mock candidate compound or an agent known to activate or inhibit lysyl oxidase activity. In some embodiments, separate cultures containing different levels of a polypeptide of the disclosure are contacted with a candidate compound. If a change in biological activity is observed, and if the change is greater in the culture having higher levels of the polypeptide, the compound is identified as a modulator of the activity of a lysyl oxidase-type enzyme. Determination of whether the compound is an activator or an inhibitor of a lysyl oxidase-type enzyme may be apparent from the phenotype induced by the compound, or may require further assay, such as a test of the effect of the compound on the enzymatic activity of one or more lysyl oxidase-type enzymes.

Methods for obtaining lysysl oxidase-type enzymes, either biochemically or recombinantly, as well as methods for cell culture and enzymatic assay to identify modulators of the activity of lysyl oxidase-type enzymes as described above, are known in the art.

The enzymatic activity of a lysyl oxidase-type enzyme can be assayed by a number of different methods. For example, lysyl oxidase enzymatic activity can be assessed by detecting and/or quantitating production of hydrogen peroxide, ammonium ion, and/or aldehyde, by assaying lysine oxidation and/or collagen crosslinking, or by measuring cellular invasive capacity, cell adhesion, cell growth or metastatic growth. See, for example, Trackman et al. (1981) *Anal. Biochem.* 113:336-342; Kagan et al. (1982) *Meth. Enzymol.* 82A:637-649; Palamakumbura et al. (2002) *Anal. Biochem.* 300:245-251; Albini et al. (1987) *Cancer Res.* 47:3239-3245; Kamath et al. (2001) *Cancer Res.* 61:5933-5940; U.S. Pat. No. 4,997,854 and U.S. patent application publication No. 2004/0248871.

Test compounds include, but are not limited to, small organic compounds (e.g., organic molecules having a molecular weight between about 50 and about 2,500 Da), nucleic acids or proteins, for example. The compound or plurality of compounds can be chemically synthesized or microbiologically produced and/or comprised in, for example, samples, e.g., cell extracts from, e.g., plants, animals or microorganisms. The reaction mixture for assaying for a modulator of a lysyl oxidase-type enzyme can be a cell-free extract or can comprise a cell culture or tissue culture. A plurality of compounds can be, e.g., added to a reaction mixture, added to a culture medium, injected into a cell or administered to a transgenic animal. The cell or tissue employed in the assay can be, for example, a bacterial cell, a fungal cell, an insect cell, a vertebrate cell, a mammalian cell, a primate cell, a human cell or can comprise or be obtained from a non-human transgenic animal.

If a sample containing a compound or a plurality of compounds is identified in the method of the disclosure, then it is either possible to isolate the compound from the original sample identified as containing the compound capable of inhibiting or activating the subject polypeptide, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times (e.g., by limiting dilution), until the sample identified according to the method of the disclosure only comprises a limited number of or only one substance(s). In some embodiments the sample comprises substances of similar chemical and/or physical properties, and in some embodiments, the substances are identical.

Furthermore, the above-mentioned methods can be used for the construction of binding epitopes derived from a lysyl oxidase-type enzyme. A similar approach was successfully described for peptide antigens of the anti-p24 (HIV-1) monoclonal antibody; see Kramer (1997) *Cell* 97:799-809. A general route to fingerprint analyses of peptide-antibody interactions using the clustered amino acid peptide library was described in Kramer (1995) *Mol. Immunol.* 32:459-465. In addition, antagonists of lysyl oxidase-type enzymes can be derived and identified from monoclonal antibodies that specifically react with the polypeptide of the disclosure in accordance with the methods as described in Doring (1994) *Mol. Immunol.* 31:1059-1067.

Several methods are known to the person skilled in the art for producing and screening large libraries to identify compounds having specific affinity for a target, such as a lysyl oxidase-type enzyme or a polypeptide of the disclosure. These methods include phage display method in which randomized peptides are displayed from phage and screened by affinity chromatography using an immobilized receptor. See, e.g., WO 91/17271, WO 92/01047, and U.S. Pat. No. 5,223,409. In another approach, combinatorial libraries of polymers immobilized on a solid support (e.g., a "chip") are synthesized using photolithography. See, e.g., U.S. Pat. No. 5,143,854, WO 90/15070 and WO 92/10092. The immobilized polymers are contacted with a labeled polypeptide (e.g., a lysyl oxidase-type enzyme or a polypeptide as disclosed herein) and the support is scanned to determine the location of label, to thereby identify polymers binding to the polypeptide.

The synthesis and screening of peptide libraries on continuous cellulose membrane supports that can be used for identifying binding ligands (e.g., activators or inhibitors) of a polypeptide of interest (e.g., a lysyl oxidase-type enzyme or a polypeptide of the disclosure) is described, for example, in Kramer (1998) *Methods Mol. Biol.* 87: 25-39. Ligands identified by such an assay are candidate modulators of the protein of interest, and can be selected for further testing. This method can also be used, for example, for determining the binding sites and the recognition motifs in a protein of interest. See, for example Rudiger (1997) *EMBO J.* 16:1501-1507 and Weiergraber (1996) *FEBS Lett.* 379:122-126.

WO 98/25146 describes additional methods for screening libraries of complexes for compounds having a desired property, e.g., the capacity to agonize, bind to, or antagonize a polypeptide or its binding partners. The complexes in such libraries comprise a compound under test, a tag recording at least one step in synthesis of the compound, and a tether susceptible to modification by a reporter molecule. Modification of the tether is used to signify that a complex contains a compound having a desired property. The tag can be decoded to reveal at least one step in the synthesis of such a compound. Other methods for identifying compounds which interact with a lysyl oxidase-type enzyme (or with the polypeptides of the disclosure) are, for example, in vitro screening with a phage display system, filter binding assays, and "real time" measuring of interaction using, for example, the BIAcore apparatus (Pharmacia).

All these methods can be used in accordance with the present disclosure to identify activators/agonists and inhibitors/antagonists of lysyl oxidase-type enzymes or related polypeptides.

Various sources for the basic structure of such an activator or inhibitor can be employed and comprise, for example, mimetic analogs of the polypeptides of the disclosure. Mimetic analogs of the polypeptide of the disclosure or biologically active fragments thereof can be generated by, for example, substituting the amino acids that are expected to be essential for the biological activity with, e.g., stereoisomers, i.e. D-amino acids; see e.g., Tsukida (1997) *J. Med. Chem.* 40:3534-3541. Furthermore, for cases in which polypeptide fragments are used for the design of biologically active analogues, pro-mimetic components can be incorporated into a peptide to reestablish at least some of the conformational properties that may have been lost upon removal of part of the original polypeptide; see, e.g., Nachman (1995) *Regul. Pept.* 57:359-370.

Such pseudopeptide analogues of a natural amino acid sequence can very efficiently mimic the parent protein. Benkirane (1996) *J. Biol. Chem.* 271:33218-33224. For example, incorporation of easily available achiral o-amino acid residues into a polypeptide of the disclosure or a fragment thereof results in the substitution of amide bonds by polymethylene units of an aliphatic chain, thereby providing a convenient strategy for constructing a peptide mimetic. Banerjee (1996) *Biopolymers* 39:769-777. Superactive peptidomimetic analogues of small peptide hormones in other systems have also been described. Zhang (1996) *Biochem. Biophys. Res. Commun.* 224:327-331.

Peptide mimetics can also be identified by the synthesis of peptide mimetic combinatorial libraries through successive amide alkylation, followed by testing of the resulting compounds, e.g., for their binding and immunological properties. Methods for the generation and use of peptidomimetic combinatorial libraries have been described. See, for example, Ostresh, (1996) *Methods in Enzymology* 267:220-234 and Dorner (1996) *Bioorg. Med. Chem.* 4:709-715. Furthermore, a three-dimensional and/or crystallographic structure of a polypeptide of the disclosure can be used for the design of peptide mimetics. Rose (1996) *Biochemistry* 35:12933-12944; Rutenber (1996) *Bioorg. Med. Chem.* 4:1545-1558.

The structure-based design and synthesis of low-molecular-weight synthetic molecules that mimic the activity of native biological polypeptides is further described in, e.g., Dowd (1998) *Nature Biotechnol.* 16:190-195; Kieber-Emmons (1997) *Current Opinion Biotechnol.* 8:435-441; Moore (1997) *Proc. West Pharmacol. Soc.* 40:115-119; Mathews (1997) *Proc. West Pharmacol. Soc.* 40:121-125; and Mukhija (1998) *European J. Biochem.* 254:433-438.

It is also well known to the person skilled in the art that it is possible to design, synthesize and evaluate mimetics of small organic compounds that, for example, can act as a substrate or ligand of a lysyl oxidase-type enzyme or of a polypeptide of the disclosure. For example, it has been described that D-glucose mimetics of hapalosin exhibited similar efficiency as hapalosin in antagonizing multidrug resistance assistance-associated protein in cytotoxicity. Dinh (1998) *J. Med. Chem.* 41:981-987.

The structure of the lysyl oxidase-type enzymes, and of the polypeptides disclosed herein, can be investigated to guide the selection of modulators such as, for example, small molecules, peptides, peptide mimetics and antibodies. Structural properties of lysyl oxidase-type enzymes, and of the polypeptides of the disclosure, can help to identify natural or synthetic molecules that bind to, or function as a ligand, substrate, binding partner or the receptor of, a lysyl oxidase-type enzyme. See, e.g., Engleman (1997) *J. Clin. Invest.* 99:2284-2292. For example, folding simulations and computer redesign of structural motifs of lysyl oxidase-type enzymes can be performed using appropriate computer programs. Olszewski (1996) *Proteins* 25:286-299; Hoffman (1995) *Comput. Appl. Biosci.* 11:675-679. Computer modeling of protein folding can be used for the conformational and energetic analyses of detailed peptide and protein structure. Monge (1995) *J. Mol. Biol.* 247:995-1012; Renouf (1995) *Adv. Exp. Med. Biol.* 376:37-45. Appropriate programs can be used for the identification of sites, on lysyl oxidase-type enzymes and/or on the polypeptides of the disclosure, that interact with ligands and binding partners, using computer assisted searches for complementary peptide sequences. Fassina (1994) *Immunomethods* 5:114-120. Additional systems for the design of protein and peptides are described in the art, for example in Berry (1994) *Biochem. Soc. Trans.* 22:1033-1036; Wodak (1987), *Ann. N.Y. Acad. Sci.* 501:1-13; and Pabo (1986) *Biochemistry* 25:5987-5991. The results obtained from the above-described structural analyses can be used for, e.g., the preparation of organic molecules, peptides and peptide mimetics that function as modulators of the activity of one or more lysyl oxidase-type enzymes, and for the preparation of mimetics of the polypeptides of the disclosure.

The inhibitors to be screened herein, such as antibodies, can be competitive inhibitors, uncompetitive inhibitors, mixed inhibitors or non-competitive inhibitors. Competitive inhibitors often bear a structural similarity to substrate, usually bind to the active site and are generally more effective at lower substrate concentrations. The apparent $K_M$ is increased in the presence of a competitive inhibitor. Uncompetitive inhibitors generally bind to the enzyme-substrate complex or to a site that becomes available after substrate is bound at the active site and may distort the active site. Both the apparent $K_M$ and the $V_{max}$ are decreased in the presence of an uncompetitive inhibitor, and substrate concentration has little or no effect on inhibition. Thus, inhibition by an uncompetitive inhibitor is often most noticeable at high substrate concentration. Mixed inhibitors are capable of binding both to free enzyme and to the enzyme-substrate complex and thus affect both substrate binding and catalytic activity. Non-competitive inhibition is a special case of mixed inhibition in which the inhibitor binds enzyme and enzyme-substrate complex with equal avidity, and inhibition is not affected by substrate concentration. Non-competitive inhibitors generally bind to enzyme at a region outside the active site. For additional details on enzyme inhibition see, for example, Voet et al. (2008) supra. For enzymes such as the lysyl oxidase-type enzymes, whose natural substrates (e.g., collagen, elastin) are normally present in vast excess in vivo (compared to the concentration of any inhibitor that can be achieved in vivo), noncompetitive inhibitors are advantageous, since inhibition is independent of substrate concentration.

Antibody Production

The present disclosure also provides a method of producing antibodies specific for the polypeptides of the disclosure. The antibody can be isolated, e.g., is in an environment other than its naturally-occurring environment. Suitable antibodies specific for the subject polypeptide include antibodies of any isotype; single-chain Fv; Fab; Fab; Fv; F(ab')$_2$; artificial antibodies; humanized antibodies; fragments thereof, and the like.

Suitable antibodies can be obtained by immunizing a host animal with peptides comprising all or a portion of a subject polypeptide. Where an animal is to be immunized, the present disclosure provides an immunogenic composition comprising a subject polypeptide. A subject immunogenic composition may include a subject polypeptide and an adjuvant. Adjuvants are known in the art and may include those suitable for use in humans or other mammals.

Suitable host animals to be immunized include mouse, rat sheep, goat, hamster, rabbit, donkey, etc. Methods of immunizing animals, including the adjuvants used, booster schedules, sites of injection, suitable animals, etc. are well understood in the art (e.g., Harlow et al., *Antibodies: A Laboratory Manual*, First Edition (1988) Cold Spring Harbor, N.Y.), and administration of living cells to animals has been described for several mammals and birds, e.g., McKenzie et al. (1989) *Oncogene* 4:543-548; Scuderi et al. (1985) *Med. Oncol. Tumor Pharmacother* 2:233-242; Roth et al. (1984) *Surgery* 96:264-272 and Drebin et al. (1984) *Nature* 312:545-548. Subsequent to immunization, a population of antibody producing cells is generated. The population of cells may be produced using hybridoma methods that are well known to one of skill in the art (see, e.g., Harlow, supra. Cells expressing antibody are fused to immortalized cells, such as myeloma cells or transformed cells, which are capable of replicating indefinitely in cell culture, thereby producing an immortal, immunoglobulin-secreting cell line. The immortal cell line utilized can be selected to be deficient in enzymes necessary for the utilization of certain nutrients. Many such lines (such as myelomas) are known to those skilled in the art, and include, for example: thymidine kinase (TK)-deficient or hypoxanthine-guanine phosphoriboxyl transferase (HG-PRT)-deficient cell lines. These deficiencies allow selection for fused cells according to their ability to grow on, for example, hypoxanthine/aminopterin/thymidine (HAT) medium. In alterative embodiments, populations of cells expressing monoclonal antibodies can be made using phage display methods.

Antibodies against the subject polypeptides can also be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library can be constructed by combining the heavy chain gene library with the light chain gene library. This results in a library of clones which co-express a heavy and light chain (resembling the F$_{ab}$ fragment or antigen binding fragment of an antibody molecule). The vectors that carry these genes are co-transfected into a host (e.g. bacteria, insect cells, mammalian cells, or other suitable protein production host cell). When antibody gene synthesis is induced in the transfected host, the heavy and light chain proteins self-assemble to produce active antibodies that can be detected by screening with the antigen or immunogen.

Another method of antibody production involves phage display. Phage display is used for high-throughput screening of protein interactions. In this method, phage are utilized to display antigen-binding domains expressed from a repertoire or combinatorial antibody library (e.g., human or murine). Phage expressing an antigen binding domain that binds the subject polypeptide of interest are selected or identified using the polypeptide target, e.g., using labeled polypeptide or polypeptide bound to or captured on a solid surface or bead. Phage used in these methods are typically filamentous phage including fd and M13. The binding domains can comprise F$_{ab}$, F$_v$ (individual F$_v$ region from light or heavy chains) or disulfide stabilized F$_v$ antibody domains recombinantly fused to either the phage gene III or gene VIII protein. Exemplary methods are set forth, for example, in EP 368684B1; U.S. Pat. No. 5,969,108, Hoogenboom, H. R. and Chames (2000) *Immunol. Today* 21:371; Nagy et al. (2002) *Nat. Med.* 8:801; Huie et al. (2001) *Proc. Natl. Acad. Sci. USA* 98:2682; Lui et al. (2002) *J. Mol. Biol.* 315:1063, each of which is incorporated herein by reference. Several publications (e.g., Marks et al. (1992) *Bio/Technology* 10:779-783) have described the production of high-affinity human antibodies by chain shuffling, as well as combinatorial infection and in vivo recombination as a strategy for constructing large phage libraries.

In related embodiments, ribosomal display can be used as a display platform. See, e.g., Hanes et al. (2000) *Nat. Biotechnol.* 18:1287; Wilson et al. (2001) *Proc. Natl. Acad. Sci. USA* 98:3750; and Irving et al. (2001) *J. Immunol. Methods* 248:31).

Cell surface libraries can be screened for antibodies (Boder et al. (2000) *Proc. Natl. Acad. Sci. USA* 97:10701; Daugherty et al. (2000) *J. Immunol. Methods* 243:211. Such procedures provide alternatives to traditional hybridoma techniques for the isolation and subsequent cloning of monoclonal antibodies.

In phage display methods, functional antibody domains are displayed on the surface of phage particles which carry the polynucleotide sequences encoding them. For example, DNA sequences encoding heavy chain variable (V$_H$) and light chain variable (V$_L$) regions are amplified or otherwise isolated from animal cDNA libraries (e.g., human or murine cDNA libraries of lymphoid tissues) or synthetic cDNA libraries. The DNA encoding the V$_H$ and V$_L$ regions may be joined together by an scFv linker (e.g., by PCR) and cloned into a phagemid vector (e.g., pCANTAB 6 or pComb 3 HSS). The vector is electroporated into *E. coli* and the *E. coli* is infected with helper phage. Sequences encoding the V$_H$ or V$_L$ regions are usually recombinantly fused to either gene III or gene VIII sequences of the phage. Phage expressing an antigen binding domain that binds to an antigen of interest (i.e., a subject polypeptide) can be selected or identified with antigen, e.g., using labeled antigen or antigen bound to or captured on a solid surface or bead.

Additional examples of phage display methods include those disclosed in PCT Application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

Formulations, Kits and Routes of Administration

Therapeutic compositions comprising catalytic domains as disclosed herein are also provided. Such compositions typically comprise the catalytic domain (or a nucleic acid encoding the catalytic domain) and a pharmaceutically acceptable carrier. Supplementary active compounds can also be incorporated into the compositions.

As used herein, the term "therapeutically effective amount" or "effective amount" refers to an amount of a therapeutic agent that when administered alone or in combination with another therapeutic agent to a cell, tissue, or subject (e.g., a mammal such as a human or a non-human animal such as a primate, rodent, cow, horse, pig, sheep, etc.) is effective to prevent or ameliorate the disease condition or the progression of the disease. A therapeutically effective dose further refers to that amount of the compound sufficient to result in full or partial amelioration of symptoms, e.g., treatment, healing, prevention or amelioration of the relevant medical condition, or an increase in rate of treatment, healing, prevention or amelioration of such conditions. An effective amount of an agent is an amount that, when administered, in one or more doses, results in an at least about 5%, at least about 10%, at least about 15%, at least about 20%, at least about 25%, at least about 30%, at least about 40%, at least about 50%, at least about 60%, at least about 70%, at least about 80%, at least about 90%, or more than 90%, reduction in the severity of one or more symptoms associated with a lysyl oxidase-type enzyme in an individual, compared to the severity of the one or more symptoms in the absence of treatment with the agent. Such reduction in severity can be manifested, for example, by improved wound healing or enhanced angiogenesis.

A therapeutically effective amount of a catalytic domain of a lysyl oxidase-type enzyme (e.g., a LOX or LOXL2 catalytic domain) varies with the type of disease or disorder, extensiveness of the disease or disorder, and size of the mammal suffering from the disease or disorder.xx Various pharmaceutical compositions and techniques for their preparation and use are known to those of skill in the art in light of the present disclosure. For a detailed listing of suitable pharmacological compositions and techniques for their administration one may refer to texts such as Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington: The Principles of Pharmacy Practice," Lippincott Williams & Wilkins, 2008.

The disclosed therapeutic compositions further include pharmaceutically acceptable materials, compositions or vehicle, such as a liquid or solid filler, diluent, excipient, solvent or encapsulating material, i.e., carriers. These carriers are involved in transporting the subject composition from one organ, or region of the body, to another organ, or region of the body. Each carrier should be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Another aspect of the present disclosure relates to kits for carrying out the administration of a catalytic domain of a lysyl oxidase-type enzyme, as disclosed herein, or of a nucleic acid encoding such a catalytic domain, to a subject. In one embodiment, the kit comprises a catalytic domain of a lysyl oxidase-type enzyme (or a nucleic acid encoding a catalytic domain of a lysyl oxidase-type enzyme), formulated in a pharmaceutical carrier.

The formulation and delivery methods are generally adapted according to the site(s) and type of disorder to be treated. Exemplary formulations include, but are not limited to, those suitable for parenteral administration, e.g., intravenous, intra-arterial, intra-ocular, intramuscular, or subcutaneous administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays. The dosage of the compounds of the disclosure will vary according to the extent and severity of the need for treatment, the activity of the administered composition, the general health of the subject, and other considerations well known to the skilled artisan.

In additional embodiments, the compositions described herein are delivered locally. Localized delivery allows for the delivery of the composition non-systemically, for example, to a wound or fibrotic area, reducing the body burden of the composition as compared to systemic delivery. Such local delivery can be achieved, for example, through the use of various medically implanted devices including, but not limited to, stents and catheters, or can be achieved by injection or surgery. Methods for coating, implanting, embedding, and otherwise attaching desired agents to medical devices such as stents and catheters are established in the art and contemplated herein.

Implanted stents have been used to carry medicinal agents, such as thrombolytic agents. U.S. Pat. No. 5,163,952 discloses a thermal memoried expanding plastic stent device formulated to carry a medicinal agent in the material of the stent itself. U.S. Pat. No. 5,092,877 discloses a stent of a polymeric material which can have a coating associated with the delivery of compounds. Other patents which are directed to devices of the class utilizing bio-degradable and bio-sorbable polymers include U.S. Pat. No. 4,916,193 and U.S. Pat. No. 4,994,071. By way of example, U.S. Pat. No. 5,304,121 discloses a coating applied to a stent consisting of a hydrogel polymer and a preselected compound such as a cell growth inhibitor or heparin. Methods of making a coated intravascular stent carrying a therapeutic material are described in U.S. Pat. No. 5,464,650 wherein a polymer coating material is dissolved in a solvent and the therapeutic material dispersed in the solvent. The solvent is then evaporated after contact with the stent.

U.S. Pat. No. 6,120,536 describes additional types of coatings for use with a wide variety of prosthetic devices, including stents. Examples of additional medical or prosthetic devices that are useful for administration of the compositions described herein include, but are not limited to, blood exchanging devices, vascular access ports, central venous catheters, cardiovascular catheters, extracorporeal circuits, vascular grafts, pumps, heart valves, and cardiovascular sutures.

The use of devices coated with the compositions described herein, including stents and catheters, allows the compositions to be delivered to specific or localized sites. Such site-specific delivery can provide a means for use of compositions, and/or dosages thereof, that are not otherwise amenable to systemic delivery due to solubility, systemic toxicity concerns, or other issues. By way of example, β-aminopropionitrile (BAPN) is known to be useful as an inhibitor of lysyl oxidase-type enzymes, but this compound is highly toxic, presenting problems for its effective use when administered systemically. The use of a stent, catheter, or other medical device for delivery of an active agent or compound such as BAPN permits use of the compound at effective dosages in a targeted or localized manner, thus decreasing the systemic toxic effects associated with such compounds.

Uses

The polypeptides disclosed herein have a number of uses. For example, they can be used as standards (e.g., positive controls) for assays of lysyl oxidase enzymatic activity (e.g., collagen crosslinking). One use for such an assay is in a mutational analysis of, e.g., a LOX or LOXL2 protein and/or its gene. The polypeptides, comprising catalytic domains with lysyl oxidase activity, can also be used to characterize new and existing antibodies to lysyl oxidase-type enzymes.

The polypeptides disclosed herein can also be used to identify molecules that bind to, e.g., LOX and/or LOXL2 catalytic domains, e.g., small organic molecules or macromolecules (e.g., polypeptides). Certain of these binding molecules may act as modulators (i.e., activators or inhibitors) of catalytic activity.

The subject polypeptides disclosed herein are also useful for generation of antibodies directed specifically to the catalytically active region of human and murine LOX and LOXL2 proteins and other lysyl oxidase-type enzymes. Such antibodies can be used, for example, in medical and/or therapeutic applications for diseases or disorders characterized by pathologically increased levels of lysyl oxidase activity.

In addition, the subject polypeptides are useful in medical and/or therapeutic applications requiring crosslinking of collagen: for example wound healing and treatment of diabetic ulcers. The smaller size of the isolated catalytic domains (compared to the full-length proteins) may facilitate their use as therapeutics, due, for example, to enhanced stability and faster absorption.

EXAMPLES

Example 1

Human LOX Catalytic Domain

A polypeptide including the catalytic domain of the human LOX protein contains 207 amino acid residues and has the following amino acid sequence:

```
                                              (SEQ ID NO: 1)
GLPDLVADPYYIQASTYVQKMSMYNLRCAAEENCLASTAYRADVRDYDHR

VLLRFPQRVKNQGTSDFLPSRPRYSWEWHSCHQHYHSMDEFSHYDLLDAN

TQRRVAEGHKASFCLEDTSCDYGYHRRFACTAHTQGLSPGCYDTYGADID

CQWIDITDVKPGNYILKVSVNPSYLVPESDYTNNVVRCDIRYTGHHAYAS

GCTISPY
```

In certain embodiments, a polypeptide including the human LOX catalytic domain does not include the initial glycine and leucine residues ("GL") in the sequence shown above.

The human DNA sequence encoding a subject polypeptide containing the LOX catalytic domain is:

```
                                              (SEQ ID NO: 2)
GGTCTCCCAGACCTGGTGGCCGACCCCTACTACATCCAGGCGTCCACGTA

CGTGCAGAAGATGTCCATGTACAACCTGAGATGCGCGGCGGAGGAAAACT

GTCTGGCCAGTACAGCATACAGGGCAGATGTCAGAGATTATGATCACAGG

GTGCTGCTCAGATTTCCCCAAAGAGTGAAAAACCAAGGGACATCAGATTT

CTTACCCAGCCGACCAAGATATTCCTGGGAATGGCACAGTTGTCATCAAC

ATTACCACAGTATGGATGAGTTTAGCCACTATGACCTGCTTGATGCCAAC

ACCCAGAGGAGAGTGGCTGAAGGCCACAAAGCAAGTTTCTGTCTTGAAGA

CACATCCTGTGACTATGGCTACCACAGGCGATTTGCATGTACTGCACACA

CACAGGGATTGAGTCCTGGCTGTTATGATACCTATGGTGCAGACATAGAC

TGCCAGTGGATTGATATTACAGATGTAAAACCTGGAAACTATATCCTAAA

GGTCAGTGTAAACCCCAGCTACCTGGTTCCTGAATCTGACTATACCAACA

ATGTTGTGCGCTGTGACATTCGCTACACAGGACATCATGCGTATGCCTCA

GGCTGCACAATTTCACCGTATTAG
```

Example 2

Human LOXL2 Catalytic Domain

A polypeptide including the catalytic domain of the human LOXL2 protein has the following amino acid sequence:

```
                                              (SEQ ID NO: 3)
TAPDLVLNAEMVQQTTYLEDRPMFMLQCAMEENCLSASAAQTDPTTGYRR

LLRFSSQIHNNGQSDFRPKNGRHAWIWHDCHRHYHSMEVFTHYDLLNLNG

TKVAEGHKASFCLEDTECEGDIQKNYECANFGDQGITMGCWDMYRHDIDC

QWVDITDVPPGDYLFQVVINPNFEVAESDYSNNIMKCRSRYDGHRIWMYN

CHIGGSFSEETEKKFEHFSGLLNNQLSPQ
```

In certain embodiments, a polypeptide including the human LOXL2 catalytic domain does not include the initial threonine and alanine residues ("TA") in the sequence shown above.

The human DNA sequence encoding the LOXL2 catalytic domain is:

```
                                             (SEQ ID NO: 4)
ACCGCCCCTGACCTGGTCCTCAATGCGGAGATGGTGCAGCAGACCACCTA

CCTGGAGGACCGGCCCATGTTCATGCTGCAGTGTGCCATGGAGGAGAACT

GCCTCTCGGCCTCAGCCGCGCAGACCGACCCCACCACGGGCTACCGCCGG

CTCCTGCGCTTCTCCTCCCAGATCCACAACAATGGCCAGTCCGACTTCCG

GCCCAAGAACGGCCGCCACGCGTGGATCTGGCACGACTGTCACAGGCACT

ACCACAGCATGGAGGTGTTCACCCACTATGACCTGCTGAACCTCAATGGC

ACCAAGGTGGCAGAGGGCCACAAGGCCAGCTTCTGCTTGGAGGACACAGA

ATGTGAAGGAGACATCCAGAAGAATTACGAGTGTGCCAACTTCGGCGATC

AGGGCATCACCATGGGCTGCTGGGACATGTACCGCCATGACATCGACTGC

CAGTGGGTTGACATCACTGACGTGCCCCCTGGAGACTACCTGTTCCAGGT

TGTTATTAACCCCAACTTCGAGGTTGCAGAATCCGATTACTCCAACAACA

TCATGAAATGCAGGAGCCGCTATGACGGCCACCGCATCTGGATGTACAAC

TGCCACATAGGTGGTTCCTTCAGCGAAGAGACGGAAAAAAAGTTTGAGCA

CTTCAGCGGGCTCTTAAACAACCAGCTGTCCCCGCAGTAA
```

Example 3

Murine LOX Catalytic Domain

A polypeptide including the catalytic domain of the murine LOX protein has the following amino acid sequence:

```
                                             (SEQ ID NO: 5)
GLPDLVPDPYYIQASTYVQKMSMYNLRCAAEENCLASSAYRADVRDYDHR

VLLRFPQRVKNQGTSDFLPSRPRYSWEWHSCHQHYHSMDEFSHYDLLDAN

TQRRVAEGHKASFCLEDTSCDYGYHRRFACTAHTQGLSPGCYDTYAADID

CQWIDITDVQPGNYILKVSVNPSYLVPESDYTNNVVRCDIRYTGHHAYAS

GCTISPY
```

In certain embodiments, a polypeptide including the murine LOX catalytic domain does not include the initial glycine and leucine residues ("GL") in the sequence shown above.

The murine DNA sequence encoding a polypeptide including the LOX catalytic domain is:

```
                                             (SEQ ID NO: 6)
GGTCTCCCGGACCTGGTGCCCGACCCCTACTACATCCAGGCTTCCACGTA

CGTCCAGAAGATGTCTATGTACAACCTGAGATGCGCTGCGGAAGAAAACT

GCCTGGCCAGTTCAGCATATAGGGCGGATGTCAGAGACTATGACCACAGG

GTACTGCTACGATTTCCGCAAAGAGTGAAGAACCAAGGGACATCGGACTT

CTTACCAAGCCGCCCTCGGTACTCCTGGGAGTGGCACAGCTGTCACCAAC
```

ATTACCACAGCATGGACGAATTCAGCCACTATGACCTGCTTGATGCCAAC

ACACAGAGGAGAGTGGCTGAAGGCCACAAAGCAAGCTTCTGTCTGGAGGA

CACGTCCTGTGACTATGGGTACCACAGGCGCTTTGCGTGCACTGCACACA

CACAGGGATTGAGTCCTGGATGTTATGACACCTATGCGGCAGACATAGAC

TGCCAGTGGATTGATATTACAGATGTACAACCTGGAAACTACATTCTAAA

GGTCAGTGTAAACCCCAGCTACCTGGTGCCTGAATCAGACTACACTAACA

ATGTTGTACGCTGTGACATTCGCTACACAGGACATCATGCCTATGCCTCA

GGCTGCACAATTTCACCGTATTAG

Example 4

Murine LOXL2 Catalytic Domain

A polypeptide including the catalytic domain of the murine LOXL2 protein has the following amino acid sequence:

```
                                             (SEQ ID NO: 7)
TAPDLVLNAEIVQQTAYLEDRPMSLLQCAMEENCLSASAVHTDPTRGHRR

LLRFSSQIHNNGQSDFRPKNGRHAWIWHDCHRHYHSMEVFTYYDLLSLNG

TKVAEGHKASFCLEDTECEGDIQKSYECANFGEQGITMGCWDMYRHDIDC

QWIDITDVPPGDYLFQVVINPNYEVPESDFSNNIMKCRSRYDGYRIWMYN

CHVGGAFSEETEQKFEHFSGLLNNQLSVQ
```

In certain embodiments, a polypeptide including the murine LOXL2 catalytic domain does not include the initial threonine and alanine residues ("TA") in the sequence shown above.

The murine DNA sequence encoding a polypeptide including the LOXL2 catalytic domain is:

```
                                             (SEQ ID NO: 8)
ACTGCACCTGACCTGGTGCTTAATGCTGAGATTGTCCAGCAGACTGCCTA

CCTGGAGGACAGGCCCATGTCCTTGCTGCAGTGTGCCATGGAGGAGAACT

GCCTCTCCGCCTCCGCTGTGCACACCGACCCCACCAGAGGCCACCGGCGC

CTTTTACGCTTCTCCTCCCAGATCCACAACAATGGCCAGTCTGACTTCCG

CCCCAAGAATGGCCGCCATGCGTGGATTTGGCACGACTGCCACAGGCACT

ACCACAGCATGGAAGTCTTCACTTACTATGACCTGCTGAGCCTCAACGGC

ACCAAGGTGGCTGAGGGCCACAAGGCCAGCTTCTGCCTGGAGGACACTGA

GTGTGAGGGAGACATTCAGAAGAGTTACGAGTGTGCCAACTTTGGAGAAC

AAGGCATCACCATGGGCTGCTGGGACATGTACCGTCATGACATTGACTGC

CAGTGGATAGACATCACCGATGTGCCCCCTGGAGACTACCTGTTCCAGGT

TGTCATTAACCCCAACTATGAAGTGCCAGAATCAGATTTCTCTAACAACA

TCATGAAGTGCAGGAGCCGCTATGATGGCTACCGCATCTGGATGTACAAC

TGTCACGTAGGTGGAGCCTTCAGTGAGGAGACAGAACAGAAGTTCGAACA

CTTCAGTGGACTTCTAAATAACCAGCTCTCTGTACAGTAA
```

Example 5

Expression of Human LOX Catalytic Domain in Mammalian Cells

An expression cassette that is used for the expression of a polypeptide including the human LOX catalytic domain was constructed by PCR amplification, using a human LOX cDNA as template (GenBank NM_002317, obtained from Genecopoeia, Germantown, Md.). The amplification product, containing sequences encoding the catalytic domain, was cloned into the pSecTag2/Hygro B vector (Invitrogen, Carlsbad, Calif.), generating the pSecTag2hygro-hLOX MCD (also referred to as phLOXMCD) plasmid. Transcription of this clone with T7 RNA polymerase generates a mRNA encoding a polypeptide containing (in N-terminal to C-terminal order) an Immunoglobulin kappa signal sequence, the human LOX catalytic domain, a myc epitope tag and a His$_6$ purification tag. This polypeptide has the following amino acid sequence:

(SEQ ID NO: 9)
METDTLLLWVLLLWVPGSTGD*AAQPAGLPDLVADPYYIQASTYVQKMSMY*

NLRCAAEENCLASTAYRADVRDYDHRVLLRFPQRVKNQGTSDFLPSRPRY

SWEWHSCHQHYHSMDEFSHYDLLDANTQRRVAEGHKASFCLEDTSCDYGY

HRRFACTAHTQGLSPGCYDTYGADIDCQWIDITDVKPGNYILKVSVNPSY

LVPESDYTNNVVRCDIRYTGHHAYASGCTISPYG*PEQKLISEEDL*NSAVD

HHHHHH

The sequences of the signal peptide and myc tag are underlined. The italicized sequences represent amino acid sequences encoded in whole or part by vector sequences and restriction sites used in the cloning (AAQP and GP) and a linker sequence (NSAVD).

The DNA sequence encoding this polypeptide (with underlined sequences denoting nucleotides encoding the signal sequence and the myc tag, and linker sequences indicated in lower-case type) is:

(SEQ ID NO: 10)
ATGGAGACAGACACACTCCTGCTATGGGTACTGCTGCTCTGGGTTC

CAGGTTCCACTGGTGACgcggcccagccggccGGTCTCCCAGACCTGGTG

GCCGACCCCTACTACATCCAGGCGTCCACGTACGTGCAGAAGATGTCCAT

GTACAACCTGAGATGCGCGGCGGAGGAAAACTGTCTGGCCAGTACAGCAT

ACAGGGCAGATGTCAGAGATTATGATCACAGGGTGCTGCTCAGATTTCCC

CAAAGAGTGAAAAACCAAGGGACATCAGATTTCTTACCCAGCCGACCAAG

ATATTCCTGGGAATGGCACAGTTGTCATCAACATTACCACAGTATGGATG

AGTTTAGCCACTATGACCTGCTTGATGCCAACACCCAGAGGAGAGTGGCT

GAAGGCCACAAAGCAAGTTTCTGTCTTGAAGACACATCCTGTGACTATGG

CTACCACAGGCGATTTGCATGTACTGCACACACAGGGATTGAGTCCTG

GCTGTTATGATACCTATGGTGCAGACATAGACTGCCAGTGGATTGATATT

ACAGATGTAAAACCTGGAAACTATATCCTAAAGGTCAGTGTAAACCCCAG

CTACCTGGTTCCTGAATCTGACTATACCAACAATGTTGTGCGCTGTGACA

TTCGCTACACAGGACATCATGCGTATGCCTCAGGCTGCACAATTTCACCG

TATgggccc*GAACAAAAACTCATCTCAGAAGAGGATCTG*aatagcgccgt cgacCATCATCATCATCATCATTGA

The phLOXMCD expression vector was transfected into HEK293 cells as follows. 7×10$^5$ cells were plated into a well of a 6-well culture dish and grown at 37° C., 5% CO$_2$ in complete DMEM (Dulbecco's Modified Eagle's Medium+ 10% Fetal Bovine Serum+2 mM L-glutamine). After overnight growth the cells were transfected with phLOXMCD using Lipofectamine 2000 (Invitrogen, Carlsbad, Calif.) according to the manufacturer's instructions. Four hours later, the medium was aspirated and replaced with 2 ml complete DMEM, and the transfected cells were grown overnight. Stable cell lines were selected by limiting dilution in complete DMEM (cDMEM)+0.8 mg/ml Hygromycin B (hygro). Individual clones that survived selection were expanded and screened for expression of the hLOX catalytic domain, as follows. Expansion was achieved by growing cell clones in 6-well culture dishes to 75% confluence. At that point, medium was aspirated and fresh cDMEM+hygro was added. Five days later, the medium was harvested and analyzed directly for the presence of the LOX catalytic domain, as described below. Cells were removed from the surface of the culture dish by adding PBS+5 mM EDTA to the dish. The detached cell solution was subjected to centrifugation. Approximately 5×10$^5$ pelleted cells (out of a total of ~1×10$^6$) were lysed in 0.1 ml of M-PER mammalian protein extraction reagent (Pierce, Rockford, Ill.). After a 20 min incubation on ice, the cell lysate was subjected to centrifugation in a tabletop centrifuge at 15,000 rpm for 10 min. The soluble fraction (supernatant) was collected and analyzed for the presence of the LOX catalytic domain as described below. The insoluble fraction (pellet) was washed twice in M-PER, resuspended in M-PER and analyzed for the presence of the LOX catalytic domain as described below.

Example 6

Detection of Human LOX Catalytic Domain by Protein Immunoblotting

Samples of medium, soluble fraction, and insoluble fraction from six different clones were assayed by immunoblotting for the presence of the LOX catalytic domain expressed by the phLOXMCD expression vector. For analysis of medium, 150 ul of conditioned medium was mixed with 50 ul of NuPAGE® 4× LDS sample buffer (Invitrogen, Carlsbad, Calif.), and 20 ul of the resulting mixture was loaded onto a gel (see below). For the soluble and insoluble intracellular fractions, each sample corresponded to 1×10$^5$ cells. Samples of the intracellular fractions were mixed with NuPAGE® 4× LDS sample buffer (Invitrogen, Carlsbad, Calif.) and NuPAGE® 10× reducing agent to final concentrations of 1× of both of these reagents, boiled for 5 min, and subjected to electrophoresis on NuPAGE® Novex Bis-Tris gels (4-12% acrylamide). Running buffer was NuPAGE® MOPS buffer (Invitrogen, Carlsbad, Calif.). At the conclusion of electrophoresis, proteins were transferred out of the gel onto PVDF using an iBlot apparatus (Invitrogen, Carlsbad, Calif.).

For detection, the blots were blocked with 3% bovine serum albumin (BSA) in PBS+0.01% Tween for three hours at room temperature. Blots were then incubated for one hour at room temperature with a mouse anti-His$_5$ antibody (Qiagen, Valencia, Calif.) followed by a one hour incubation at room temperature with a horseradish peroxidase (HRP)-conjugated donkey anti-mouse antibody (Jackson ImmunoResearch, West Grove, Pa.) and developed with Chemi-Glow® (Alpha Innotech, San Leandro, Calif.).

Figure 1:
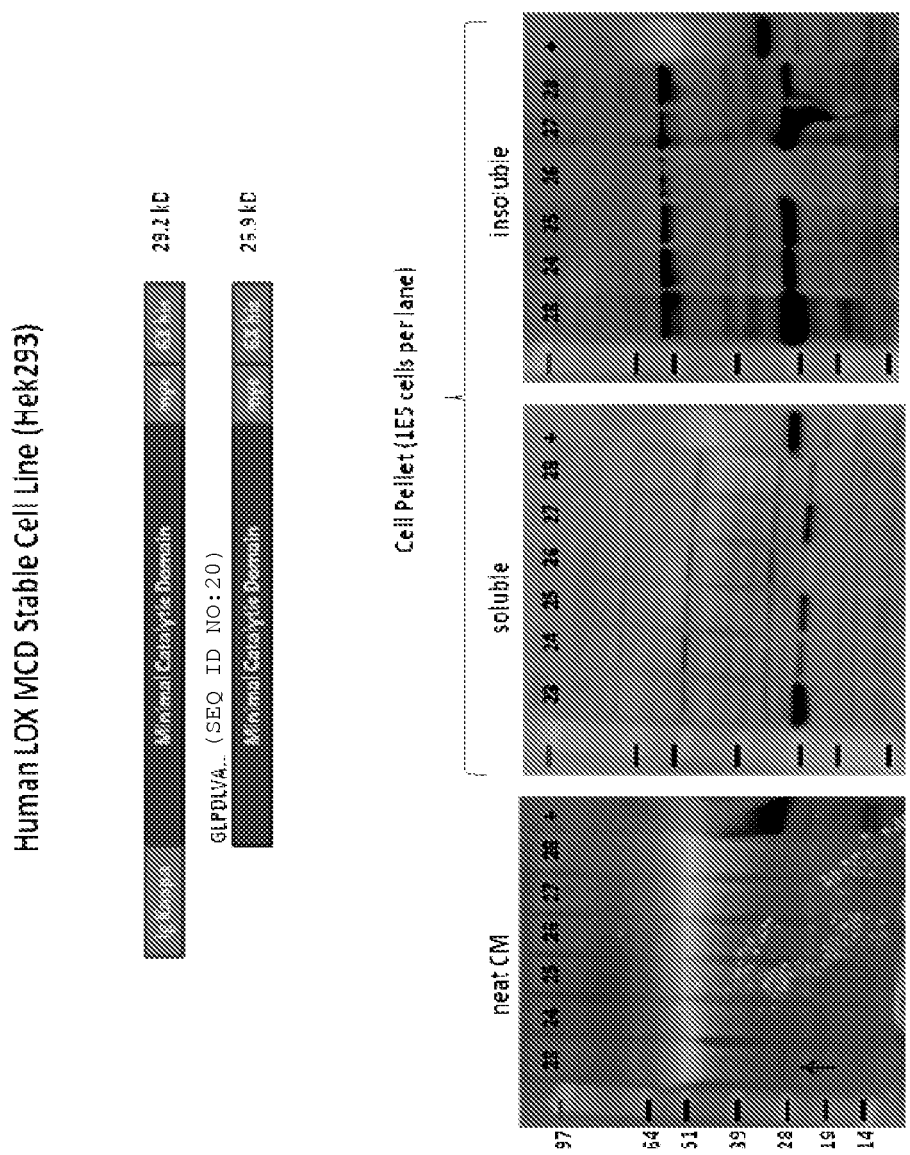
FIG. 1 shows expression of the catalytic domain of the human lysyl oxidase (hLOX) protein by HEK293 cells transfected with the phLOXMCD expression vector. Analysis of six stably transfected cell lines (numbered 23 through 28) by immunoblotting is shown. The left panel shows an immunoblot of a polyacrylamide gel containing samples (15 ul) of undiluted growth medium (neat CM) from each of the six cell lines. The middle panel shows analysis of soluble intracellular material, and the right panel shown analysis of insoluble intracellular material. For each of these panels, each lane contains material from approximately $10^5$ cells. All blots were probed with a primary mouse anti-$His_5$ antibody, then reacted with a secondary HRP conjugated donkey-anti-mouse antibody. HRP activity was revealed using the Chemi-Glow® reagent (Alpha Innotech, San Leandro, Calif.). The processed catalytic domain has a predicted molecular weight of 26.9 kD.

The results are shown in FIG. 1, for six clones (labeled 23 through 28). The left most panel, showing assays of growth medium, indicates little to no secretion of the catalytic domain, except for a small amount of secreted product in clone 23 (arrow). The secreted protein exhibits an apparent molecular weight of 29 kD, characteristic of unprocessed polypeptide. This could be due to lack of cleavage (or incomplete cleavage) of the signal peptide or to post-translational modification of the secreted polypeptide.

Trichloroacetic acid precipitation of growth medium from HEK293 cells that had been transiently transfected with the phLOXMCD expression vector revealed the presence of insoluble LOX catalytic domain in the growth medium.

Intracellular expression of the catalytic domain was detected in five out of the six clones, in both the soluble and insoluble fractions (FIG. 1, center and right panels). In addition, high-molecular weight aggregates were detected in the insoluble intracellular fraction.

Inasmuch as solubility can be an indication of a correctly folded and processed polypeptide, the presence of soluble intracellular polypeptide product indicates the likelihood that properly folded, enzymatically active catalytic domain is being produced in the transfected cells.

In addition to HEK293 cells, expression of the LOX catalytic domain was observed in additional cell types. Transient expression of the phLOXMCD expression vector in CHOk1 cells resulted in intracellular expression of the catalytic domain (detected in a whole-cell lysate), but no secretion of the catalytic domain was detected. Transient transfection of SW620 cells also resulted in intracellular expression without detectable secretion.

Example 7

Expression of Human LOXL2 Catalytic Domain in Mammalian Cells

An expression cassette (Genecopoeia, Germantown, Md.) that is used for the expression of a polypeptide including the human LOXL2 catalytic domain was constructed by PCR amplification, using a human LOXL2 cDNA as template. The amplification product, containing sequences encoding the catalytic domain, was cloned into the pSecTag2/Hygro B vector (Invitrogen, Carlsbad, Calif.), generating the pSecTag2hygro-hLOXL2 MCD (also referred to as phLOXL2MCD) expression vector. Transcription of this clone with T7 RNA polymerase generates a mRNA encoding a polypeptide containing (in N-terminal to C-terminal order) an Immunoglobulin kappa signal sequence, the human LOXL2 catalytic domain, a myc epitope tag and a His$_6$ purification tag. This polypeptide has the following amino acid sequence:

(SEQ ID NO: 11)
METDTLLLWVLLLWVPGSTGD*AAQPARRARRTKL*TAPDLVLNAEMVQQTT

YLEDRPMFMLQCAMEENCLSASAAQTDPTTGYRRLLRFSSQIHNNGQSDF

RPKNGRHAWIWHDCHRHYHSMEVFTHYDLLNLNGTKVAEGHKASFCLEDT

ECEGDIQKNYECANFGDQGITMGCWDMYRHDIDCQWVDITDVPPGDYLFQ

VVINPNFEVAESDYSNNIMKCRSRYDGHRIWMYNCHIGGSFSEETEKKFE

HFSGLLNNQLSPQ*SRGGP*EQKLISEEDL*NSAVD*HHHHHH.

The sequences of the signal peptide and myc tag are underlined. The italicized sequences represent amino acid sequences encoded in whole or part by vector sequences and restriction sites used in the cloning (AAQPARRARRTKL and SRGGP) and a linker sequence (NSAVD).

The DNA sequence encoding this polypeptide (with underlined sequences denoting those encoding the leader and the myc tag, and linker sequences indicated in lower-case type) is:

(SEQ ID NO: 12)
ATGGAGACAGACACACTCCTGCTATGGGTACTGCTGCTCTGGGTTCCAGG

TTCCACTGGTGACgcggcccagccggccaggcgcgcgcgccgtacgaagc ttACCGCCCCTGACCTGGTCCTCAATGCGGAGATGGTGCAGCAGACCACC

TACCTGGAGGACCGGCCCATGTTCATGCTGCAGTGTGCCATGGAGGAGAA

CTGCCTCTCGGCCTCAGCCGCGCAGACCGACCCCACCACGGGCTACCGCC

GGCTCCTGCGCTTCTCCTCCCAGATCCACAACAATGGCCAGTCCGACTTC

CGGCCCAAGAACGGCCGCCACGCGTGGATCTGGCACGACTGTCACAGGCA

CTACCACAGCATGGAGGTGTTCACCCACTATGACCTGCTGAACCTCAATG

GCACCAAGGTGGCAGAGGGCCACAAGGCCAGCTTCTGCTTGGAGGACACA

GAATGTGAAGGAGACATCCAGAAGAATTACGAGTGTGCCAACTTCGGCGA

TCAGGGCATCACCATGGGCTGCTGGGACATGTACCGCCATGACATCGACT

GCCAGTGGGTTGACATCACTGACGTGCCCCCTGGAGACTACCTGTTCCAG

GTTGTTATTAACCCCAACTTCGAGGTTGCAGAATCCGATTACTCCAACAA

CATCATGAAATGCAGGAGCCGCTATGACGGCCACCGCATCTGGATGTACA

ACTGCCACATAGGTGGTTCCTTCAGCGAAGAGACGGAAAAAAAGTTTGAG

CACTTCAGCGGGCTCTTAAACAACCAGCTGTCCCCGCAGtctcgaggagg gcccGAACAAAAACTCATCTCAGAAGAGGATCTGaatagcgccgtcgacC

ATCATCATCATCATCATTGA

HEK293 cells were transfected with the phLOXL2MCD expression vector, stable cell lines were selected by limiting dilution, and clones were expanded using the same methods as described in Example 5 for the phLOXMCD vector. Medium was collected for analysis, and cells were detached and pelleted as described in Example 5.

Example 8

Detection of Human LOXL2 Catalytic Domain by Protein Immunoblotting

Samples of pelleted cells containing approximately 5×10$^5$ cells, obtained as described in Example 7, were analyzed by immunoblotting. Cell suspension containing approximately 5×10$^5$ cells was subjected to centrifugation at 6,000 rpm for 10 min and the supernatant was aspirated. The pellet was resuspended in 100 ul of M-PER lysis buffer, followed by incubation on ice for 20 min. Insoluble cell debris was removed by centrifugation at 15,000 rpm for 20 min, and 75 ul of the supernatant (cleared cell lysate) was removed and mixed with 30 ul of NuPAGE® 4× LDS sample buffer (Invitrogen, Carlsbad, Calif.) and 10 ul of NuPAGE® 10× reducing agent. The mixture was boiled for 5 min, then placed on ice until application to the gel. Typically, 20 ul of each sample (corresponding to ~1×10$^5$ cells) was subjected to electrophoresis on NuPAGE® Novex Bis-Tris gels (4-12% acrylamide). Running buffer was NuPAGE® MOPS buffer (Invitrogen, Carlsbad, Calif.). At the conclusion of electrophoresis, proteins were transferred out of the gel onto PVDF using an iBlot apparatus (Invitrogen, Carlsbad, Calif.).

For detection, the blots were processed as described in Example 6 for the phLOXMCD expression products.

The results, shown in the left panel of FIG. 2, indicate intracellular expression of the LOXL2 catalytic domain in nine different clones. Both monomeric and aggregated forms of the protein were detected, with monomeric forms predominating.

To determine whether the human LOXL2 catalytic domain was secreted, cell clones, obtained as described in Example 7 for the phLOXMCD-transfected cells, were grown in cDMEM+hygro for 90 hours, at which point 15 ul of medium was removed and mixed with 5 ul of 4× LDS sample buffer+ reducing agent (NuPAGE®, Invitrogen, Carlsbad, Calif.), boiled for 5 min, subjected to polyacrylamide gel electrophoresis and analyzed as described above for whole cell lysates. The results, shown in the right panel of FIG. 2 show that, in contrast to the human LOX catalytic domain, the human LOXL2 catalytic domain is secreted by HEK293 cells in quantities that are detectable in unconcentrated growth medium.

Example 9

Expression of Murine LOX Catalytic Domain in Mammalian Cells

An expression cassette that is used for the expression of a polypeptide including the murine LOX catalytic domain was constructed by PCR amplification, using a mouse LOX cDNA as template (GenBank BC018439, obtained from Invitrogen, Carlsbad, Calif.). The amplification product, containing sequences encoding the catalytic domain, was cloned into the pSecTag2/Hygro B vector (Invitrogen, Carlsbad, Calif.), generating the pSecTag2hygro-mLOX MCD (also referred to as pmLOXMCD) expression vector. Transcription of this clone with T7 RNA polymerase generates a mRNA encoding a polypeptide containing (in N-terminal to C-terminal order) an Immunoglobulin kappa signal sequence, the murine LOX catalytic domain, a myc epitope tag and a His$_6$ purification tag. This polypeptide has the following amino acid sequence:

(SEQ ID NO: 13)
METDTLLLWVLLLWVPGSTGD*AAQP*AGLPDLVPDPYYIQASTYVQKMSMY

NLRCAAEENCLASSAYRADVRDYDHRVLLRFPQRVKNQGTSDFLPSRPRY

SWEWHSCHQHYHSMDEFSHYDLLDANTQRRVAEGHKASFCLEDTSCDYGY

HRRFACTAHTQGLSPGCYDTYAADIDCQWIDITDVQPGNYILKVSVNPSY

LVPESDYTNNVVRCDIRYTGHHAYASGCTISPY*GP*EQKLISEEDL*NSAVD*

HHHHHH

The sequences of the signal peptide and myc tag are underlined. The italicized sequences represent amino acid sequences encoded in whole or part by vector sequences or restriction sites used in the cloning (AAQP and GP) and a linker sequence (NSAVD).

The DNA sequence encoding this polypeptide (with underlined sequences denoting those encoding the leader and the myc tag, and linker sequences indicated in lower-case type) is:

(SEQ ID NO: 14)
ATGGAGACAGACACACTCCTGCTATGGGTACTGCTGCTCTGGGTTCCAGG

TTCCACTGGTGACgcggcccagccggccGGTCTCCCGGACCTGGTGCCCG

ACCCCTACTACATCCAGGCTTCCACGTACGTCCAGAAGATGTCTATGTAC

AACCTGAGATGCGCTGCGGAAGAAAACTGCCTGGCCAGTTCAGCATATAG

GGCGGATGTCAGAGACTATGACCACAGGGTACTGCTACGATTTCCGCAAA

GAGTGAAGAACCAAGGGACATCGGACTTCTTACCAAGCCGCCCTCGGTAC

TCCTGGGAGTGGCACAGCTGTCACCAACATTACCACAGCATGGACGAATT

CAGCCACTATGACCTGCTTGATGCCAACACACAGAGGAGAGTGGCTGAAG

GCCACAAAGCAAGCTTCTGTCTGGAGGACACGTCCTGTGACTATGGGTAC

CACAGGCGCTTTGCGTGCACTGCACACACACAGGGATTGAGTCCTGGATG

TTATGACACCTATGCGGCAGACATAGACTGCCAGTGGATTGATATTACAG

ATGTACAACCTGGAAACTACATTCTAAAGGTCAGTGTAAACCCCAGCTAC

CTGGTGCCTGAATCAGACTACACTAACAATGTTGTACGCTGTGACATTCG

CTACACAGGACATCATGCCTATGCCTCAGGCTGCACAATTTCACCGTATg ggcccGAACAAAAACTCATCTCAGAAGAGGATCTGaatagcgccgtcgac

CATCATCATCATCATTGA

HEK293 cells were transfected with the pmLOXMCD expression vector, stable cell lines were selected by limiting dilution, and clones were expanded using the same methods as described in Example 5 for the phLOXMCD vector. Medium was collected for analysis, and cells were detached, pelleted and fractionated into soluble and insoluble fractions, as described in Example 5.

Expression of the murine LOX catalytic domain was assayed by immunoblotting, using the same methods described in Example 6 for the analysis of the human catalytic domain. The results, shown in FIG. 3, indicate that the murine LOX catalytic domain is secreted in detectable quantities (left panel), in contrast to the human LOX catalytic domain. The intracellular expression profile of the mLOX catalytic domain is similar to that of the hLOX catalytic domain, with monomeric protein present in both the soluble and insoluble fractions, and aggregates present in the insoluble fraction.

Example 10

Secretion of Human LOX Catalytic Domain from Mammalian Cells

FIG. 4 contains a schematic diagram showing the differences in the amino acid sequences of the human (top) and murine (bottom) LOX catalytic domains. As can be seen, the two sequences differ at only four positions. As shown above, and as confirmed in the left panel of FIG. 4, using ten-fold concentrated conditioned growth medium (10× CM), the murine LOX catalytic domain (M) was secreted from cells transfected with a vector encoding it; while the human LOX catalytic domain (H) was not secreted. Therefore, if secretion of a human LOX catalytic domain is desired, one can alter any of residues 7, 38, 146, or 160 (numbers refer to the position in the amino acid sequence of the catalytic domain expressed in the phLOXMCD and pmLOXMCD expression vectors disclosed herein), or any combination of these residues, or all four of these residues, from the human sequence to the murine sequence. For example, any, or all, or any combination, of the following amino acid sequence changes can be made: A7P, T38S, G146A, K160Q.

Conversely, if one desires to reduce secretion of a murine LOX catalytic domain, thereby retaining more of this polypeptide intracellularly, changes at residues 7, 38, 146 and 160, from the murine sequence to the human sequence, can be made. Thus, for example, any, or all, or any combination of the following amino acid sequence changes can be made: P7A, S38T, A146G, Q160K.

Example 11

Expression of Murine LOXL2 Catalytic Domain in Mammalian Cells

An expression cassette that is used for the expression of a polypeptide including the murine LOXL2 catalytic domain is constructed by PCR amplification, using a mouse LOXL2 cDNA as template (commercially synthesized based on Gen-Bank NM033325). The amplification product, containing sequences encoding the catalytic domain, is cloned into the pSecTag2/Hygro B vector (Invitrogen, Carlsbad, Calif.), generating the pSecTag2hygro-mLOXL2 MCD (also referred to as pmLOXL2MCD) expression vector. Transcription of this clone with T7 RNA polymerase generates a mRNA encoding a polypeptide containing (in N-terminal to C-terminal order) an Immunoglobulin kappa signal sequence, the murine LOXL2 catalytic domain, a myc epitope tag and a His$_6$ purification tag. This polypeptide has the following amino acid sequence (with the leader sequence and the myc tag underlined):

```
                                        (SEQ ID NO: 15)
METDTLLLWVLLLWVPGSTGDAAQPATAPDLVLNAEIVQQTAYLEDRPMS

LLQCAMEENCLSASAVHTDPTRGHRRLLRFSSQIHNNGQSDFRPKNGRHA

WIWHDCHRHYHSMEVFTYYDLLSLNGTKVAEGHKASFCLEDTECEGDIQK

SYECANFGEQGITMGCWDMYRHDIDCQWIDITDVPPGDYLFQVVINPNYE

VPESDFSNNIMKCRSRYDGYRIWMYNCHVGGAFSEETEQKFEHFSGLLNN

QLSVQGPEQKLISEEDLNSAVDHHHHHH
```

The sequences of the signal peptide and myc tag are underlined. The italicized sequences represent amino acid sequences encoded in whole or part by vector sequences and restriction sites used in the cloning (AAQP and GP) and a linker sequence (NSAVD).

The DNA sequence encoding this polypeptide (with underlined sequences denoting those encoding the leader and the myc tag, and linker sequences indicated in lower-case type) is:

```
                                        (SEQ ID NO: 16)
ATGGAGACAGACACACTCCTGCTATGGGTACTGCTGCTCTGGGTTCCAGG

TTCCACTGGTGACgcggcccagccggccACTGCACCTGACCTGGTGCTTA

ATGCTGAGATTGTCCAGCAGACTGCCTACCTGGAGGACAGGCCCATGTCC

TTGCTGCAGTGTGCCATGGAGGAGAACTGCCTCTCCGCCTCCGCTGTGCA

CACCGACCCCACCAGAGGCCACCGGCGCCTTTTACGCTTCTCCTCCCAGA

TCCACAACAATGGCCAGTCTGACTTCCGCCCCAAGAATGCCCGCCATGCG
```

TGGATTTGGCACGACTGCCACAGGCACTACCACAGCATGGAAGTCTTCAC

TTACTATGACCTGCTGAGCCTCAACGGCACCAAGGTGGCTGAGGGCCACA

AGGCCAGCTTCTGCCTGGAGGACACTGAGTGTGAGGGAGACATTCAGAAG

AGTTACGAGTGTGCCAACTTTGGAGAACAAGGCATCACCATGGGCTGCTG

GGACATGTACCGTCATGACATTGACTGCCAGTGGATAGACATCACCGATG

TGCCCCCTGGAGACTACCTGTTCCAGGTTGTCATTAACCCCAACTATGAA

GTGCCAGAATCAGATTTCTCTAACAACATCATGAAGTGCAGGAGCCGCTA

TGATGGCTACCGCATCTGGATGTACAACTGTCACGTAGGTGGAGCCTTCA

GTGAGGAGACAGAACAGAAGTTCGAACACTTCAGTGGACTTCTAAATAAC

CAGCTCTCTGTACAGgggcccGAACAAAAACTCATCTCAGAAGAGGATCT

Gaatagcgccgtcgac CATCATCATCATCATCATTGA

HEK293 cells are transfected with the pmLOXL2MCD expression vector, stable cell lines are selected by limiting dilution, and clones are expanded using the same methods as described in Example 5 for the phLOXMCD vector. Medium is collected for analysis, and cells are detached, pelleted and fractionated into soluble and insoluble fractions, as described in Example 5.

Expression of the murine LOXL2-derived polypeptide is assayed by immunoblotting, using the same methods described in Example 6 for the analysis of the human catalytic domain.

Example 12

Generation of Enzymatically Active Human LOXL2 Catalytic Domain from Transiently Transfected Cells 293F cells (a subclone of the HEK293 cell line adapted for growth in suspension culture, Invitrogen, Carlsbad, Calif.) were grown in spinner flasks, according to the manufacturer's protocol. Once the culture had reached a density of 0.8-1.2× $10^6$ cells/ml, the cell culture was transferred to a CB22 Bag (WAVE, GE Health, Piscataway, N.J.). Eight liters of cell culture was transfected with 8 mg of the phLOXL2 vector, using the 293fectin reagent (Invitrogen, Carlsbad, Calif.). Transfected cells were grown in the CB22 bag for three days, after which the cell culture was subjected to centrifugation in an Allegra 6R benchtop centrifuge (Beckman Coulter) in a swinging bucket rotor at 3,000 rpm for 10 min. The supernatant was collected and filtered through a 0.22 mm PES membrane.

The LOXL2-derived polypeptide was purified from the cell culture supernatant on a Ni-Sepharose resin (GE Healthcare, Piscataway, N.J.). The resin was equilibrated with 0.1 M Tris-Cl, pH 8.0. Conditioned medium (i.e., the cell culture supernatant) was loaded onto the equilibrated resin; then the column was washed with 10 column volumes of 0.1 M Tris-Cl, pH 8.0, 0.25 M NaCl, 0.02 M imidazole. His-tagged catalytic domain was eluted with five column volumes of 0.1 M Tris-Cl, pH 8.0, 0.15 M NaCl, 0.3 M imidazole. The eluate was concentrated on an Amicon Ultra 15 10 kD MWCL (Millipore, Billerica, Mass.) and the concentrated material was dialyzed against 0.05 M borate, pH 8.0 overnight at 4° C. Samples were analyzed on SDS polyacrylamide gels (4-12% gradient Bis-Tris gels, Invitrogen, Carlsbad, Calif.) under reducing conditions.

Example 13

Enzymatic Activity of the Catalytic Domain of Human LOXL2

A polypeptide containing the catalytic domain of human LOXL2 was produced as described in Example 12 above. Enzymatic activity was assessed using a biochemical assay that couples the production of peroxide (liberated by LOXL2 after deamination of 1,5-diaminopentane) to the HRP-catalyzed conversion of Amplex® red to a fluorescent product (resorufin). Palamakumbura et al. (2002) *Anal. Biochem.* 300: 245-251. Reaction plates were obtained from Corning. Amplex® Red reagent was from Invitrogen (Carlsbad, Calif.). Horseradish peroxidase (HRP), 1,5-diaminopentane, and antifoam were from Sigma (St. Louis, Mo.). All other reagents were of the highest quality available.

Enzyme mixture was assembled by adding 10 uL of pooled peak fractions (see Example 12) to 40 uL assay solution (62.5 mM sodium borate pH 8.0, 5 units/mL HRP, 10 ppm antifoam). Substrate solution contained 50 mM sodium borate, 100 uM Amplex® red reagent, 20 mM 1,5-diaminopentane, 10 ppm antifoam. The reaction was started by mixing 50 ul of enzyme mixture with 50 ul of substrate solution. One reaction also contained 2 mM of βAPN (beta-aminoproprionitrile, an inhibitor of the catalytic activity of lysyl oxidase and LOXL2). Reaction mixtures were incubated, at 37° C., in a Molecular Devices M5 plate reader configured to measure fluorescence (ex=544 nm, em=590 nm) in kinetics mode for 1 hour. Data were recorded as the slope of the fluorescence response to time.

FIG. 5 shows the results of this assay, in the form of a time course of resorufin production, expressed in relative fluorescent units (RFU). The human LOXL2-derived polypeptide exhibited measurable enzymatic activity, and the activity was inhibited by βAPN. Accordingly, the polypeptide comprises an enzymatically active catalytic domain of LOXL2.

That which is claimed is:

1. An isolated polypeptide, comprising:
a catalytic domain of a human LOXL2 protein, wherein:
the catalytic domain comprises the amino acid sequence selected from the group consisting of: SEQ ID NO: 3, and SEQ ID NO: 3 without the initial TA residues; and
the polypeptide does not contain sequences from the human LOXL2 protein outside its catalytic domain.

2. The polypeptide of claim 1, wherein the catalytic domain is of a human LOXL2 and comprises the amino acid sequence set forth in SEQ ID NO:3.

3. The polypeptide of claim 1, further comprising a signal sequence, an epitope tag and a purification tag.

4. The polypeptide of claim 3, wherein the signal sequence is an immunoglobulin kappa signal sequence.

5. The polypeptide of claim 3, wherein the epitope tag is myc tag.

6. The polypeptide of claim 3, wherein the purification tag is a $His_6$ tag.

7. The polypeptide of claim 2, further comprising a signal sequence, an epitope tag and a purification tag.

8. The polypeptide of claim 7, wherein the signal sequence is an immunoglobulin kappa signal sequence.

9. The polypeptide of claim 7, wherein the epitope tag is myc tag.

10. The polypeptide of claim 7, wherein the purification tag is a $His_6$ tag.

11. The polypeptide of claim 7, wherein the polypeptide has an amino acid sequence as set forth in SEQ ID NO:11.

* * * * *

SEQUENCE LISTING

<160> NUMBER OF SEQ ID NOS: 22

<210> SEQ ID NO 1
<211> LENGTH: 207
<212> TYPE: PRT
<213> ORGANISM: Homo Sapiens

<400> SEQUENCE: 1

```
Gly Leu Pro Asp Leu Val Ala Asp Pro Tyr Tyr Ile Gln Ala Ser Thr
 1               5                  10                  15

Tyr Val Gln Lys Met Ser Met Tyr Asn Leu Arg Cys Ala Ala Glu Glu
            20                  25                  30

Asn Cys Leu Ala Ser Thr Ala Tyr Arg Ala Asp Val Arg Asp Tyr Asp
        35                  40                  45

His Arg Val Leu Leu Arg Phe Pro Gln Arg Val Lys Asn Gln Gly Thr
    50                  55                  60

Ser Asp Phe Leu Pro Ser Arg Pro Arg Tyr Ser Trp Glu Trp His Ser
65                  70                  75                  80

Cys His Gln His Tyr His Ser Met Asp Glu Phe Ser His Tyr Asp Leu
                85                  90                  95

Leu Asp Ala Asn Thr Gln Arg Arg Val Ala Glu Gly His Lys Ala Ser
            100                 105                 110

Phe Cys Leu Glu Asp Thr Ser Cys Asp Tyr Gly Tyr His Arg Arg Phe
        115                 120                 125

Ala Cys Thr Ala His Thr Gln Gly Leu Ser Pro Gly Cys Tyr Asp Thr
    130                 135                 140

Tyr Gly Ala Asp Ile Asp Cys Gln Trp Ile Asp Ile Thr Asp Val Lys
145                 150                 155                 160

Pro Gly Asn Tyr Ile Leu Lys Val Ser Val Asn Pro Ser Tyr Leu Val
                165                 170                 175

Pro Glu Ser Asp Tyr Thr Asn Asn Val Val Arg Cys Asp Ile Arg Tyr
            180                 185                 190

Thr Gly His His Ala Tyr Ala Ser Gly Cys Thr Ile Ser Pro Tyr
        195                 200                 205
```

<210> SEQ ID NO 2
<211> LENGTH: 624
<212> TYPE: DNA
<213> ORGANISM: Homo Sapiens

<400> SEQUENCE: 2

```
ggtctcccag acctggtggc cgacccctac tacatccagg cgtccacgta cgtgcagaag    60
atgtccatgt acaacctgag atgcgcggcg gaggaaaact gtctggccag tacagcatac   120
agggcagatg tcagagatta tgatcacagg gtgctgctca gatttcccca agagtgaaa    180
aaccaaggga catcagattt cttacccagc cgaccaagat attcctggga atggcacagt   240
tgtcatcaac attaccacag tatggatgag tttagccact atgacctgct tgatgccaac   300
acccagagga gagtggctga aggccacaaa gcaagtttct gtcttgaaga cacatcctgt   360
gactatggct accacaggcg atttgcatgt actgcacaca cacagggatt gagtcctggc   420
tgttatgata cctatggtgc agacatagac tgccagtgga ttgatattac agatgtaaaa   480
cctggaaaact atatcctaaa ggtcagtgta aaccccagct acctggttcc tgaatctgac   540
tataccaaca atgttgtgcg ctgtgacatt cgctacacag acatcatgc gtatgcctca   600
ggctgcacaa tttcaccgta ttag                                          624
```

<210> SEQ ID NO 3
<211> LENGTH: 229
<212> TYPE: PRT
<213> ORGANISM: Homo Sapiens

<400> SEQUENCE: 3

```
Thr Ala Pro Asp Leu Val Leu Asn Ala Glu Met Val Gln Gln Thr Thr
 1               5                  10                  15

Tyr Leu Glu Asp Arg Pro Met Phe Met Leu Gln Cys Ala Met Glu Glu
            20                  25                  30

Asn Cys Leu Ser Ala Ser Ala Ala Gln Thr Asp Pro Thr Thr Gly Tyr
        35                  40                  45

Arg Arg Leu Leu Arg Phe Ser Ser Gln Ile His Asn Asn Gly Gln Ser
    50                  55                  60

Asp Phe Arg Pro Lys Asn Gly Arg His Ala Trp Ile Trp His Asp Cys
65                  70                  75                  80

His Arg His Tyr His Ser Met Glu Val Phe Thr His Tyr Asp Leu Leu
                85                  90                  95

Asn Leu Asn Gly Thr Lys Val Ala Glu Gly His Lys Ala Ser Phe Cys
           100                 105                 110

Leu Glu Asp Thr Glu Cys Glu Gly Asp Ile Gln Lys Asn Tyr Glu Cys
       115                 120                 125

Ala Asn Phe Gly Asp Gln Gly Ile Thr Met Gly Cys Trp Asp Met Tyr
   130                 135                 140

Arg His Asp Ile Asp Cys Gln Trp Val Asp Ile Thr Asp Val Pro Pro
145                 150                 155                 160

Gly Asp Tyr Leu Phe Gln Val Val Ile Asn Pro Asn Phe Glu Val Ala
                165                 170                 175

Glu Ser Asp Tyr Ser Asn Asn Ile Met Lys Cys Arg Ser Arg Tyr Asp
            180                 185                 190

Gly His Arg Ile Trp Met Tyr Asn Cys His Ile Gly Gly Ser Phe Ser
        195                 200                 205

Glu Glu Thr Glu Lys Lys Phe Glu His Phe Ser Gly Leu Leu Asn Asn
    210                 215                 220

Gln Leu Ser Pro Gln
225
```

<210> SEQ ID NO 4

<211> LENGTH: 690
<212> TYPE: DNA
<213> ORGANISM: Homo Sapiens

<400> SEQUENCE: 4

```
accgcccctg acctggtcct caatgcggag atggtgcagc agaccaccta cctggaggac    60
cggcccatgt tcatgctgca gtgtgccatg aggagaact gcctctcggc ctcagccgcg    120
cagaccgacc ccaccacggg ctaccgccgg ctcctgcgct tctcctccca gatccacaac    180
aatgccagt ccgacttccg gcccaagaac ggccgccacg cgtggatctg cacgactgt    240
cacaggcact accacagcat ggaggtgttc acccactatg acctgctgaa cctcaatggc    300
accaaggtgg cagagggcca aaggccagc ttctgcttgg aggacacaga atgtgaagga    360
gacatccaga agaattacga gtgtgccaac ttcggcgatc agggcatcac catgggctgc    420
tgggacatgt accgccatga catcgactgc cagtgggttg acatcactga cgtgccccct    480
ggagactacc tgttccaggt tgttattaac cccaacttcg aggttgcaga atccgattac    540
tccaacaaca tcatgaaatg caggagccgc tatgacggcc accgcatctg gatgtacaac    600
tgccacatag gtggttcctt cagcgaagag acggaaaaaa agtttgagca cttcagcggg    660
ctcttaaaca accagctgtc cccgcagtaa                                     690
```

<210> SEQ ID NO 5
<211> LENGTH: 207
<212> TYPE: PRT
<213> ORGANISM: Mus musculus

<400> SEQUENCE: 5

```
Gly Leu Pro Asp Leu Val Pro Asp Pro Tyr Tyr Ile Gln Ala Ser Thr
 1               5                   10                  15

Tyr Val Gln Lys Met Ser Met Tyr Asn Leu Arg Cys Ala Ala Glu Glu
            20                  25                  30

Asn Cys Leu Ala Ser Ser Ala Tyr Arg Ala Asp Val Arg Asp Tyr Asp
        35                  40                  45

His Arg Val Leu Leu Arg Phe Pro Gln Arg Val Lys Asn Gln Gly Thr
    50                  55                  60

Ser Asp Phe Leu Pro Ser Arg Pro Arg Tyr Ser Trp Glu Trp His Ser
65                  70                  75                  80

Cys His Gln His Tyr His Ser Met Asp Glu Phe Ser His Tyr Asp Leu
                85                  90                  95

Leu Asp Ala Asn Thr Gln Arg Arg Val Ala Glu Gly His Lys Ala Ser
            100                 105                 110

Phe Cys Leu Glu Asp Thr Ser Cys Asp Tyr Gly Tyr His Arg Arg Phe
        115                 120                 125

Ala Cys Thr Ala His Thr Gln Gly Leu Ser Pro Gly Cys Tyr Asp Thr
    130                 135                 140

Tyr Ala Ala Asp Ile Asp Cys Gln Trp Ile Asp Ile Thr Asp Val Gln
145                 150                 155                 160

Pro Gly Asn Tyr Ile Leu Lys Val Ser Val Asn Pro Ser Tyr Leu Val
                165                 170                 175

Pro Glu Ser Asp Tyr Thr Asn Asn Val Val Arg Cys Asp Ile Arg Tyr
            180                 185                 190

Thr Gly His His Ala Tyr Ala Ser Gly Cys Thr Ile Ser Pro Tyr
        195                 200                 205
```

<210> SEQ ID NO 6
<211> LENGTH: 624

```
<212> TYPE: DNA
<213> ORGANISM: Mus musculus

<400> SEQUENCE: 6
ggtctcccgg acctggtgcc cgacccctac tacatccagg cttccacgta cgtccagaag      60
atgtctatgt acaacctgag atgcgctgcg gaagaaaact gcctggccag ttcagcatat     120
agggcggatg tcagagacta tgaccacagg gtactgctac gatttccgca aagagtgaag     180
aaccaaggga catcggactt cttaccaagc cgccctcggt actcctggga gtggcacagc     240
tgtcaccaac attaccacag catggacgaa ttcagccact atgacctgct tgatgccaac     300
acacagagga gagtggctga aggccacaaa gcaagcttct gtctggagga cacgtcctgt     360
gactatgggt accacaggcg ctttgcgtgc actgcacaca cacagggatt gagtcctgga     420
tgttatgaca cctatgcggc agacatagac tgccagtgga ttgatattac agatgtacaa     480
cctggaaact acattctaaa ggtcagtgta aaccccagct acctggtgcc tgaatcagac     540
tacactaaca atgttgtacg ctgtgacatt cgctacacag acatcatgc ctatgcctca      600 ggctgcacaa tttcaccgta ttag                                            624

<210> SEQ ID NO 7
<211> LENGTH: 229
<212> TYPE: PRT
<213> ORGANISM: Mus musculus

<400> SEQUENCE: 7

Thr Ala Pro Asp Leu Val Leu Asn Ala Glu Ile Val Gln Gln Thr Ala
 1               5                  10                  15

Tyr Leu Glu Asp Arg Pro Met Ser Leu Leu Gln Cys Ala Met Glu Glu
             20                  25                  30

Asn Cys Leu Ser Ala Ser Ala Val His Thr Asp Pro Thr Arg Gly His
         35                  40                  45

Arg Arg Leu Leu Arg Phe Ser Gln Ile His Asn Asn Gly Gln Ser
     50                  55                  60

Asp Phe Arg Pro Lys Asn Gly Arg His Ala Trp Ile Trp His Asp Cys
 65                  70                  75                  80

His Arg His Tyr His Ser Met Glu Val Phe Thr Tyr Tyr Asp Leu Leu
                 85                  90                  95

Ser Leu Asn Gly Thr Lys Val Ala Glu Gly His Lys Ala Ser Phe Cys
            100                 105                 110

Leu Glu Asp Thr Glu Cys Glu Gly Asp Ile Gln Lys Ser Tyr Glu Cys
        115                 120                 125

Ala Asn Phe Gly Glu Gln Gly Ile Thr Met Gly Cys Trp Asp Met Tyr
    130                 135                 140

Arg His Asp Ile Asp Cys Gln Trp Ile Asp Ile Thr Asp Val Pro Pro
145                 150                 155                 160

Gly Asp Tyr Leu Phe Gln Val Val Ile Asn Pro Asn Tyr Glu Val Pro
                165                 170                 175

Glu Ser Asp Phe Ser Asn Asn Ile Met Lys Cys Arg Ser Arg Tyr Asp
            180                 185                 190

Gly Tyr Arg Ile Trp Met Tyr Asn Cys His Val Gly Gly Ala Phe Ser
        195                 200                 205

Glu Glu Thr Glu Gln Lys Phe Glu His Phe Ser Gly Leu Leu Asn Asn
    210                 215                 220

Gln Leu Ser Val Gln
225
```

<210> SEQ ID NO 8
<211> LENGTH: 690
<212> TYPE: DNA
<213> ORGANISM: Mus musculus

<400> SEQUENCE: 8

```
actgcacctg acctggtgct taatgctgag attgtccagc agactgccta cctggaggac      60
aggcccatgt ccttgctgca gtgtgccatg gaggagaact gcctctccgc ctccgctgtg     120
cacaccgacc ccaccagagg ccaccggcgc cttttacgct tctcctccca gatccacaac     180
aatggccagt ctgacttccg ccccaagaat ggccgccatg cgtggatttg cacgactgc      240
cacaggcact accacagcat ggaagtcttc acttactatg acctgctgag cctcaacggc     300
accaaggtgg ctgagggcca caaggccagc ttctgcctgg aggacactga gtgtgaggga     360
gacattcaga gagttacga gtgtgccaac tttggagaac aaggcatcac catgggctgc     420
tgggacatgt accgtcatga cattgactgc cagtggatag acatcaccga tgtgcccct     480
ggagactacc tgttccaggt tgtcattaac cccaactatg aagtgccaga atcagatttc     540
tctaacaaca tcatgaagtg caggagccgc tatgatggct accgcatctg gatgtacaac     600
tgtcacgtag gtggagcctt cagtgaggag acagaacaga agttcgaaca cttcagtgga     660
cttctaaata accagctctc tgtacagtaa                                      690
```

<210> SEQ ID NO 9
<211> LENGTH: 256
<212> TYPE: PRT
<213> ORGANISM: Homo Sapiens

<400> SEQUENCE: 9

```
Met Glu Thr Asp Thr Leu Leu Leu Trp Val Leu Leu Leu Trp Val Pro
  1               5                  10                  15

Gly Ser Thr Gly Asp Ala Ala Gln Pro Ala Gly Leu Pro Asp Leu Val
             20                  25                  30

Ala Asp Pro Tyr Tyr Ile Gln Ala Ser Thr Tyr Val Gln Lys Met Ser
         35                  40                  45

Met Tyr Asn Leu Arg Cys Ala Ala Glu Glu Asn Cys Leu Ala Ser Thr
     50                  55                  60

Ala Tyr Arg Ala Asp Val Arg Asp Tyr Asp His Arg Val Leu Leu Arg
 65                  70                  75                  80

Phe Pro Gln Arg Val Lys Asn Gln Gly Thr Ser Asp Phe Leu Pro Ser
                 85                  90                  95

Arg Pro Arg Tyr Ser Trp Glu Trp His Ser Cys His Gln His Tyr His
            100                 105                 110

Ser Met Asp Glu Phe Ser His Tyr Asp Leu Leu Asp Ala Asn Thr Gln
        115                 120                 125

Arg Arg Val Ala Glu Gly His Lys Ala Ser Phe Cys Leu Glu Asp Thr
    130                 135                 140

Ser Cys Asp Tyr Gly Tyr His Arg Arg Phe Ala Cys Thr Ala His Thr
145                 150                 155                 160

Gln Gly Leu Ser Pro Gly Cys Tyr Asp Thr Tyr Gly Ala Asp Ile Asp
                165                 170                 175

Cys Gln Trp Ile Asp Ile Thr Asp Val Lys Pro Gly Asn Tyr Ile Leu
            180                 185                 190

Lys Val Ser Val Asn Pro Ser Tyr Leu Val Pro Glu Ser Asp Tyr Thr
        195                 200                 205

Asn Asn Val Val Arg Cys Asp Ile Arg Tyr Thr Gly His His Ala Tyr
```

```
        210                 215                 220
Ala Ser Gly Cys Thr Ile Ser Pro Tyr Gly Pro Glu Gln Lys Leu Ile
225                 230                 235                 240

Ser Glu Glu Asp Leu Asn Ser Ala Val Asp His His His His His His
                245                 250                 255

<210> SEQ ID NO 10
<211> LENGTH: 771
<212> TYPE: DNA
<213> ORGANISM: Homo Sapiens

<400> SEQUENCE: 10
atggagacag acacactcct gctatgggta ctgctgctct gggttccagg ttccactggt      60
gacgcggccc agccggccgg tctcccagac ctggtggccg acccctacta catccaggcg     120
tccacgtacg tgcagaagat gtccatgtac aacctgagat gcgcggcgga ggaaaactgt     180
ctggccagta cagcatacag ggcagatgtc agagattatg atcacagggt gctgctcaga     240 tttcccaaa gagtgaaaaa ccaagggaca tcagatttct acccagccg accaagatat       300 tcctgggaat ggcacagttg tcatcaacat taccacagta tggatgagtt tagccactat     360
gacctgcttg atgccaacac ccagaggaga gtggctgaag ccacaaagc aagtttctgt     420 cttgaagaca tcctgtgtga ctatggctac acaggcgat ttgcatgtac tgcacacaca     480
cagggattga gtcctggctg ttatgatacc tatggtgcag acatagactg ccagtggatt     540
gatattacag atgtaaaaacc tggaaactat atcctaaagg tcagtgtaaa ccccagctac     600
ctggttcctg aatctgacta taccaacaat gttgtgcgct gtgacattcg ctacacagga     660
catcatgcgt atgcctcagg ctgcacaatt tcaccgtatg ggcccgaaca aaaactcatc     720
tcagaagagg atctgaatag cgccgtcgac catcatcatc atcatcattg a              771

<210> SEQ ID NO 11
<211> LENGTH: 289
<212> TYPE: PRT
<213> ORGANISM: Homo Sapiens

<400> SEQUENCE: 11

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
                20                  25                  30

Lys Leu Thr Ala Pro Asp Leu Val Leu Asn Ala Glu Met Val Gln Gln
            35                  40                  45

Thr Thr Tyr Leu Glu Asp Arg Pro Met Phe Met Leu Gln Cys Ala Met
    50                  55                  60

Glu Glu Asn Cys Leu Ser Ala Ser Ala Ala Gln Thr Asp Pro Thr Thr
65                  70                  75                  80

Gly Tyr Arg Arg Leu Leu Arg Phe Ser Ser Gln Ile His Asn Asn Gly
                85                  90                  95

Gln Ser Asp Phe Arg Pro Lys Asn Gly Arg His Ala Trp Ile Trp His
                100                 105                 110

Asp Cys His Arg His Tyr His Ser Met Glu Val Phe Thr His Tyr Asp
            115                 120                 125

Leu Leu Asn Leu Asn Gly Thr Lys Val Ala Glu Gly His Lys Ala Ser
    130                 135                 140

Phe Cys Leu Glu Asp Thr Glu Cys Glu Gly Asp Ile Gln Lys Asn Tyr
145                 150                 155                 160
```

```
Glu Cys Ala Asn Phe Gly Asp Gln Gly Ile Thr Met Gly Cys Trp Asp
                165                 170                 175
Met Tyr Arg His Asp Ile Asp Cys Gln Trp Val Asp Ile Thr Asp Val
            180                 185                 190
Pro Pro Gly Asp Tyr Leu Phe Gln Val Val Ile Asn Pro Asn Phe Glu
        195                 200                 205
Val Ala Glu Ser Asp Tyr Ser Asn Asn Ile Met Lys Cys Arg Ser Arg
    210                 215                 220
Tyr Asp Gly His Arg Ile Trp Met Tyr Asn Cys His Ile Gly Gly Ser
225                 230                 235                 240
Phe Ser Glu Glu Thr Glu Lys Lys Phe Glu His Phe Ser Gly Leu Leu
                245                 250                 255
Asn Asn Gln Leu Ser Pro Gln Ser Arg Gly Gly Pro Glu Gln Lys Leu
            260                 265                 270
Ile Ser Glu Glu Asp Leu Asn Ser Ala Val Asp His His His His His
        275                 280                 285
His
```

<210> SEQ ID NO 12
<211> LENGTH: 870
<212> TYPE: DNA
<213> ORGANISM: Homo Sapiens

<400> SEQUENCE: 12

```
atggagacag acacactcct gctatgggta ctgctgctct gggttccagg ttccactggt        60
gacgcggccc agccggccag gcgcgcgcgc cgtacgaagc ttaccgcccc tgacctggtc       120
ctcaatgcgg agatggtgca gcagaccacc tacctggagg accggcccat gttcatgctg       180
cagtgtgcca tggaggagaa ctgcctctcg gcctcagccg cgcagaccga ccccaccacg       240
ggctaccgcc ggctcctgcg cttctcctcc cagatccaca caatggccag tccgacttc        300
cggcccaaga acggccgcca cgcgtggatc tgcacgact gtcacaggca ctaccacagc        360
atggaggtgt cacccacta tgacctgctg aacctcaatg gcaccaaggt ggcagagggc        420
cacaaggcca gcttctgctt ggaggacaca gaatgtgaag agacatcca gaagaattac        480
gagtgtgcca acttcggcga tcagggcatc accatgggct gctgggacat gtaccgccat       540
gacatcgact gccagtgggt tgacatcact gacgtgcccc ctggagacta cctgttccag       600
gttgttatta accccaactt cgaggttgca gaatccgatt actccaacaa catcatgaaa       660
tgcaggagcc gctatgacgg ccaccgcatc tggatgtaca actgccacat aggtggttcc       720
ttcagcgaag agacggaaaa aaagtttgag cacttcagcg ggctcttaaa caaccagctg       780
tccccgcagt ctcgaggagg gcccgaacaa aaactcatct cagaagagga tctgaatagc       840
gccgtcgacc atcatcatca tcatcattga                                       870
```

<210> SEQ ID NO 13
<211> LENGTH: 256
<212> TYPE: PRT
<213> ORGANISM: Mus musculus

<400> SEQUENCE: 13

```
Met Glu Thr Asp Thr Leu Leu Leu Trp Val Leu Leu Leu Trp Val Pro
1               5                   10                  15
Gly Ser Thr Gly Asp Ala Ala Gln Pro Ala Gly Leu Pro Asp Leu Val
            20                  25                  30
Pro Asp Pro Tyr Tyr Ile Gln Ala Ser Thr Tyr Val Gln Lys Met Ser
        35                  40                  45
```

```
Met Tyr Asn Leu Arg Cys Ala Ala Glu Glu Asn Cys Leu Ala Ser Ser
     50                  55                  60

Ala Tyr Arg Ala Asp Val Arg Asp Tyr Asp His Arg Val Leu Leu Arg
 65                  70                  75                  80

Phe Pro Gln Arg Val Lys Asn Gln Gly Thr Ser Asp Phe Leu Pro Ser
                 85                  90                  95

Arg Pro Arg Tyr Ser Trp Glu Trp His Ser Cys His Gln His Tyr His
            100                 105                 110

Ser Met Asp Glu Phe Ser His Tyr Asp Leu Leu Asp Ala Asn Thr Gln
        115                 120                 125

Arg Arg Val Ala Glu Gly His Lys Ala Ser Phe Cys Leu Glu Asp Thr
130                 135                 140

Ser Cys Asp Tyr Gly Tyr His Arg Arg Phe Ala Cys Thr Ala His Thr
145                 150                 155                 160

Gln Gly Leu Ser Pro Gly Cys Tyr Asp Thr Tyr Ala Ala Asp Ile Asp
                165                 170                 175

Cys Gln Trp Ile Asp Ile Thr Asp Val Gln Pro Gly Asn Tyr Ile Leu
                180                 185                 190

Lys Val Ser Val Asn Pro Ser Tyr Leu Val Pro Glu Ser Asp Tyr Thr
            195                 200                 205

Asn Asn Val Val Arg Cys Asp Ile Arg Tyr Thr Gly His His Ala Tyr
210                 215                 220

Ala Ser Gly Cys Thr Ile Ser Pro Tyr Gly Pro Glu Gln Lys Leu Ile
225                 230                 235                 240

Ser Glu Glu Asp Leu Asn Ser Ala Val Asp His His His His His His
                245                 250                 255

<210> SEQ ID NO 14
<211> LENGTH: 771
<212> TYPE: DNA
<213> ORGANISM: Mus musculus

<400> SEQUENCE: 14
atggagacag acacactcct gctatgggta ctgctgctct gggttccagg ttccactggt    60
gacgcggccc agccggccgg tctcccggac ctggtgcccg acccctacta catccaggct   120
tccacgtacg tccagaagat gtctatgtac aacctgagat gcgctgcgga agaaaactgc   180
ctggccagtt cagcatatag ggcggatgtc agagactatg accacagggt actgctacga   240
tttccgcaaa gagtgaagaa ccaagggaca tcggacttct accaagccg cctcggtac    300 tcctgggagt ggcacagctg tcaccaacat taccacagca tggacgaatt cagccactat   360
gacctgcttg atgccaacac acagaggaga gtggctgaag ccacaaagc aagcttctgt   420 ctggaggaca cgtcctgtga ctatgggtac acaggcgct tgcgtgcac tgcacacaca   480 cagggattga gtcctggatg ttatgacacc tatgcggcag acatagactg ccagtggatt   540
gatattacag atgtacaacc tggaaactac attctaaagg tcagtgtaaa ccccagctac   600
ctggtgcctg aatcagacta cactaacaat gttgtacgct gtgacattcg ctacacagga   660
catcatgcct atgcctcagg ctgcacaatt tcaccgtatg ggcccgaaca aaaactcatc   720
tcagaagagg atctgaatag cgccgtcgac catcatcatc atcatcattg a           771

<210> SEQ ID NO 15
<211> LENGTH: 278
<212> TYPE: PRT
<213> ORGANISM: Mus musculus
```

```
<400> SEQUENCE: 15

Met Glu Thr Asp Thr Leu Leu Leu Trp Val Leu Leu Leu Trp Val Pro
 1               5                  10                  15

Gly Ser Thr Gly Asp Ala Ala Gln Pro Ala Thr Ala Pro Asp Leu Val
            20                  25                  30

Leu Asn Ala Glu Ile Val Gln Gln Thr Ala Tyr Leu Glu Asp Arg Pro
        35                  40                  45

Met Ser Leu Leu Gln Cys Ala Met Glu Glu Asn Cys Leu Ser Ala Ser
 50                  55                  60

Ala Val His Thr Asp Pro Thr Arg Gly His Arg Arg Leu Leu Arg Phe
 65                  70                  75                  80

Ser Ser Gln Ile His Asn Asn Gly Gln Ser Asp Phe Arg Pro Lys Asn
                85                  90                  95

Gly Arg His Ala Trp Ile Trp His Asp Cys His Arg His Tyr His Ser
            100                 105                 110

Met Glu Val Phe Thr Tyr Tyr Asp Leu Leu Ser Leu Asn Gly Thr Lys
        115                 120                 125

Val Ala Glu Gly His Lys Ala Ser Phe Cys Leu Glu Asp Thr Glu Cys
130                 135                 140

Glu Gly Asp Ile Gln Lys Ser Tyr Glu Cys Ala Asn Phe Gly Glu Gln
145                 150                 155                 160

Gly Ile Thr Met Gly Cys Trp Asp Met Tyr Arg His Asp Ile Asp Cys
                165                 170                 175

Gln Trp Ile Asp Ile Thr Asp Val Pro Pro Gly Asp Tyr Leu Phe Gln
            180                 185                 190

Val Val Ile Asn Pro Asn Tyr Glu Val Pro Glu Ser Asp Phe Ser Asn
        195                 200                 205

Asn Ile Met Lys Cys Arg Ser Arg Tyr Asp Gly Tyr Arg Ile Trp Met
210                 215                 220

Tyr Asn Cys His Val Gly Gly Ala Phe Ser Glu Glu Thr Glu Gln Lys
225                 230                 235                 240

Phe Glu His Phe Ser Gly Leu Leu Asn Asn Gln Leu Ser Val Gln Gly
                245                 250                 255

Pro Glu Gln Lys Leu Ile Ser Glu Glu Asp Leu Asn Ser Ala Val Asp
            260                 265                 270

His His His His His His
        275

<210> SEQ ID NO 16
<211> LENGTH: 837
<212> TYPE: DNA
<213> ORGANISM: Mus musculus

<400> SEQUENCE: 16
atggagacag acacactcct gctatgggta ctgctgctct gggttccagg ttccactggt      60
gacgcggccc agccggccac tgcacctgac ctggtgctta atgctgagat tgtccagcag     120
actgcctacc tggaggacag gcccatgtcc ttgctgcagt gtgccatgga ggagaactgc     180
ctctccgcct ccgctgtgca caccgacccc accagaggcc accggcgcct tttacgcttc     240
tcctcccaga tccacaacaa tggccagtct gacttccgcc caagaatggc cgccatgcg      300 tggatttggc acgactgcca caggcactac acacagcatg aagtcttcac ttactatgac     360
ctgctgagcc tcaacggcac caaggtggct gagggccaca ggccagcttc tgcctggag     420 gacactgagt gtgagggaga cattcagaag agttacgagt gtgccaactt tggagaacaa    480
```

```
ggcatcacca tgggctgctg ggacatgtac cgtcatgaca ttgactgcca gtggatagac      540
atcaccgatg tgcccctgg agactacctg ttccaggttg tcattaaccc caactatgaa       600
gtgccagaat cagatttctc taacaacatc atgaagtgca ggagccgcta tgatggctac      660
cgcatctgga tgtacaactg tcacgtaggt ggagccttca gtgaggagac agaacagaag      720
ttcgaacact tcagtggact tctaaataac cagctctctg tacagggggcc cgaacaaaaa    780 ctcatctcag aagaggatct gaatagcgcc gtcgaccatc atcatcatca tcattga         837
```

```
<210> SEQ ID NO 17
<211> LENGTH: 207
<212> TYPE: PRT
<213> ORGANISM: Homo Sapiens

<400> SEQUENCE: 17

Gly Leu Pro Asp Leu Val Pro Asp Pro Asn Tyr Val Gln Ala Ser Thr
1               5                   10                  15

Tyr Val Gln Arg Ala His Leu Tyr Ser Leu Arg Cys Ala Ala Glu Glu
            20                  25                  30

Lys Cys Leu Ala Ser Thr Ala Tyr Ala Pro Glu Ala Thr Asp Tyr Asp
        35                  40                  45

Val Arg Val Leu Leu Arg Phe Pro Gln Arg Val Lys Asn Gln Gly Thr
    50                  55                  60

Ala Asp Phe Leu Pro Asn Arg Pro Arg His Thr Trp Glu Trp His Ser
65                  70                  75                  80

Cys His Gln His Tyr His Ser Met Asp Glu Phe Ser His Tyr Asp Leu
                85                  90                  95

Leu Asp Ala Ala Thr Gly Lys Lys Val Ala Glu Gly His Lys Ala Ser
            100                 105                 110

Phe Cys Leu Glu Asp Ser Thr Cys Asp Phe Gly Asn Leu Lys Arg Tyr
        115                 120                 125

Ala Cys Thr Ser His Thr Gln Gly Leu Ser Pro Gly Cys Tyr Asp Thr
    130                 135                 140

Tyr Asn Ala Asp Ile Asp Cys Gln Trp Ile Asp Ile Thr Asp Val Gln
145                 150                 155                 160

Pro Gly Asn Tyr Ile Leu Lys Val His Val Asn Pro Lys Tyr Ile Val
                165                 170                 175

Leu Glu Ser Asp Phe Thr Asn Asn Val Val Arg Cys Asn Ile His Tyr
            180                 185                 190

Thr Gly Arg Tyr Val Ser Ala Thr Asn Cys Lys Ile Val Gln Ser
        195                 200                 205

<210> SEQ ID NO 18
<211> LENGTH: 227
<212> TYPE: PRT
<213> ORGANISM: Homo Sapiens

<400> SEQUENCE: 18

Thr Ala Ser Asp Leu Leu His Ser Ala Leu Val Gln Glu Thr Ala
1               5                   10                  15

Tyr Ile Glu Asp Arg Pro Leu His Met Leu Tyr Cys Ala Ala Glu Glu
            20                  25                  30

Asn Cys Leu Ala Ser Ser Ala Arg Ser Ala Asn Trp Pro Tyr Gly His
        35                  40                  45

Arg Arg Leu Leu Arg Phe Ser Ser Gln Ile His Asn Leu Gly Arg Ala
    50                  55                  60

Asp Phe Arg Pro Lys Ala Gly Arg His Ser Trp Val Trp His Glu Cys
```

```
            65                  70                  75                  80
His Gly His Tyr His Ser Met Asp Ile Phe Thr His Tyr Asp Ile Leu
                        85                  90                  95

Thr Pro Asn Gly Thr Lys Val Ala Glu Gly His Lys Ala Ser Phe Cys
            100                 105                 110

Leu Glu Asp Thr Glu Cys Gln Glu Asp Val Ser Lys Arg Tyr Glu Cys
            115                 120                 125

Ala Asn Phe Gly Glu Gln Gly Ile Thr Val Gly Cys Trp Asp Leu Tyr
            130                 135                 140

Arg His Asp Ile Asp Cys Gln Trp Ile Asp Ile Thr Asp Val Lys Pro
145                 150                 155                 160

Gly Asn Tyr Ile Leu Gln Val Val Ile Asn Pro Asn Phe Glu Val Ala
                165                 170                 175

Glu Ser Asp Phe Thr Asn Asn Ala Met Lys Cys Asn Cys Lys Tyr Asp
                180                 185                 190

Gly His Arg Ile Trp Val His Asn Cys His Ile Gly Asp Ala Phe Ser
                195                 200                 205

Glu Glu Ala Asn Arg Arg Phe Glu Arg Tyr Pro Gly Gln Thr Ser Asn
            210                 215                 220

Gln Ile Ile
225

<210> SEQ ID NO 19
<211> LENGTH: 226
<212> TYPE: PRT
<213> ORGANISM: Homo Sapiens

<400> SEQUENCE: 19

Ser Ala Pro Asp Leu Val Met Asn Ala Gln Leu Val Gln Glu Thr Ala
1               5                   10                  15

Tyr Leu Glu Asp Arg Pro Leu Ser Gln Leu Tyr Cys Ala His Glu Glu
                20                  25                  30

Asn Cys Leu Ser Lys Ser Ala Asp His Met Asp Trp Pro Tyr Gly Tyr
            35                  40                  45

Arg Arg Leu Leu Arg Phe Ser Thr Gln Ile Tyr Asn Leu Gly Arg Thr
50                  55                  60

Asp Phe Arg Pro Lys Thr Gly Arg Asp Ser Trp Val Trp His Gln Cys
65                  70                  75                  80

His Arg His Tyr His Ser Ile Glu Val Phe Thr His Tyr Asp Leu Leu
                85                  90                  95

Thr Leu Asn Gly Ser Lys Val Ala Glu Gly His Lys Ala Ser Phe Cys
            100                 105                 110

Leu Glu Asp Thr Asn Cys Pro Thr Gly Leu Gln Arg Arg Tyr Ala Cys
            115                 120                 125

Ala Asn Phe Gly Glu Gln Gly Val Thr Val Gly Cys Trp Asp Thr Tyr
            130                 135                 140

Arg His Asp Ile Asp Cys Gln Trp Val Asp Ile Thr Asp Val Gly Pro
145                 150                 155                 160

Gly Asn Tyr Ile Phe Gln Val Ile Val Asn Pro His Tyr Glu Val Ala
                165                 170                 175

Glu Ser Asp Phe Ser Asn Asn Met Leu Gln Cys Arg Cys Lys Tyr Asp
                180                 185                 190

Gly His Arg Val Trp Leu His Asn Cys His Thr Gly Asn Ser Tyr Pro
                195                 200                 205

Ala Asn Ala Glu Leu Ser Leu Glu Gln Glu Gln Arg Leu Arg Asn Asn
```

```
                  210                 215                 220

Leu Ile
225

<210> SEQ ID NO 20
<211> LENGTH: 7
<212> TYPE: PRT
<213> ORGANISM: Artificial Sequence
<220> FEATURE:
<223> OTHER INFORMATION: N-terminal of hLOX

<400> SEQUENCE: 20

Gly Leu Pro Asp Leu Val Ala
  1               5

<210> SEQ ID NO 21
<211> LENGTH: 5
<212> TYPE: PRT
<213> ORGANISM: Artificial Sequence
<220> FEATURE:
<223> OTHER INFORMATION: N-terminal of hLOX2

<400> SEQUENCE: 21

Thr Ala Pro Asp Leu
  1               5

<210> SEQ ID NO 22
<211> LENGTH: 7
<212> TYPE: PRT
<213> ORGANISM: Artificial Sequence
<220> FEATURE:
<223> OTHER INFORMATION: N-terminal of mLOX

<400> SEQUENCE: 22

Gly Leu Pro Asp Leu Val Pro
  1               5
```